United States Patent [19]
Rhodes et al.

[11] Patent Number: 5,666,492
[45] Date of Patent: Sep. 9, 1997

[54] FLEXIBLE COMPUTER BASED PHARMACEUTICAL CARE COGNITIVE SERVICES MANAGEMENT SYSTEM AND METHOD

[75] Inventors: Keith Daniel Rhodes, Cary; Kenneth Wayne Dunn, Durham; Samir Ibrahim Abed, Durham; Donald Collins Mullen, Jr., Durham; Jon Martin Schwartz, Carrboro, all of N.C.

[73] Assignee: Glaxo Wellcome Inc., Research Triangle Park, N.C.

[21] Appl. No.: 373,105

[22] Filed: Jan. 17, 1995

[51] Int. Cl.$^6$ .................................................. G06F 15/02
[52] U.S. Cl. .......................................... 705/3; 705/4; 705/2
[58] Field of Search ..................... 395/157; 364/413.01, 364/413.02, 401

[56] References Cited

U.S. PATENT DOCUMENTS

| | | | |
|---|---|---|---|
| 4,546,901 | 10/1985 | Buttarazzi | 221/10 |
| 4,839,806 | 6/1989 | Goldifscher et al. | 364/413.02 |
| 4,847,764 | 7/1989 | Halvorson | 364/413.02 |
| 5,299,121 | 3/1994 | Brill et al. | 364/413.01 |

OTHER PUBLICATIONS

SDP Technologies, Inc., S–Designor Corporate Release 4.0 User's Guide: Powerful Database Design Made Simple, 1992–93, pp. 12–33.
PharmCare Pharmacist Training Manual, Pharmaceutical Care Services, Inc., Jeanne Ann Stasny, 1993.
The Medi–Span DUR Databases™ User's Guide, Medi–Span, Inc., Indianapolis, IN 1994.
RxEXPRESS 5.0 Release Notes, Comco Tec, Inc. Health Care Systems and Services, Lombard, IL.

(List continued on next page.)

*Primary Examiner*—Gail O. Hayes
*Assistant Examiner*—Krishna V. Kalidindi
*Attorney, Agent, or Firm*—Bell, Seltzer, Park and Gibson; Charles E. Dadswell

[57] ABSTRACT

A computer based pharmaceutical care cognitive services management system and method allows the transformation of a pharmacist from a vendor to a health care provider. The pharmaceutical care cognitive services management system and method captures all of the value added by a pharmacist to a patient encounter by permitting multiple RARs (Reasons, Actions, Results) to be associated with a single SOAP (Subjective, Objective, Assessment, Plan). This system enables the pharmacist to financially recover for each analytical or counseling session and/or service provided to the user associated with a single transaction. The pharmaceutical care cognitive services management system and method also enables the efficient processing of interruptions to cognitive and counseling sessions. When a pharmacist receives an interruption from a patient in the nature of a telephone call or an in-person interruption, or in the nature of a physician requesting a refill for a prescription by telephone, the pharmaceutical care cognitive services management system and method suspends the cognitive or counseling session for a first patient, processes the interrupt for the second patient or refill request, and upon completion of the processing of the interrupt for the second patient or refill request, resumes processing of the cognitive or counseling session for first patient.

13 Claims, 56 Drawing Sheets

OTHER PUBLICATIONS

RxEXPRESS Pharmacy System: Prescription System and Optional Packages, Book I, ComCoTec, Inc., Burr Ridge, IL.

RxEXPRESS Pharmacy System: General Information and Maintenance, Book II, ComCoTec, Inc., Burr Ridge, IL.

RxEXPRESS Pharmacy System: Reporting Systems and Word Processing, Book III, ComCoTec, Inc., Burr Ridge, IL.

RxEXPRESS Pharmacy System: Third Party and Accounts Receivable System, Book IV, ComCoTec, Inc., Burr Ridge, IL.

RxEXPRESS PC Based Pharmacy Management System Quick Reference Guide, ComCoTec, Inc., Lombard, IL.

RxEXPRESS Pharmacy System 5.1 Release Notes, ComCoTec, Inc. Health Care Systems and Services, Lombard, IL.

DePietro, Tocco, Tramontozzi; "Incentives for Pharmacy Automation"; Healthcare Informatics (USA), Dec. 1994; vol. 11, pp. 35–46.

Anonymous; "Medicaid Program: Drug Use Review Program and Electronic Claims Management System for Outpatient Drug Claims"; Federal Register (USA); Sep. 23, 1994; vol. 59; pp. 48811–48825.

Banahan, Garner; "Using Pharmacy Computer Systems for Better Patient Care"; Drug Topics (USA); Jan. 10, 1994; vol. 138, pp. 80–88, 90–91.

Christensen, Fassett; "Making a Claim for Cognitive Services"; ComputerTalk for the Pharmacist (USA); Sep.–Oct. 1993; vol. 13, pp. 30–31.

Decker; "Health–Care Reform May Require Computer System Reform"; Hospital Pharmacist Report; Feb. 1994; vol. 8, p. 56.

Anonymous; "Profit Pressure: Noose Tightens"; ComputerTalk for the Pharmacist (USA); May–Jun. 1992; vol. 12, pp. 18–24.

Price; "Documentation of Cognitive Clinical Pharmacy Services"; ASHP Midyear Clinical Meeting; Dec. 1992; vol. 27, p. SPG–30.

Arrison; "Documenting Pharmaceutical Care Interventions"; ASHP Annual Meeting; Jun. 1991; vol. 48, p. P–127D.

McCarty; "Status of Community Pharmacy in the USA"; Indian Journal of Hospital Pharmacy (India); Mar.–Apr. 1985; vol. 22, p. 106.

Anonymous; "Surviving and Thriving: Technology's New Directions"; ComputerTalk for the Pharmacist (USA); Jan.–Feb. 1995; vol. 15, pp. 18–29.

Lundquist, Witte; "Implementing a Computerized Documentation Program Linking Both Administrative and Pharmaceutical Care Needs"; ASHP Midyear Clinical Meeting; Dec. 1994; vol. 29, p. MCS–25.

Schneider, Labatt; "Implementation of a Computerized Physician Order Entry System"; ASHP Midyear Clinical Meeting; Dec. 1994; vol. 29, p. MCS–8.

Keefe, Trussell, Adams, Caffey; "Automation in Support of Pharmaceutical Care"; ASHP Midyear Clinical Meeting; Dec. 1994; vol. 29, p. P–235(D).

Schelesselman, Jones; "Enhancing the Provision of Pharmaceutical Care Utilizing Local Area Network Applications"; ASHP Midyear Clinical Meeting; Dec. 1994; vol. 29, p. MCS–27.

Iacovelli; "Clinical Intervention Documentation: Modification of Existing Hospital Automation to Develop an Institution Unique System"; ASHP Midyear Clinical Meeting; Dec. 1994; vol. 29, p. P–21(D).

McCall, Wade; "Use of a Database Program to Document the Practice of Pharmaceutical Care During Order Entry"; ASHP Annual Meeting; Jun. 1994; vol. 51, p. P–56(D).

MacKinnon; "Evolving Strategies in Drug Usage Evaluation (Due)"; ASHP Annual Meeting; Jun. 1994; vol. 51, p. PI–32.

Rorstrom, Pascale, Rotella: "Using Computer Technology to Document Pharmaceutical Care Services"; ASHP Midyear Clinical Meeting; Dec. 1993; vol. 28, p. P–116(R).

Melby, Coffey, Fisher, Coale, Veenstra; "Implementing a Comprehensive System for Documenting Pharmaceutical Care Interventions on a Gerber–Alley Mainframe Computer"; ASHP Midyear Clinical Meeting; Dec. 1993; vol. 28, p. MCS–34.

Mickle; "Increasing Staff Pharmacists' Interventions With a Structured Program Utilizing the Pharmacy's Existing Computer System"; ASHP Annual Meeting; Jun. 1993; vol. 50, p. P–44D.

Phillips, Apostolo; "Pharmacotherapy Interventions: Chaning Hi Tech/Low Touch into Low Tech/Hi Touch"; ASHP Midyear Clinical Meeting; Dec. 1992; vol. 27, p. PI–89.

Schultz, Meares, Hall; "Mainframe Pharmacist Intervention Log With Spreadsheet Capabilities"; ASHP Midyear Clinical Meeting; Dec. 1992; vol. 27, p. P–7D.

Barker, Harris, Swanson; "Documenting Pharmacists' Clinical Interventions: Making a Difference in Patient Care"; ASHP Midyear Clinical Meeting; Dec. 1992; vol. 27, p. MCS–28.

VanDerLinde, Apostolo, Baker; "Case Study III: Comprehensive Model for Drug Therapy Monitoring"; ASHP Midyear Clinical Meeting; Dec. 1992; vol. 27, p. PI–88.

Farrar, Hughes; "Beneficial Impact of Clinical Pharmacy Intervention Review on Quality Improvement of Prescribing"; ASHP Midyear Clinical Meeting; Dec. 1992; vol. 27, p. P–679I.

Schumock, Hutchinson, Bilek; "Comparison of Two Systems for Documenting Pharmacist Interventions in Patient Care"; American Journal of Hospital Pharmacy (USA); Sep. 1992; vol. 49, pp. 2211–2214.

Phillips, Williams, May; "Utilizing Pharmacist Intervention Data in the Physician Credentialing Process"; ASHP Midyear Clinical Meeting; Dec. 1991; vol. 26, p. P–494D.

Beaulieu, Wyman, Mahoney; "Outcome Oriented Systems Integrating a Clinical Pharmacist Intervention Database Into Existing Quality Assurance Programs"; ASHP Midyear Clinical Meeting; Dec. 1991; vol. 26, p. P–491D.

Ensign, Burkhart, Wareham, Gross, Hurner; "JCAHO's Agenda for Change: Where Does a Computerized Intervention Program Fit?"; ASHP Midyear Clinical Meeting; Dec. 1991, vol. 26, p. P–492D.

Dolph; Endo; "Development of a Paperless Clinical Documentation System; Utilizing a Laptop Computer to Facilitate Documentation of Antibiotic Formulary Management, Pharmacist Interventions, and Drug Utilization Evaluation"; ASHP Midyear Clinical Meeting; Dec. 1991; vol. 26, p. MCS–46.

Bendinelli, Bosh; "Development and Utilization of a Computerized Drug Interaction Program to Document Patient Outcomes"; ASHP Annual Meeting; Jun. 1991; vol. 48, p. MCS–32.

Zeisler, Richelieu; "Computer Generated Serum Creatinine Report: Means for Individualizing Drug Therapy (Research in Progress)"; ASHP Annual Meeting; Jun. 1991; vol. 48, p. P–1R.

Reents, Hatton, Iafrate, Wise, Williams et al; "Documenting and Evaluating Clinical Interventions"; ASHP Midyear Clinical Meeting; Dec. 1990; vol. 25, p. P–295D.

Gray, Syverson, Chretien, Puglisi, Schack; "Documentation and Assessment of Pharmacist Initiated Drug Therapy Interventions"; ASHP Midyear Clinical Meeting; Dec. 1990; vol. 25, p. P–292D.

Giambrone, Berggren; "Documentation of Inpatient Clinical Pharmacy Services in an HMO Using an Automated Drug Usage Review Report"; ASHP Midyear Clinical Meeting; Dec. 1989; vol. 24, p. HMO–8.

Johnson, Generali, Habershaw, D'Agostino; "Clinical and Economic Impact of Avoiding Computer Identified Drug Interactions"; ASHP Midyear Clinical Meeting; Dec. 1989; vol. 24, p. P–296R.

Robinson, Lopez, Stewart; "How to Establish a Pharmacokinetic Consulting Service for Ambulatory Patients"; American Journal of Hospital Pharmacy (USA); Oct. 1984; vol. 41, pp. 2048–2053.

Martin, Sara, "Pharmaceutical Care Made Easy", *Innovative Practice*, vol. NS34, No. 3, Mar. 1994.

Stasny, Jeanne Ann, "Pharmaceutical Care Training Manual", *Pharmaceutical Care Services, Inc.*, Section 9, pp. 1–3.

Martin, S. "Pharmaceutical Care Made Easy", American Pharmacy, pp. 61–64 Mar. 1994.

Patient Intake

Pt Requests — 291
Pt Chart — 292
New Pt — 293
Cancel — 294
Help — 295

Last Name:
First Name:
Search — 296

| Name | Gender | Age | Phone |
|---|---|---|---|
| Anderson, John R. | M | 40 | (919)555-6324 |
| Bortz, Maxwell A. | M | 36 | (919)555-6023 |
| Brown, Candace A. | F | 18 | (919)555-3604 |
| Brown, Candace Burton | F | 40 | (617)555-5584 |
| Doe, Richard Peter | M | 28 | (919)555-6641 |
| Green, Lorraine Paula | F | 36 | (910)555-1700 |
| Person, Ima Test | | | (0)555-1212 |
| Rogers, Christy Kane | F | 36 | (0)555-2037 |
| Rogers, Keith Daniel | M | 38 | (0)555-2037 |

Select the patient and press the [Pt Chart] or [Pt Intake] button.

SOAPs and RARs

SOAP content
CSR

Subjective:
Before counseling pt does not understand drug

Objective:
Ceftin TAB 125 mg

Assessment:
General health problems

Plan:
Talk to doctor about health issues

Blood Pressure

Buttons: OK (351), Cancel (353), Suspend (352), Add RAR (354), Delete RAR (355), Help (356)

SOAPs and RARs

351 — OK
353 — Cancel
352 — Suspend
354 — Add RAR
355 — Delete RAR
356 — Help

SOAP
Context: CSR

Subjective: Believe patient drinks heavily

Objective: Bloodshot eyes, smells of liquor at 11:00 am

Assessment: Possible complications with therapy, general health problem

Plan: Talk to patient about complications with therapy, talk to doctor about health issues Procedure: None Enter the plan for resolving this problem.

FIGURE 35

Patient Intake

Last Name: R

First Name:

| Name | Gender | Age | Phone |
|---|---|---|---|
| Rogers, Christy Kane | F | 36 | ()555-2037 |
| Rogers, Keith Daniel | M | 38 | ()555-2037 |
| Rogers, Kimberly | F | 8 | (919)555-2037 |

Search — 296

- 292 Pt Requests
- 291 Pt Chart
- 293 New Pt
- 294 Cancel
- 295 Help

Select the patient and press the [Pt Chart] or [Pt Intake] button.

FLEXIBLE COMPUTER BASED PHARMACEUTICAL CARE COGNITIVE SERVICES MANAGEMENT SYSTEM AND METHOD

FIELD OF THE INVENTION

This invention relates to systems and methods used by pharmacists, and more particularly to computer based pharmaceutical care cognitive services management systems which allow a pharmacist to more efficiently conduct an encounter with pharmacy patients.

BACKGROUND OF THE INVENTION

The role of pharmacists is quickly moving from that of a vendor to that of a health care provider. As a result, pharmacists are increasingly concerned about advising patients regarding the selection, use and side effects of over-the-counter and prescription drugs. A pharmacist typically obtains information relating to the patient's history directly from the patient, accepts orders for over-the-counter and prescription drugs; conducts an analysis in terms of a cognitive review of the drug and the patient's history, and conducts a counseling session with the patient during which the pharmacist advises the patient about substitute generic drugs, provides instructions for administering the drug, and advises the patient about possible side effects resulting from use of the drug. Thereafter, the pharmacy dispenses the prescribed drug or an equivalent generic drug.

Recently, computer based systems have been introduced to automate this process. Pharmaceutical care systems, typically controlled by a microprocessor, assist a pharmacist in analyzing the impact of drugs with respect to particular patients and to correspondingly provide advice to particular patients based on particular over-the-counter or prescription drugs and specific patient histories. The computer based systems may include a processing unit, a keyboard, a display screen and a printer. These systems assist in the collecting (i.e., intake) of patient history information, conducting of a cognitive analysis, counseling of patients, and dispensing over-the-counter and prescription drugs.

One example of a computer based system used by pharmacists is the PharmCare™ system marketed by Pharmaceutical Care Services, Inc. of Waco, Texas. PharmCare™ provides a sequential workflow and is mitten in a high level computer language such as Cobol. The PharmCare™ system assists the user with collecting patient information, conducting of cognitive and counseling sessions, and correlating the results of the cognitive and counseling sessions. During cognitive analysis, the PharmCare™ system conducts an automated drug utilization review ("DUR") (also sometimes referred to as drug regimen review ("DRR") during which an interactive check is made between the over-the-counter or prescribed drug and allergies, pregnancy status, age, and other characteristics and conditions of the patient. During the cognitive phase of the PharmCare™ system, and in particular, during DUR, a pharmacist can create a "SOAP." "SOAP" stands for "Subjective" data, "Objective" data, "Assessment" of data, and "Plan." The subjective data generally refers to any data received that is opinion based while the objective data refers to any data received that is factual based. During the assessment phase, the pharmacist conducts an analysis of the solutions after collecting the data and running the drug review. During planning, the pharmacist determines the action to be taken based on the results of the assessment.

Specifically, the subjective data includes diagnoses, allergies, adverse drug reactions, lifestyle information, problems in general or with drugs, drugs not purchased at the particular pharmacy, over-the-counter drugs presently being taken by the patient, the patient's physicians, the patient's symptoms, and socio-economic considerations. The objective data is a profile of the patient's drug history, and includes data relating to interactions between drugs, interactions between drugs and diseases, interactions between drugs and food, as well as the age and weight of the patient. Additional miscellaneous data is also considered during the SOAP analysis for consistency purposes. The miscellaneous data includes refill frequency dates, nature of over-the-counter drug use, a patient's understanding of particular situations and target goals of the therapy, and a pharmacist's observation of the results of the consultation session with the patient.

During assessment, the pharmacist determines if each of the subjective and objective data are in order and if any problem exists or potential problem exists as a result of the subjective and objective data. For example, a drug incompatibility may exist or the drug prescribed for the patient may be inconsistent with the patient's lifestyle. Finally, during planning, the pharmacist identifies an action to remove any potential or existing negative results of the drug use, sets target goals, if necessary, and follows up on any previous progress notes.

The PharmCare™ system also provides for creation of a RAR (i.e., "Reason," "Action" and "Result"). During a RAR, the pharmacist documents the actual action taken as a result of the interaction between the pharmacist and the patient in order to justify billing the patient or third party payer for the consultation session with the patient. In general, SOAP refers to the clinical portion of the analysis and RAR refers to the billing or financial portion resulting from the analysis. The PharmCare™ system allows the user to associate one RAR with one SOAP.

Unfortunately, the prior art systems do not provide the flexibility necessary in order to fully transform the role of a pharmacist from a drug vendor or dispenser to a health care provider, allowing the pharmacist to recapture the value added by the pharmacist during encounters with patients. For example, the pharmacist may not be able to recapture all of the value added by the pharmacist during the encounter with the patient and subsequently bill the patient or third party payer for the total value added by the pharmacist.

In addition, it is not uncommon for the pharmacist to be interrupted while performing tasks. Prior art systems are indexed, sequential database systems which may require the system to discontinue any analysis being conducted when the interruption is received.

SUMMARY OF THE INVENTION

It is, therefore, an object of the present invention to provide a flexible computer based pharmaceutical care cognitive services management system.

It is another object of the present invention to provide a computer based pharmaceutical care cognitive services management system for capturing all of the value added by a pharmacist to a patient encounter.

These and other objects are provided according to the present invention by a computer based pharmaceutical care cognitive services management system which executes on a computer system. The computer system includes a processor, a data storage device, a display device and an input device. The computer based pharmaceutical care cognitive services management system compromises a number of subsystems including a patient intake subsystem which includes a patient chart component and a cognitive service record component, a cognitive subsystem, a counseling subsystem, a report generation subsystem, a SOAP (Subjective, Objective, Assessment, Plan) and RAR (Reason, Action, Result) subsystem and an interrupt subsystem.

It is not uncommon for a pharmacist to provide multiple analyses during a single patient encounter and thus add significant value to the encounter with the patient. The present invention allows the pharmacist to recapture the significant value added to the encounter with the patient for each analysis performed by the pharmacist. In particular, the present invention allows a pharmacist to associate multiple billing sessions, i.e., multiple RARs, with one SOAP.

In addition, a pharmacist is often interrupted during a cognitive or counseling session involving a particular patient. Interruptions may include a second patient calling to ask the pharmacist questions about a particular prescription or personally visiting the pharmacist, as well as telephone requests to refill particular prescriptions. The present invention does not require the pharmacist to terminate any cognitive or counseling session being conducted to handle any interruptions and restart the terminated cognitive or counseling session from the beginning after processing of the interruptions. Rather, the pharmaceutical care cognitive services management system and method suspends the interrupted cognitive or counseling session, completes the processing of the interrupt by a patient or a request for a prescription refill, and restarts the suspended cognitive or counseling session from the point of suspension rather than from the beginning. The restart of the suspended session may be automatic or may be enabled by the user.

In particular, the computer based pharmaceutical care cognitive services management system and method prompts the user on the display device to enter identity and history information corresponding to a particular patient using the input device, and stores the identity and history information corresponding to the patient and entered by the user in the data storage device. The pharmaceutical care cognitive services management system also prompts the user on the display device for entry of subjective information relating to assessed characteristics of the patient and objective information relating to the patient's drug use history, and stores the subjective and objective information entered by the user in the data storage device. The user is also prompted on the display device to enter an assessment of the patient, and also is prompted to enter a plan to follow based on the assessment. The assessment and the plan entered by the user are also stored in the storage device.

The pharmaceutical care cognitive services management system prompts the user on the display device to enter a first reason for the assessment and the plan, a first action in response to the assessment and the plan, and a first result based on the first action. In addition, the pharmaceutical care cognitive services management system prompts the user to enter a second reason for the assessment and the plan, a second action in response to the assessment and the plan, and a second result based on the second action. The first reason, the first action and the first result as well as the second reason, the second action and the second result are stored in the data storage device. Finally, the pharmaceutical care cognitive services management system associates the first reason, the first action and the first result and the second reason, the second action and the second result with the subjective and objective information, the assessment and the plan for the particular patient. As a result, a multiple number of reasons, actions and results are associated with a single stored set of subjective information, objective information, assessment and plan for one patient.

The pharmaceutical care cognitive services management system also generates a first billing statement for the patient based on the first reason, first action and first result as well as a second billing statement for the patient based on the second reason, second action and second result. Thus, the pharmaceutical care cognitive services management system generates two billing statements for one patient based on the one set of subjective information, objective information, assessment and plan allowing the pharmacist to recapture all of the value added by the pharmacist during the encounter with the patient.

The pharmaceutical care cognitive services management system also prompts the user on the display device to enter a prescription using the input device, and stores the prescription entered by the user in the data storage device. The prescription is associated with the patient identity stored in the data storage device, and is compared with the identity and history information corresponding to the patient to produce an indication of possible incompatibilities between the prescription and the patient. The user is also prompted on the display device to enter any changes or alterations to the prescription based on the indications of the possible incompatibilities between the drug and the patient resulting from the comparison between the two. If the user invokes an interrupt during the comparison of the prescription and the patient, or while the prescription is being changed or altered based on any indications of possible incompatibilities between the prescription and the patient, the pharmaceutical care cognitive services management system suspends any prompting of the user to change or alter the prescription and displays information to the user on the display device relating to a second patient. Once processing of the second patient is completed, prompting of the user to change or alter the prescription for the first patient is resumed at the point of suspension.

The user is also prompted on the display device to enter results of a counseling session between the pharmacist and the patient. This process of prompting the user for entry of results of the counseling session is suspended in response to a user interrupt and information concerning a third patient is displayed on the display device. Upon completion of the processing of the third patient, the pharmaceutical care cognitive services management system resumes prompting of the user for entry of the results of the counseling session with the first patient at the point of suspension of the prompting process. These user interrupts may range from merely viewing information relating to the second patient to processing a request by a second patient or a physician to refill a prescription or to fill a new prescription.

In the preferred embodiment, the user may interrupt processing by any of the patient intake, cognitive, counseling, SOAP and RAR or report generation subsystems. In addition, the user may cause the pharmaceutical care cognitive services management system to transfer control from any one subsystem to any other subsystem during use.

BRIEF DESCRIPTION OF THE DRAWINGS

A preferred form of the invention is illustrated in the accompanying drawings, in which:

FIGS. 5 through 48 illustrate display screens which are presented to a user and demonstrate the operational logic of the present invention;

DESCRIPTION OF THE PREFERRED EMBODIMENT

The present invention now will be described more fully hereinafter with reference to the accompanying drawings, in which a preferred embodiment of the invention is shown. This invention may, however, be embodied in many different forms and should not be construed as limited to the embodiment set forth herein; rather, this embodiment is provided so that this disclosure will be thorough and complete, and will fully convey the scope of the invention to those skilled in the art. Like numbers refer to like elements throughout.

Figure 1:
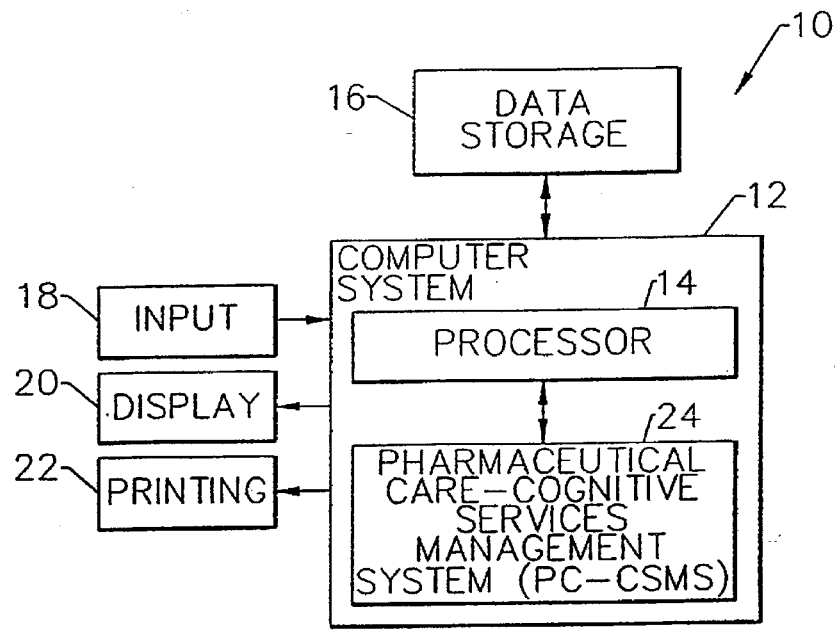
FIG. 1 is a high level block diagram of the computer based pharmaceutical care cognitive services management system.

Overview: Computer Based Pharmaceutical Care Cognitive Services Management System Referring to FIG. 1, a general overview of a computer based pharmaceutical care cognitive services management system 10 will be described. The system 10 includes a computer system 12 having processor means 14 and pharmaceutical care cognitive services management system ("PC-CSMS") 24. The computer system is connected to data storage means 16. In addition, the computer system 12 is also connected to several input/output peripheral devices including input means 18, display means 20, and printing means 22. Input means 18 may consist of a keyboard, a mouse, a virtual track ball, a light pen, or any other number of devices, individually or collectively used for entering data or selecting options in computing environments. Display means 20 may be a color cathode ray tube, or any other type of display device. Finally, printing means 22 may be a laser printer, or any other type of printing device and may be used for printing patient reports and billing statements.

Preferably, processor means 14 is a personal computer. Data storage means 16 may include hard disk drives, tapes, etc. or any combination thereof. Processor 14 communicates with input device 18, display device 20, printing device 22 and data storage device 16. The computer system also contains pharmaceutical care cognitive services management system or PC-CSMS 24. PC-CSMS 24 communicates with processor 14. PC-CSMS 24 is preferably implemented as a stored program which executes on processor 14.

Figure 2:
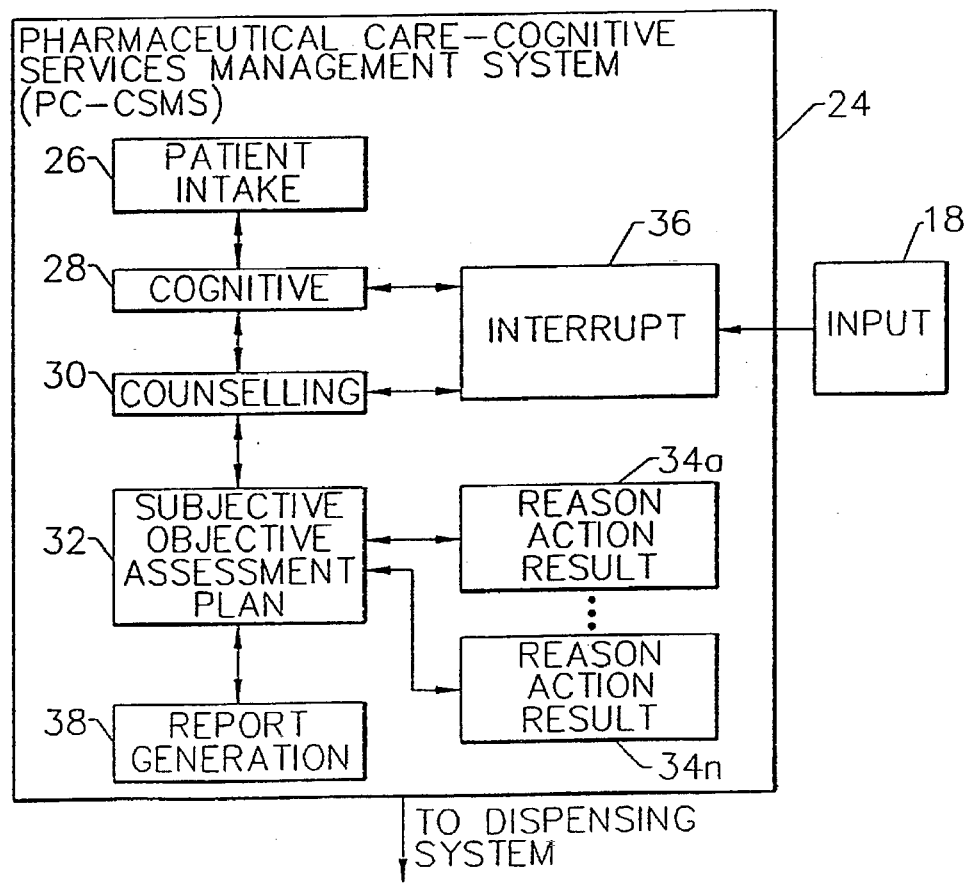
FIG. 2 is a block diagram of the pharmaceutical care cognitive services management system referred to in FIG. 1.

Referring to FIG. 2, a block diagram of pharmaceutical care cognitive services management system or PC-CSMS 24 will now be described. PC-CSMS 24 contains subsystems for patient intake 26, cognitive 28, counseling 30, and SOAP 32 (also referred to as Subjective, Objective, Assessment and Plan). The PC-CSMS according to the present invention also provides multiple RAR subsystems 34 (also known as Reason, Action and Result), an interrupt subsystem 36 and a report generation subsystem 38. The PC-CSMS may be operationally connected to a dispensing system (not shown) for dispensing drugs for a particular patient after conclusion of management of the pharmaceutical process by a pharmacist or user of PC-CSMS 24.

The components of PC-CSMS 24 will now be described generally. A detailed description of these components will be described below in the sections labeled "Detailed Operation." Patient intake subsystem 26 consists of two components (i.e., patient chart and cognitive service record). The patient chart component prompts a user of PC-CSMS 24 to enter via input device 18, and then stores in data storage device 16, information regarding a patient's identity and history including general information relating to name, residence and demographics, insurance, medical and miscellaneous information. The patient chart component is only implemented for new patients and updating of information for existing patients. The cognitive service record component displays information on display device 20, and prompts a user on the display device to enter, via input device 18, and then stores in data storage device 16, information relating to drug requests permitting a user of PC-CSMS 24 to view and survey work to be done for a patient, additional personal information about a patient specific to the present encounter between the patient and the user of PC-CSMS 24, and a summary of information already known about the patient. The patient chart and cognitive service record components may be used by a technician in addition to being used by a pharmacist.

Cognitive subsystem 28 is implemented by PC-CSMS 24 to perform a drug regimen review. During implementation of cognitive subsystem 28, which may be only invoked by a pharmacist, PC-CSMS 24 displays a summary of patient information regarding a particular encounter between a pharmacist and a patient on display device 20, and prompts the user for assignment of patient categories and modules with respect to the patient and the prescribed or over-the-counter drugs. Cognitive subsystem 28 also manages the therapy review of the interactions between the patient and the prescribed or over-the-counter drug and permits the user (i.e., pharmacist) to select alternative medications via input device 18 if problems occur based on the interactions between the drug and the patient. Cognitive subsystem 28 also displays a summary of information known about the patient on display device 20 for easy reference. The patient need not be present during execution of the cognitive subsystem 28.

Counseling subsystem 30 of PC-CSMS 24 brings together the patient, the pharmacist and the drug. During counseling, the patient is physically present with the user of the pharmaceutical care cognitive services management system. Counseling subsystem 30 controls a therapy management session to ensure the patient understands what drug he is getting, the purpose of the drug and the effects of the drug. Counseling subsystem 30 also controls the standard of care by prompting the user on display device 20 to indicate that the various steps in the counseling session have been completed. Further, counseling subsystem 30 also manages the encounter between the patient and the user by reminding the user of modules and SOAPs not completed. Finally, similar to patient intake subsystem 26 and cognitive subsystem 28, counseling subsystem 30 also displays a summary of patient information on display device 20 for ease of reference by the user of PC-CSMS 24.

Report generation subsystem 38 initiates the generation of reports regarding encounters between patients and users of PC-CSMS 24 as well as billing statements and other information and financial reports. Similarly, PC-CSMS 24 may be operationally connected to a dispensing system (not shown) for dispensing the drug prescribed for the patient or the drug alternatively selected by the user of the pharmaceutical care cognitive services management system 24 after completion of counseling subsystem 30. A number of dispensing systems are presently available including RxExpress marketed by ComCoTech of Chicago, Ill.

Still referring to FIG. 2, SOAP subsystem 32 of PC-CSMS 24 enables the user of PC-CSMS 24 to document the encounter with the patient from a medical perspective. SOAP subsystem 32 controls the collection of subjective or opinion based information relating to the patient, objective or factual based information relating to the patient, entry and storage of an assessment of the relationship between the subjective information and the objective or factual based information, and entry and storage of a plan to be followed which is based on the assessment.

RAR subsystems 34a through 34n controls the documentation by the user of the reason for the assessment and plan of SOAP subsystem 32, the action taken by the user due to the assessment and plan of SOAP subsystem 32, and the result of the action corresponding to the assessment and plan of SOAP subsystem 32. RAR subsystem 34 allows the pharmacist to recapture the value added by his encounter with the patient controlled by SOAP subsystem 32. Multiple RARs 34a through 34n can be associated with a single SOAP. Association of multiple RARs 34a through 34n with a single SOAP permits the user of PC-CSMS 24 to recapture all of the value added by the user during the encounter with the patient and subsequently generate multiple reports and/or billing statements corresponding to the single encounter with the patient. Multiple RARs can be listed individually as separate entries (i.e., one per line) on a single billing statement. Thus, multiple RARs associated with a single SOAP allow the user of PC-CSMS 24 to capture the total value added by the user during the encounter with the patient. The number of RARs which can be associated with a single SOAP is essentially unlimited, but in the present embodiment is limited to four.

Interrupt subsystem 36 which is invoked externally by the user of PC-CSMS 24 permits the user of PC-CSMS 24 to suspend processing by cognitive subsystem 28 or counseling subsystem 30. The user of PC-CSMS 24 invokes interrupt subsystem 36 via input device 18 Upon receiving a telephone call from a patient or a patient interrupting the user in person. Interrupt subsystem 36 controls the review, updating or creation of patient records stored in data storage device 16 as well as processing of requests for refilling a prescription. Upon completion of the review, update or creation of the patient record or entry of the request for refilling of a prescription for a drug, processing of the suspended cognitive or counseling session is resumed and continues until completed.

Pharmaceutical care cognitive services management system 24 also permits a user to tag a note to a particular patient or encounter or to simply remind a user of some task to be completed at a later date. Still further, PC-CSMS 24 also interfaces with one or more drug databases. Moreover, PC-CSMS 24 permits a user to communicate with other users via electronic mail, to access an online scheduler or calendar and to access online assistance or help.

Finally, since PC-CSMS 24 is implemented in a Windows™ environment, it has a number of common pull-down menus including "File," "Edit," "Views," "Action," "Reports," "Utilities," and "Help."

Figure 3:
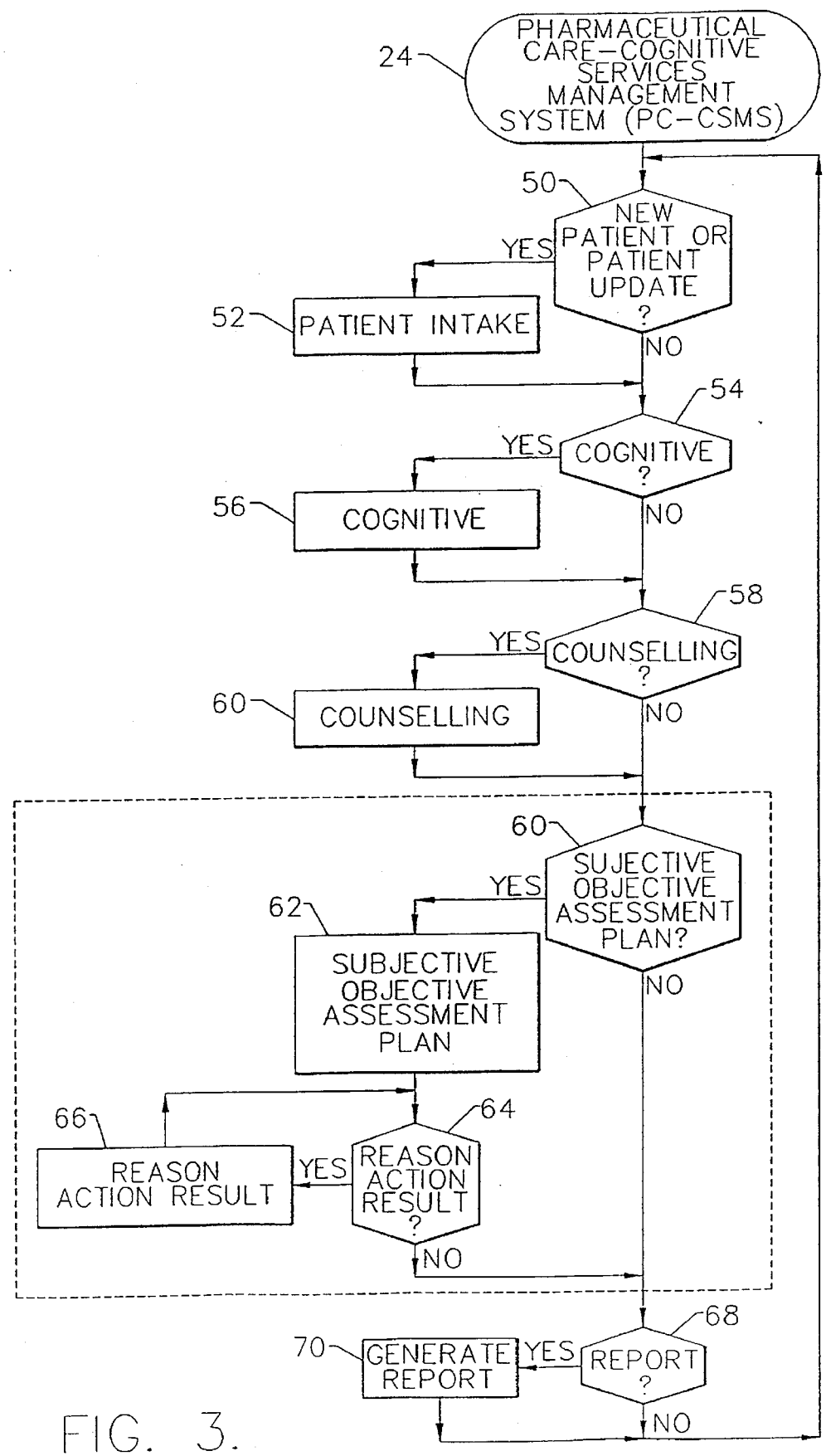
FIG. 3 is a flowchart illustrating the operational control of the pharmaceutical care cognitive services management system illustrated in FIG. 2.

Referring to FIG. 3, a high level control flowchart of PC-CSMS 24 will now be described. The flowchart in FIG. 3 provides the flow control resulting from use of PC-CSMS 24. It will be understood by those having skill in the art that flowcharts may be implemented by computer system 12. PC-CSMS 24 is event controlled, and thus, processing can begin at essentially any of patient intake subsystem 26, cognitive subsystem 28, counseling subsystem 30, SOAP subsystem 32, RAR subsystem 34 or report generation subsystem 38. The following description, however, assumes that processing is begun with patient intake subsystem 26.

A determination is made at 50 whether a new patient is to be processed or a patient record is to be updated. If a new patient is to be entered into PC-CSMS 24 or a patient record is to be updated, patient intake subsystem is invoked at 52 and the new patient information or the updated patient information is collected and stored, i.e., the records are either generated or updated in data storage device 16. If neither a new patient is to be added to PC-CSMS 24 or a patient record is to be updated, a determination is made at 54 as to whether the user is initiating the cognitive subsystem. If the user is initialing the cognitive subsystem, PC-CSMS 24 then proceeds with controlling the cognitive subsystem at 56 by prompting, receiving input, storing the input and displaying encounter review information, standard of care information, therapy review information and patient summary information. If it is determined at 54 that the cognitive subsystem was not invoked by the user, a determination is made at 58 as to whether the counseling subsystem was invoked by the user. If the counseling subsystem was invoked by the user, PC-CSMS 24 then controls the counseling subsystem at 59. As a result, PC-CSMS 24 controls the counseling session by interactively prompting for user entry of information, receiving information entered by the user, storing this information and displaying information to enable therapy management, standard of care, encounter management, and patient summary processes to be performed.

If it is determined at 58 that a counseling session was not initiated by the user, a determination is made at 60 as to whether the user has decided to create or update a SOAP (i.e., Subjective, Objective, Assessment and Plan). If it is determined at 60 that the user has initiated a request to create or update a SOAP, PC-CSMS 24 then controls the creation or updating of the SOAP at 62. As a result, PC-CSMS 24 prompts for, receives and stores subjective and objective information relating to the patient and a particular drug, an assessment of the relationship between the subjective and objective information, and a plan to be followed as a result of the generated assessment. Once the SOAP subsystem is completed at 62, a determination is made at 64 as to whether the user requested the creation or update of a RAR (i.e., Reason, Action, Result). If the user requested creation or update of a RAR, PC-CSMS 24 controls the creation or updating of a RAR at 66 by prompting the user and receiving information from the user relating to the reason for the SOAP, an action taken by the user based on the SOAP, and the result of the action. Once the RAR is completed, a determination is made as to whether the user desires to create or update a second RAR associated with the same SOAP. If so, PC-CSMS 24 creates a second SOAP at 66 associated with the same SOAP as the previously created RAR. Thus, the user may create multiple RARs associated with a single SOAP.

If either a determination is made at 60 that a SOAP is not to be created or at 64 that a RAR is not to be created, PC-CSMS 24 makes a determination at 68 as to whether a report is to be generated. If a determination is made at 68 that a report is to be generated, PC-CSMS 24 generates the report at 70. If a report is not to be generated or a report is generated and processing of the report is complete, control is returned to block 50 to determine which of the processes of the pharmaceutical care cognitive services management system 24 are to be invoked. Since PC-CSMS 24 is an event implemented system, it will be understood by those having skill in the art that control can be transferred to any one of the patient intake subsystem 26, cognitive subsystem 28, counseling subsystem 30, SOAP subsystem 32, or report generation subsystem 38 at any point.

Finally, it will also be understood by those skilled in the art that the interrupt subsystem 36 (see FIG. 2) can be implemented at any point during processing by the cognitive subsystem 28 or the counseling subsystem 30.

Conceptual and Physical Data Models

Figure 4A:
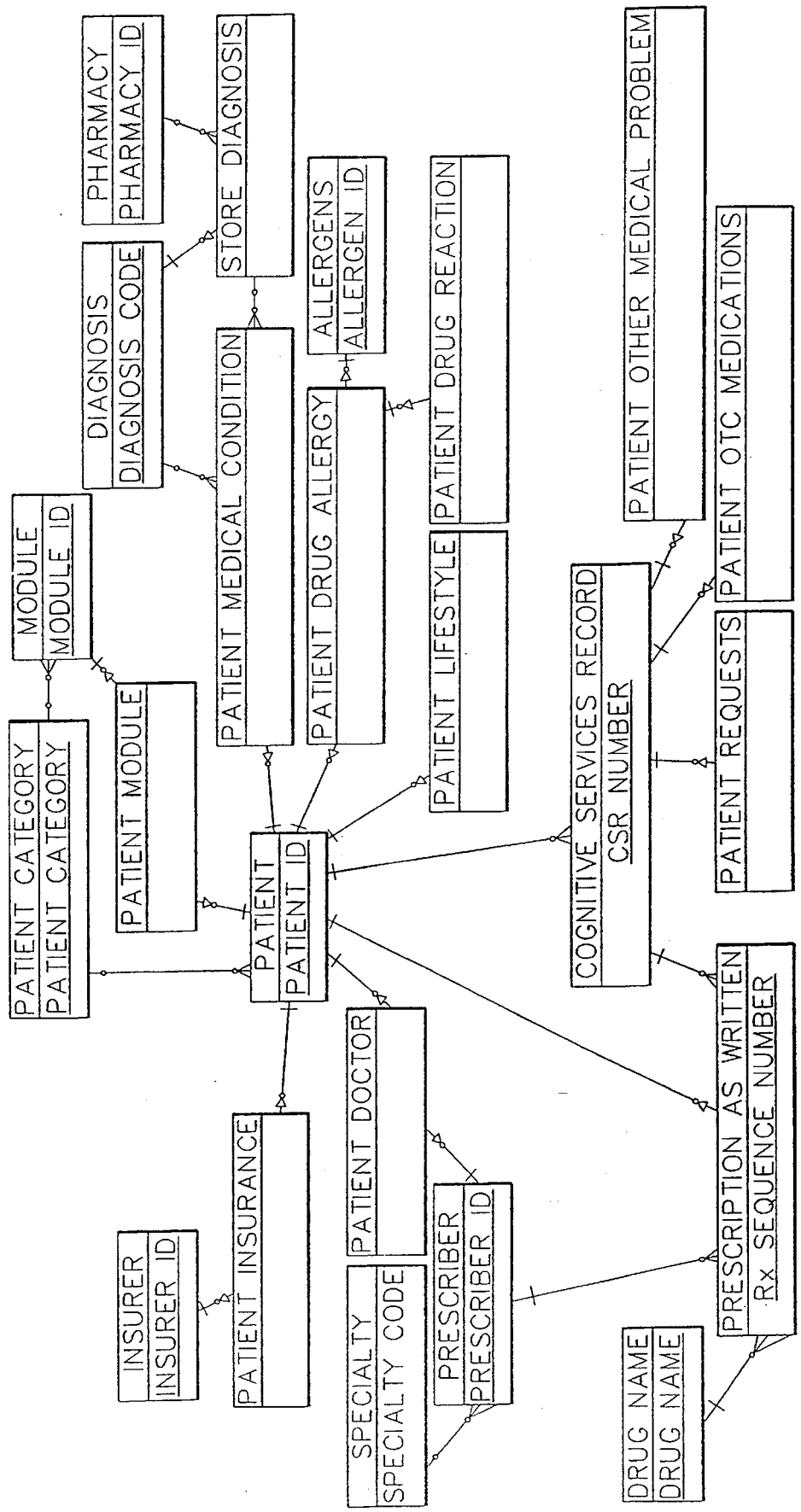
FIGS. 4A through 4C are conceptual data models for the present invention.
Figure 4B:
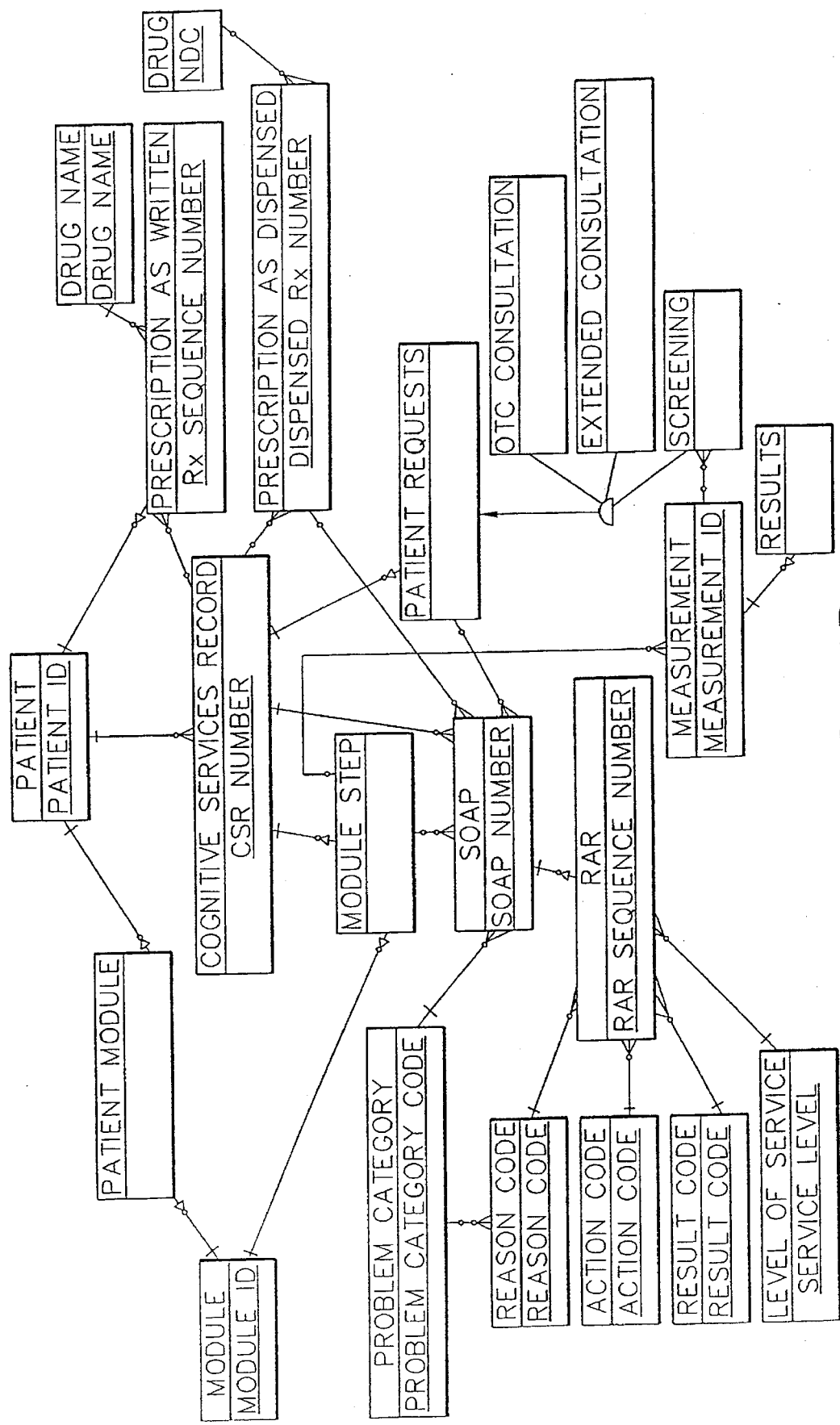
Figure 4C:
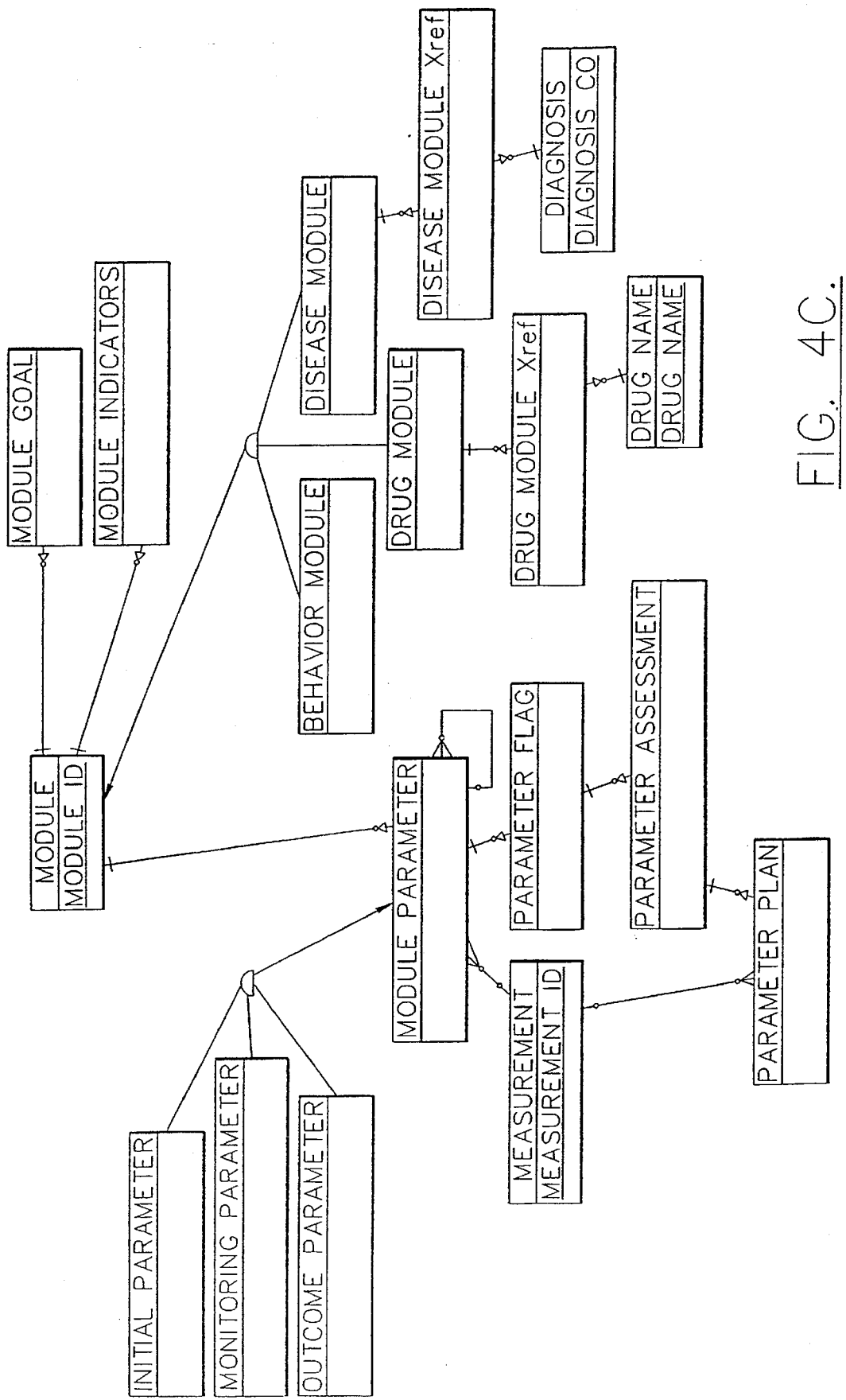
Figure 4D:
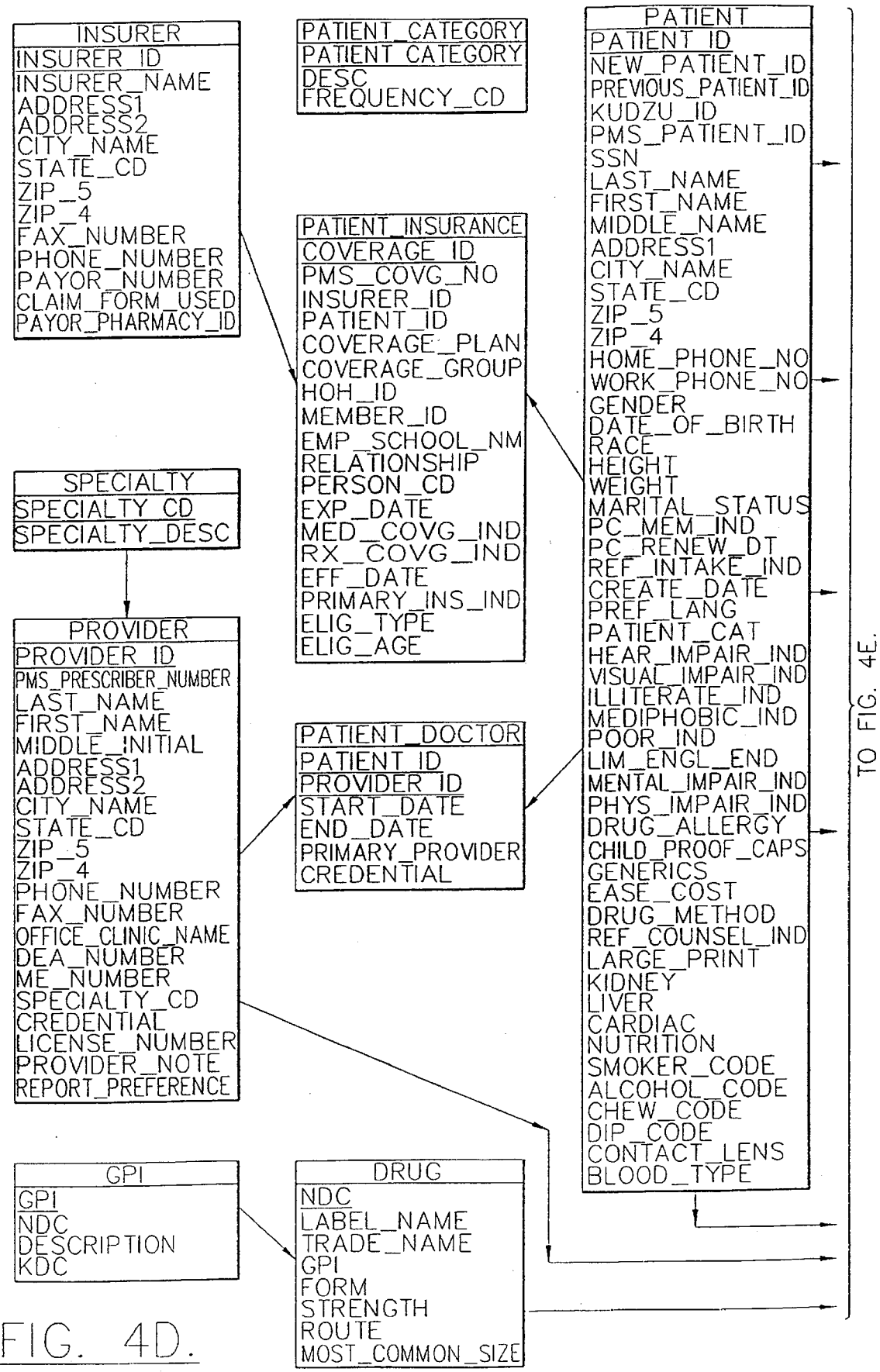
FIGS. 4D through 4H are physical data models for the present invention.
Figure 4E:
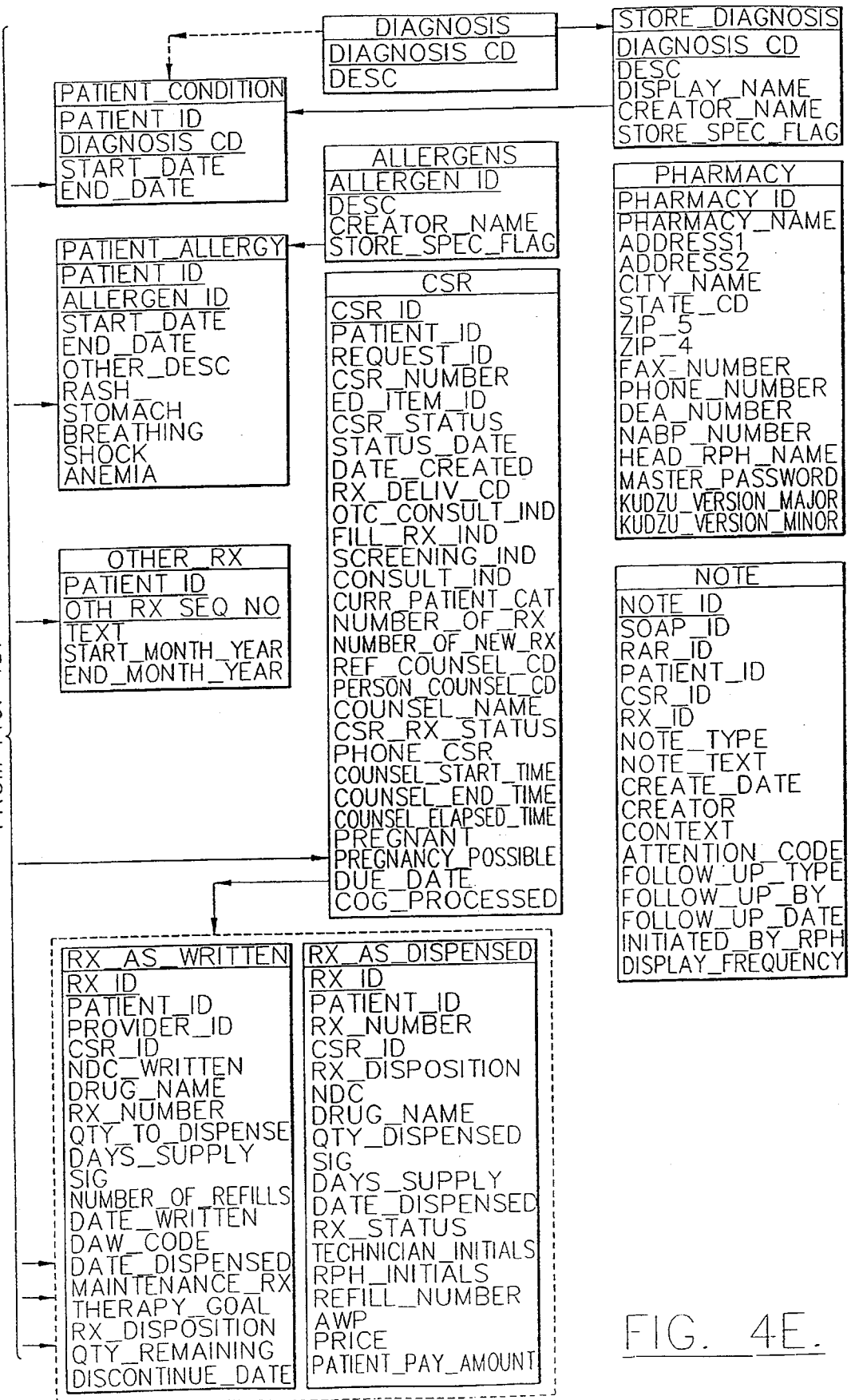
Figure 4F:
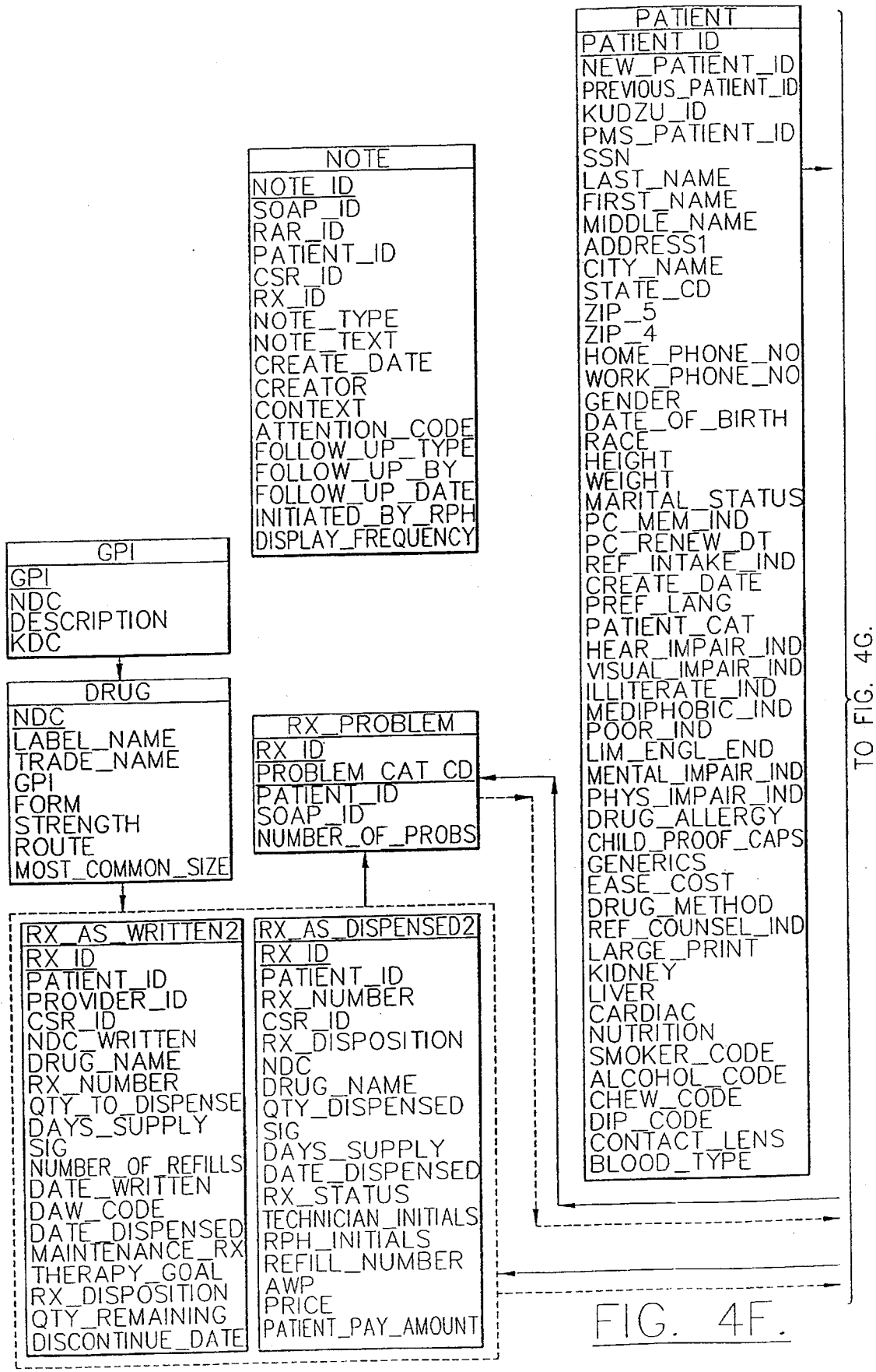
Figure 4G:
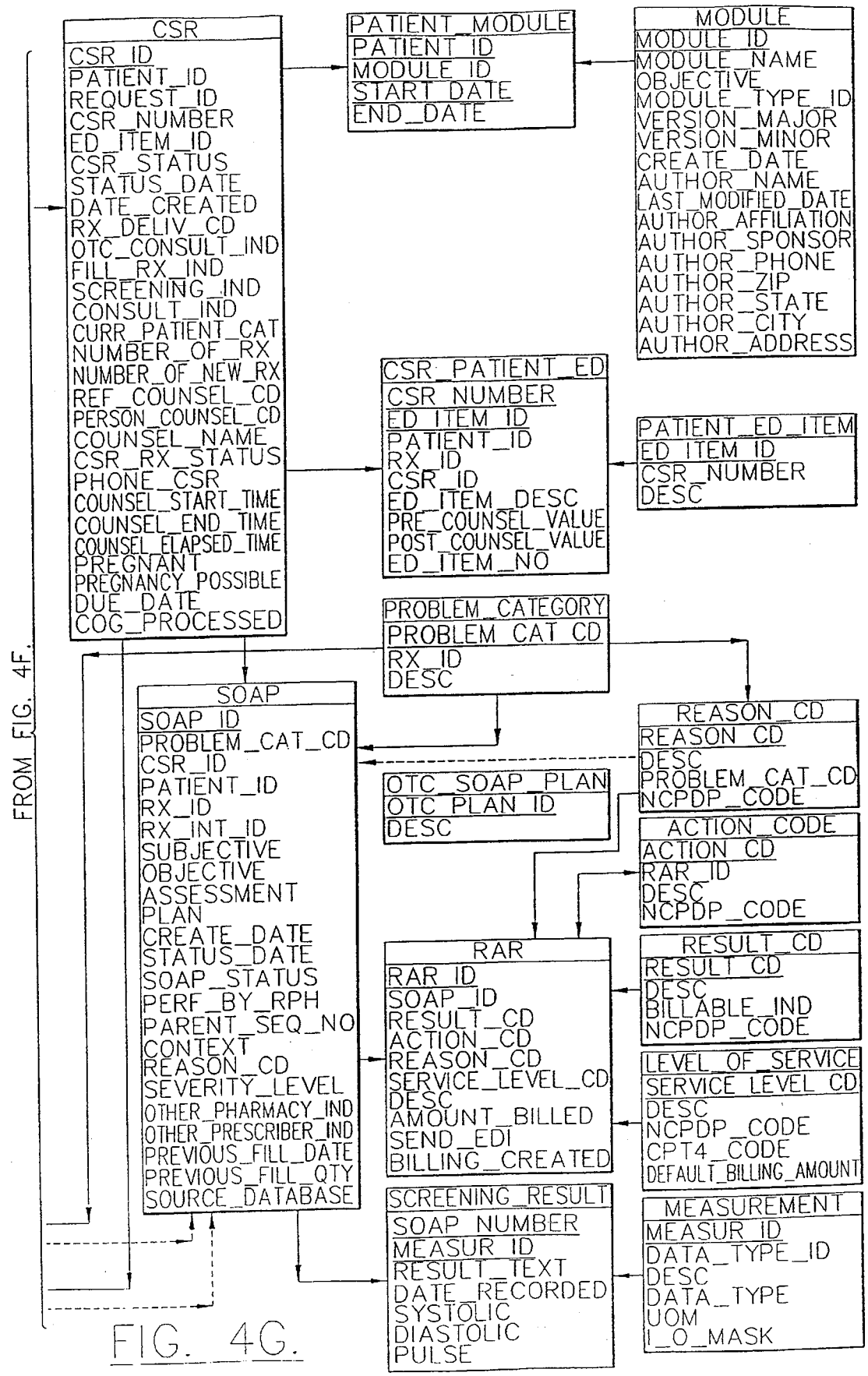
Figure 4H:
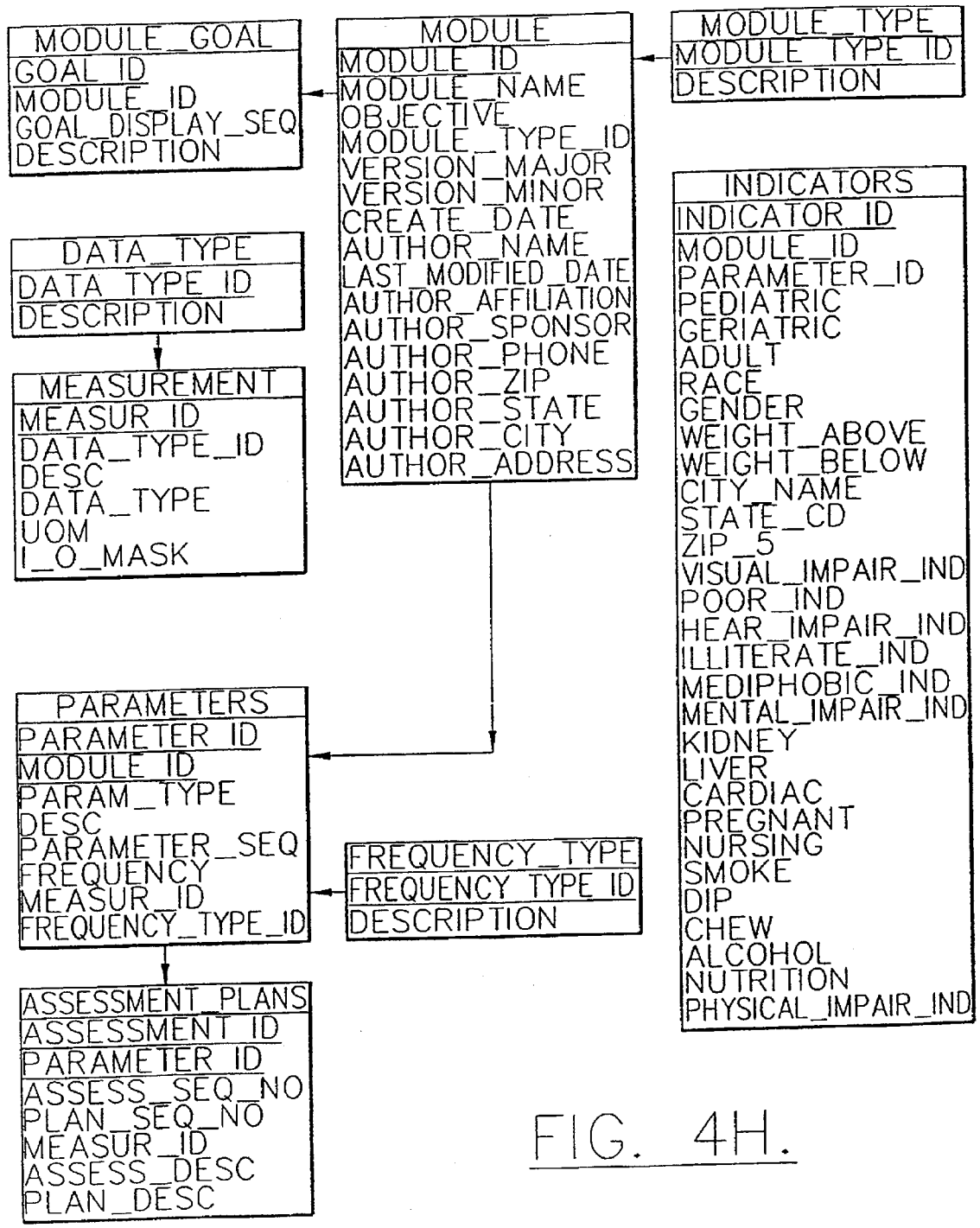

Referring to FIGS. 4A–4H, the design for the data flow and relationships in the pharmaceutical care cognitive services management system will be described. In particular, conceptual data models for PC-CSMS 24 are illustrated in FIGS. 4A–4C and physical data models for PC-CSMS 24 are illustrated in FIGS. 4D–4H. The conceptual data models illustrated in FIGS. 4A–4C illustrate the entities, attributes, data items, relationships, inheritances and domains according to the pharmaceutical care cognitive services management system. The physical data models illustrated in FIGS. 4D–4H specify the physical implementation of the database, including tables, columns (primary and foreign keys), indexes, references and referential integrity of the pharmaceutical care cognitive services management system. The graphical technique used to illustrate the design for the conceptual data model and the physical data model will be understood by those skilled in the art. The graphical technique may be implemented using a design tool referred to as "S-Designor Corporate" which is available from SDP Technologies, Inc. of Westchester, Ill. The graphical technique for understanding the conceptual data models and physical data models is described in detail in the publicly available Corporate User's Guide, SDP Technologies, Inc., 1993, Part 1, pages 11–33, the disclosure of which is hereby incorporated herein by reference.

Figure 48:
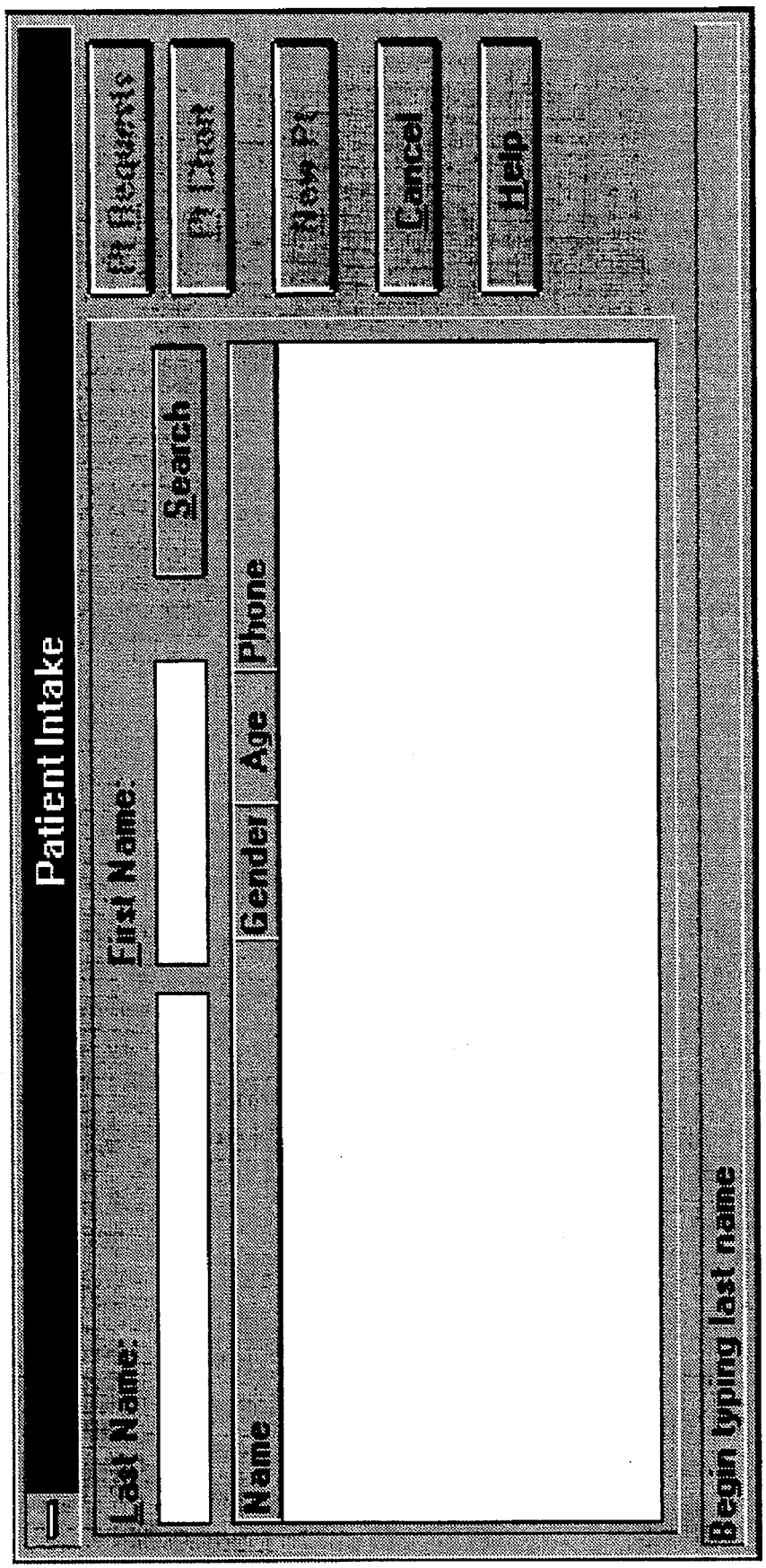
Figure 49:
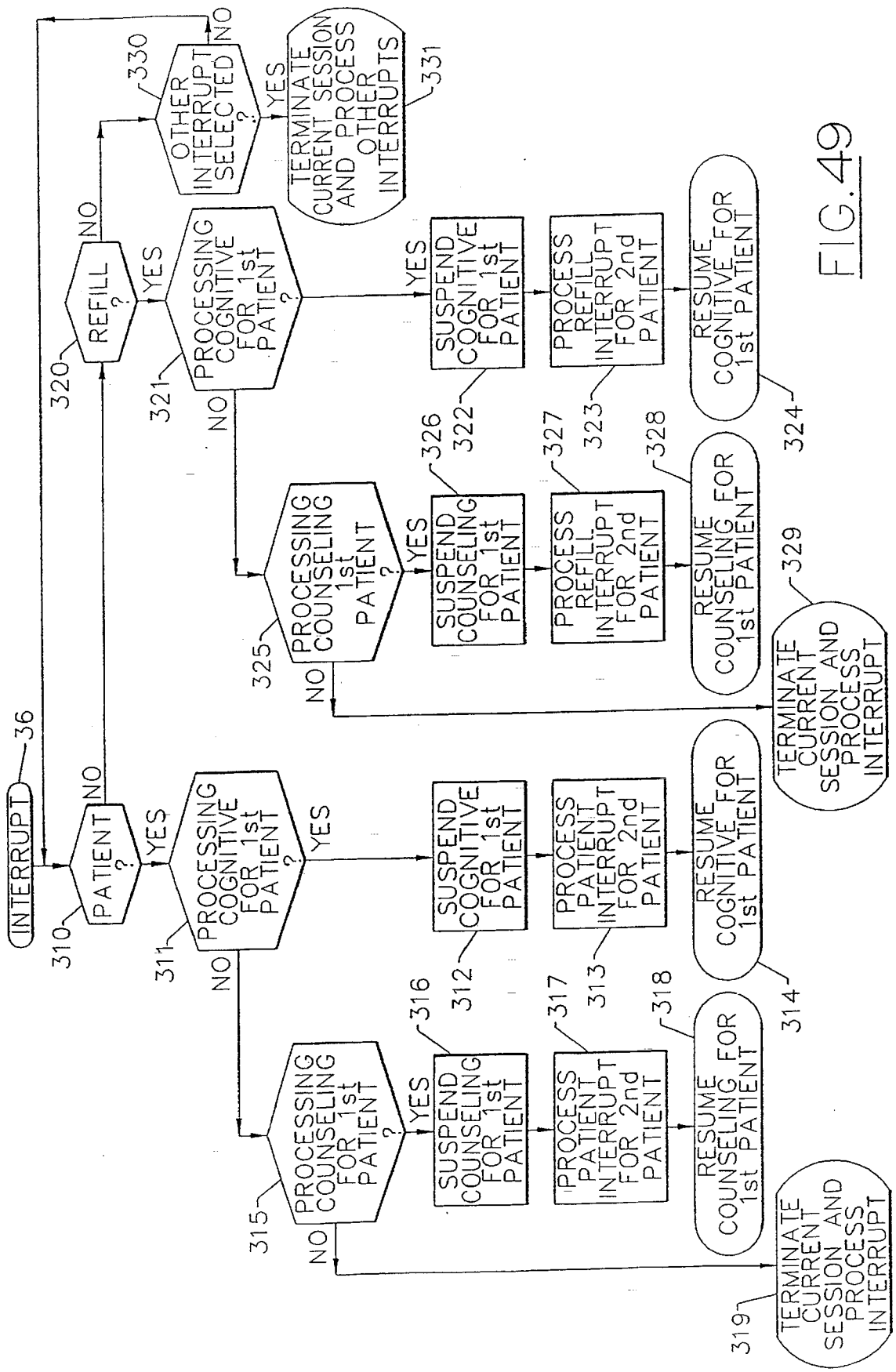
FIG. 49 is a flowchart illustrating the operational control of the patient and refill interrupts.
Figure 50:
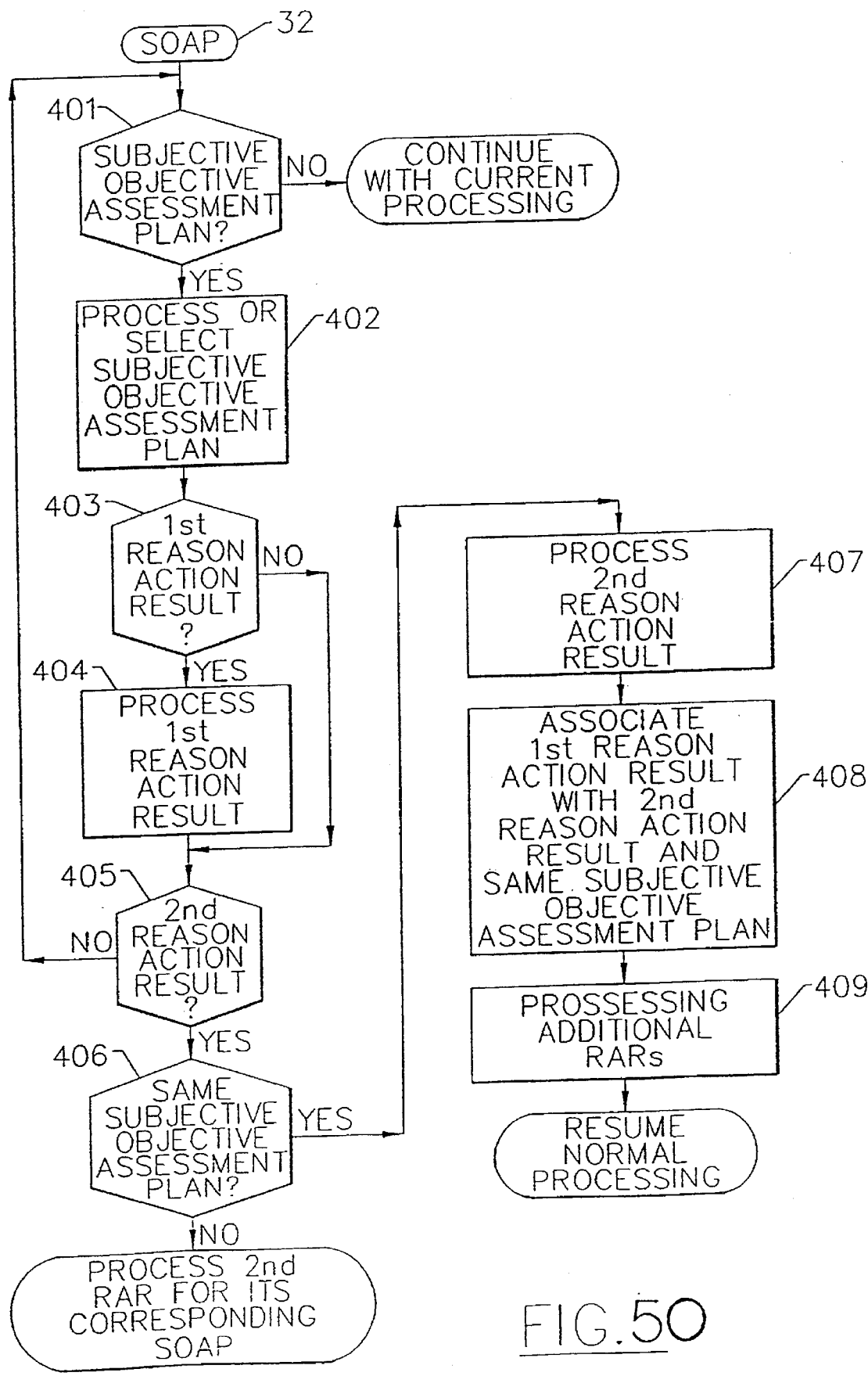
FIG. 50 is a flowchart illustrating the operational control of the operation of processing a single SOAP and multiple RARs associated therewith.

Detailed Operation of Pharmaceutical Care Cognitive Services Management System The sequence of operations performed by the pharmaceutical care cognitive services management system will now be described in detail with reference to screen interfaces illustrated in FIGS. 5–48. In addition, the flowcharts in FIGS. 49 and 50 provide the flow control resulting from implementation of multiple RARs associated with a single SOAP and the patient and refill interrupt subsystems, respectively. It will be understood by those having skill in the art that the screen interfaces of FIGS. 5–48 illustrate the operational control flow of the PC-CSMS 24 which is implemented using event programming techniques rather than sequential programming. It will also be understood by those having skill in the art that the operational flow defined by the screen interfaces and their sequence, may be implemented by computer system 12, operating under stored program control. The displays illustrated in FIGS. 5–48 are examples of displays which appear on display device 20 at various times during use of the PC-CSMS 24. Selection of options displayed on display device 20 may be made by a user using any input device including a keyboard, a mouse, a virtual track ball, a light pen or even a touch screen interface, individually or collectively. The system responds according to the selection made by the user.

Generally, during use of PC-CSMS 24, a user can implement any of the subsystems from any point. For example, while in the patient intake subsystem (i.e., patient chart or cognitive service record), a user may decide to terminate processing by the patient intake subsystem and begin processing by the cognitive subsystem or counseling subsystem. Operational flow of the pharmaceutical care cognitive services management system will now be described with reference to FIGS. 5–48.

Detailed Operation: Work Order Subsystem

Figure 5:
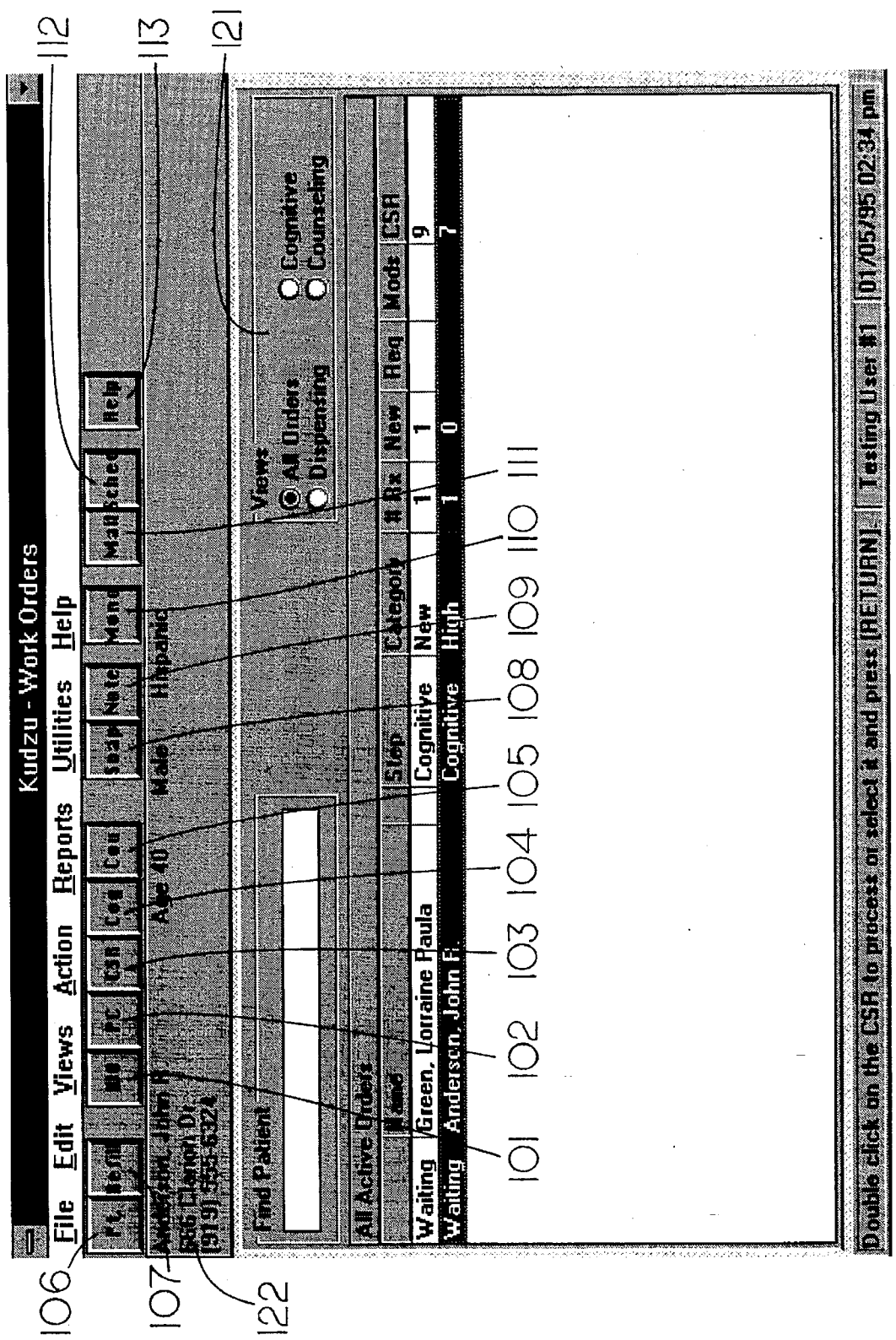

Referring to FIG. 5, the list of work orders to be processed by the user or pharmacist is displayed. The list of work orders, which is always the first screen interface to be displayed to the user, may be accessed at any point during use of PC-CSMS by selecting the "WO" key or button 101 on the display screen. "Keys" may also be referred to as "buttons." The list of work orders displays all active orders in the system. A variety of information is displayed with respect to each patient including the status of the prescription (e.g., waiting, pick up or delivery), the name of the patient, the status of the processing of the drug order (e.g., in process ("IP") or suspended ("S")), the step of the pharmacy management or health care being provided (e.g., "Cognitive," "Counseling" or "Reporting"), and the category of the patient (e.g., "Low" which means a basically healthy person, "High" which means a patient has some problems which may be chronic, or "Special" which refers to anything that the user wants to specifically note). Additional information is also displayed with respect to each patient in the list of work orders including the number of prescriptions to be filled, how many, if any, of the prescriptions to be filled are new prescriptions, what type of patient requests are to be performed, the number of modules and module steps to be performed, and the cognitive service record number of the current patient encounter.

Still further, different views may be displayed of the work order. Options for displaying different views of the work order are displayed at 121 which permit the user to display all orders, orders being dispensed, orders presently being processed by the cognitive subsystem, or orders which require processing by the counseling subsystem. Finally, the user can find a patient quickly by entering a user's name in the "Find Patient" field and the PC-CSMS will locate the patient in the list of the patients presently being viewed, highlight the patient located in the list of patients, and provide additional personal information relating to the patient at 122.

As previously mentioned, after the work order is viewed and a patient is selected, the user may move to any of the other subsystems of PC-CSMS by selecting any of the other keys or buttons on the display screen, including the patient chart ("PC") at 102, cognitive service record ("CSR") at 103, cognitive subsystem ("COG") at 104, counseling subsystem ("COU") at 105, patient interrupt subsystem ("Pt.") at 106, refill interrupt subsystem ("Refill") at 107, SOAP subsystem at 108, Note subsystem at 109 or Mono (i.e., Drug Monograph) subsystem at 110. The user may also use electronic mail by selecting the "Mail" key or button at 111, use the scheduler by selecting the "Sched" key or button at 112 or use online assistance by selecting the "Help" key or button at 113.

Detailed Operation: Patient Intake Subsystem

The detailed operation of the patient intake subsystem will now be described. The patient intake subsystem includes two components, i.e., patient chart and cognitive service record. The patient chart component is generally only accessed by the user if a new patient is to be processed, and thus patient identification and history information must be entered into PC-CSMS, or if the patient identification and history information relating to a particular patient requires updating.

Figure 6:
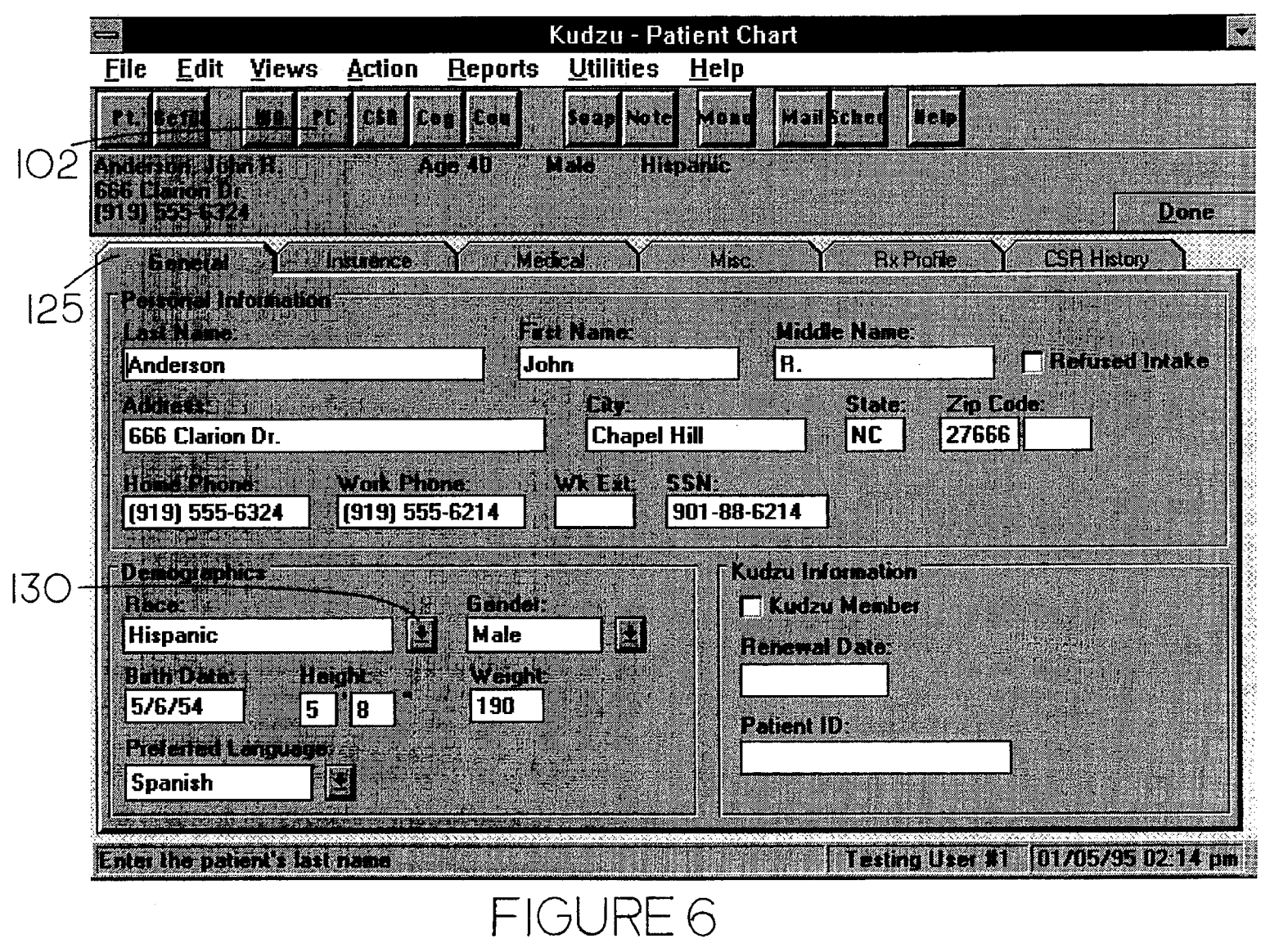

Referring to FIGS. 6–11, the patient chart component includes six "tabs" (at 125, generally) or parts relating to general patient identification information, insurance, medical history, miscellaneous, drug profile information, and CSR (i.e., Cognitive Service Record) history information. The user may move between any "tab" or part by "clicking" on the desired tab or using any other input device for selecting options. While in the general mode for patient chart as illustrated in FIG. 6, the user is prompted on display device 20 to enter general information relating to the new patient including name, social security number, address, telephone numbers, demographics, the preferred language of the patient, an assigned patient identification number and so forth. The information is entered at input device 18 by the user. In some cases, PC-CSMS 24 provides the user with a list of information from which to choose or select data by selecting the "↓" key adjacent to the particular category. For example, "↓" at 130 adjacent to the "Race" field will display a list of different races from which the user can select. Similar "↓" keys are adjacent to the "Gender" field as well as the "Preferred Language" field indicating that the user can select the gender and preferred language from a predefined list.

Figure 7:
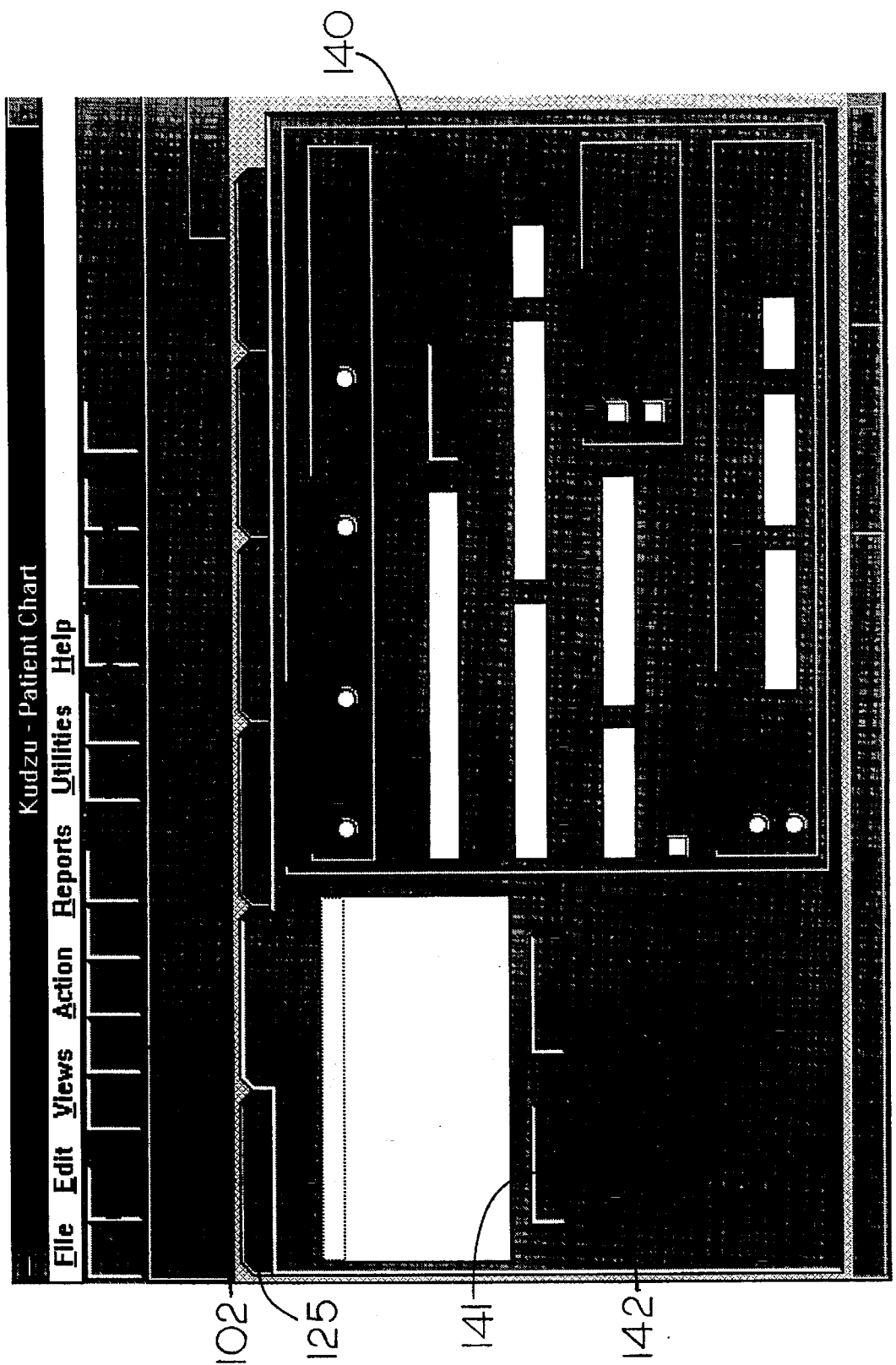

Referring to FIG. 7, the user is prompted to enter information relating to the patient's insurance by displaying a screen similar to that illustrated in FIG. 7 on display device 20. As will be understood by those skilled in the art, a payer and information related to a patient's insurance for the particular payer, can be added by selecting "Add" key or button 141 to add a payer which to the list of patient payers. Information which may now be entered by the user at input device 18 relating to the patient's insurance for the particular payer includes the patient's relationship to the card holder, identification of the card holder, the patient's insurance number, plan, group, and eligibility details relating to family, individual and policy effective date. The user may find the card holder by selecting "Find" key or button 140 which allows the user to find the particular card holder by displaying the current card holders for this particular payer. In addition, any payer and related patient insurance information for the particular payer may be removed by highlighting the particular payer in the list of patient payers and selecting "Remove" key or button 142.

Figure 8:
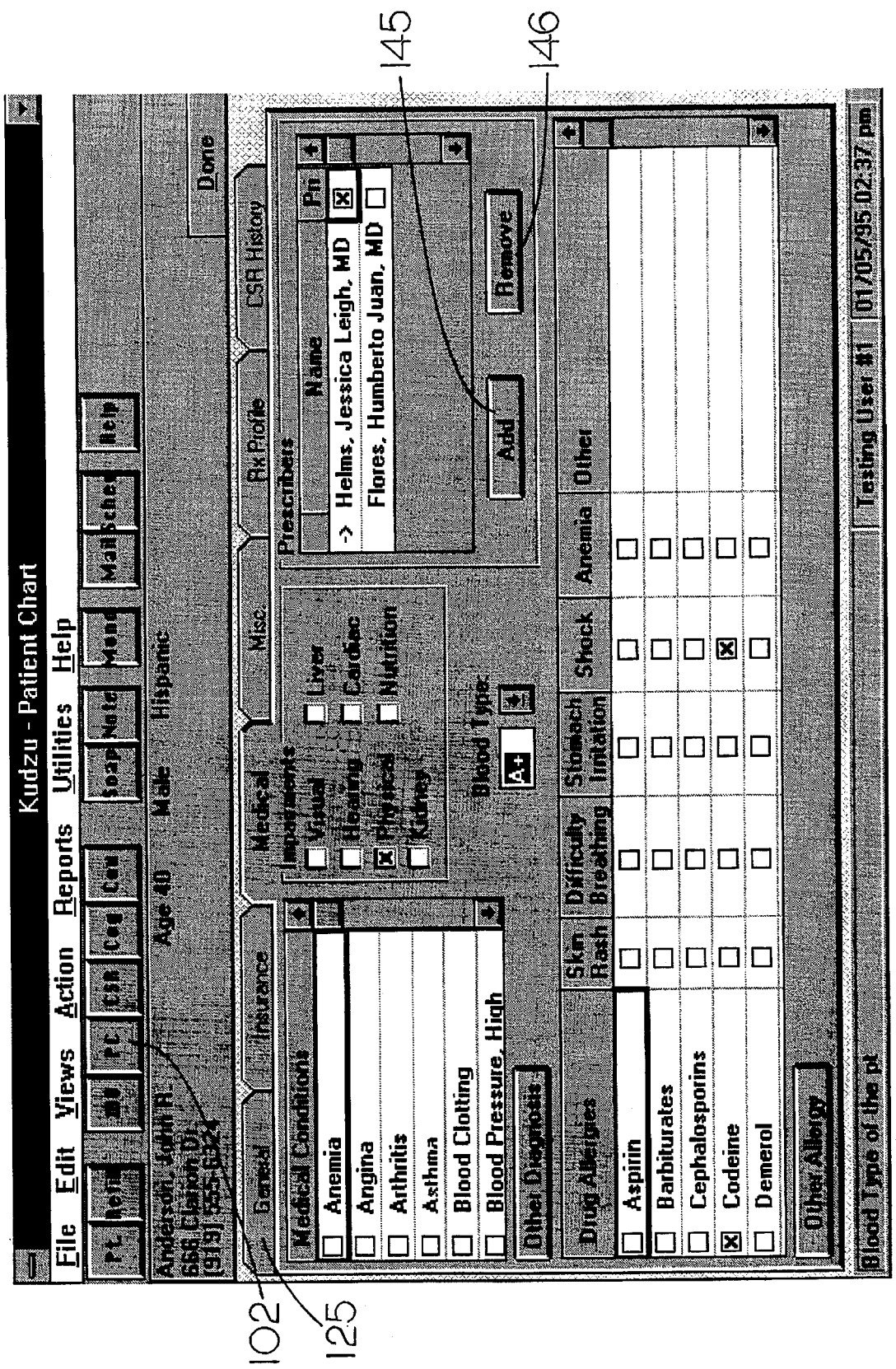
Figure 9:
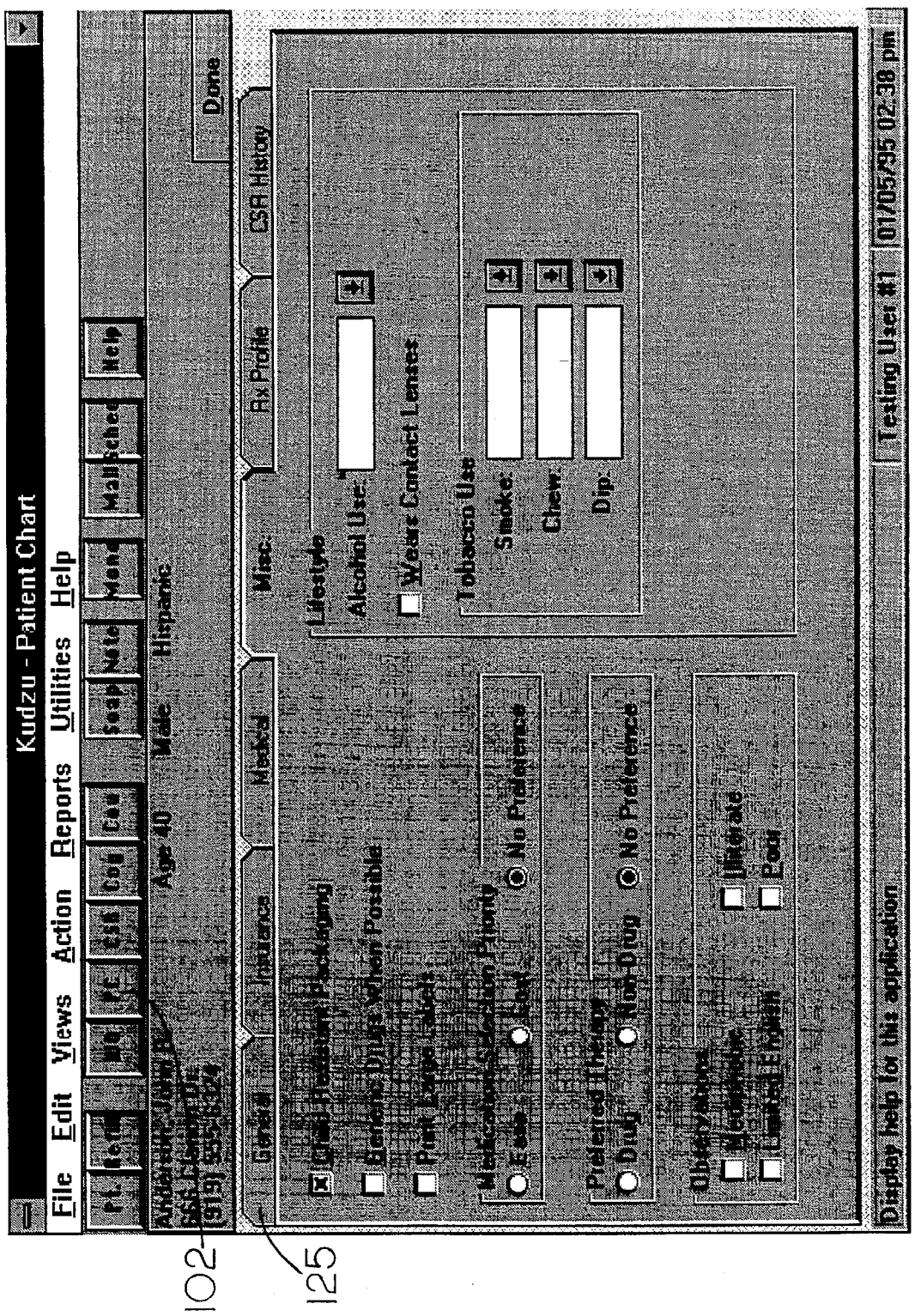

The user is also prompted during patient chart to collect or update information relating to the medical history of the patient by displaying a screen similar to that illustrated in FIG. 8. Any number of different characteristics may be displayed and collected relating to a patient. For example, information relating to drug allergies, skin rash, difficulty breathing, stomach irritation, shock, anemia, medical conditions, blood type or impairments may be noted. In addition, the patient's physician or prescriber may be listed and names of physicians or prescribers may be added to or deleted from the "prescriber" list using "Add" key 145 or "Remove" key 146, respectively. As indicated by the "↑" and "↓" keys, the drug allergies and the medical conditions may be selected by scrolling a predefined list scrolled to locate an allergy or condition located in the list.

PC-CSMS 24 also prompts the user to enter or update miscellaneous information with respect to the patient. This is accomplished by displaying a screen similar to that illustrated in FIG. 9 on display device 20 for the "Misc." tab at 125, generally, permitting the user to enter the various miscellaneous information or select the information from a predefined list. For example, miscellaneous information may include child resistant packaging, generic drugs, size of the label for ease of reading, medication selection priority, preferred therapy, pharmacist observations regarding characteristics of the patient, alcohol use, tobacco use and whether corrective lenses are used. Information relating to alcohol use and tobacco use may be selected from predefined lists as indicated by the "↓" keys.

Figure 10:
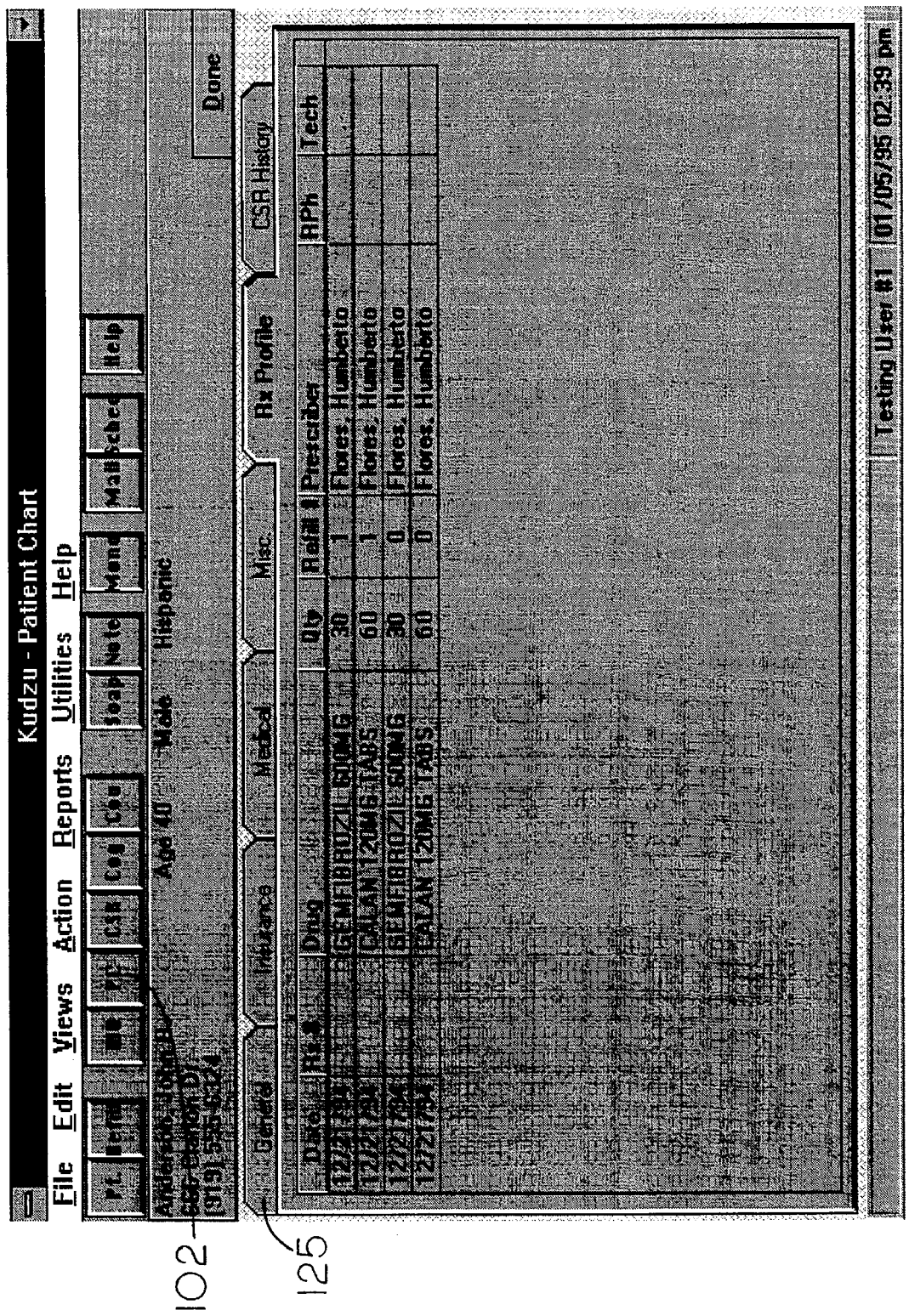

Referring to FIG. 10, patient chart also displays information to the user on display device 20 relating to the patient's prescription profile ("Rx Profile"). The information displayed to the user may include the date of a prescription, the prescription number, the name of the drug, the quantity of units of the drug, the number of refills permitted, the identification of the prescriber, and various other information relating to the profile of a particular prescription.

Figure 11:
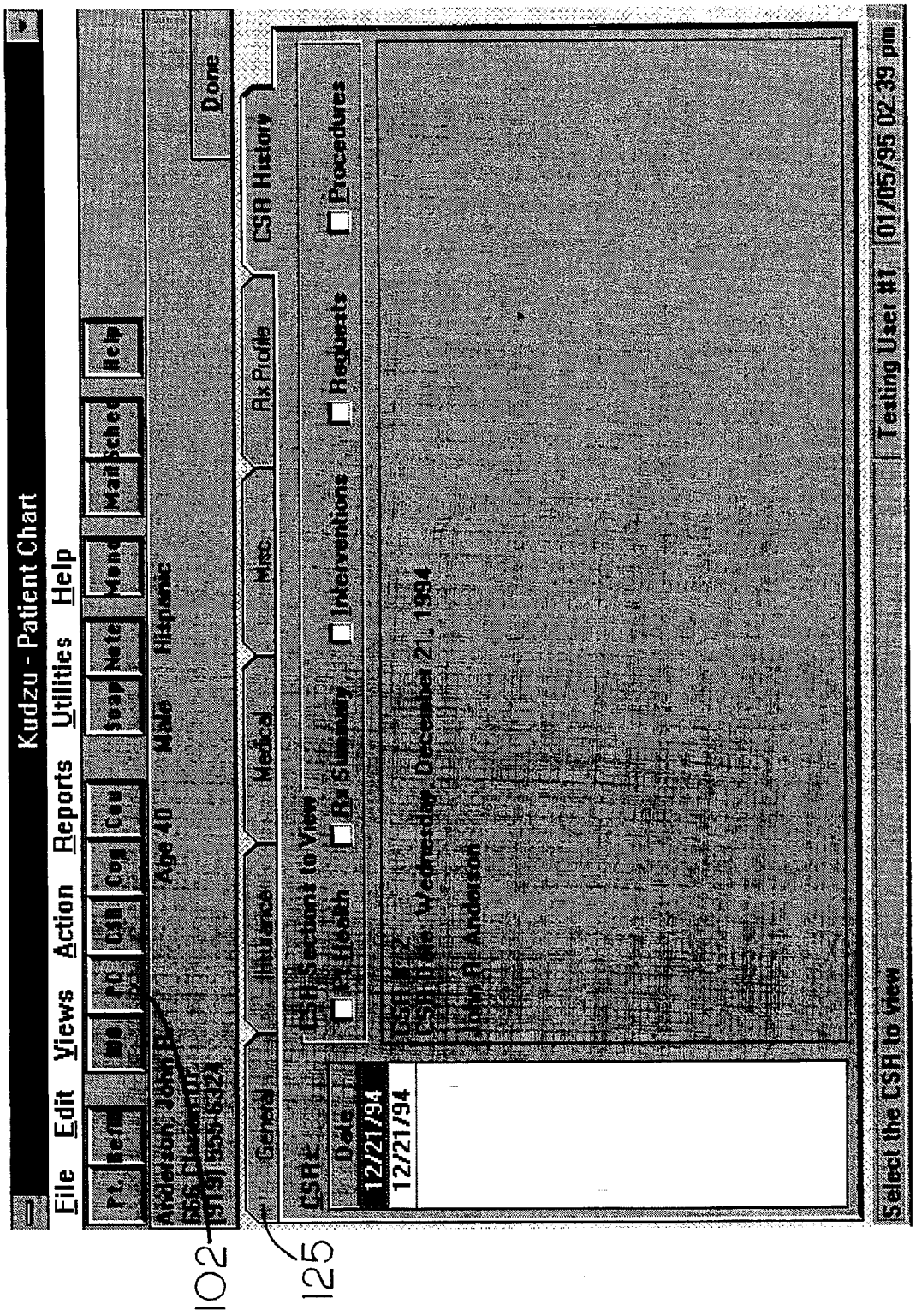

Finally, a patient chart also displays the cognitive service record history of the patient ("CSR History") by displaying a screen similar to that illustrated in FIG. 11. The information displayed to the user permits the user to enter via display device 20 the date a cognitive service record was created, and allows the user to enter or view different sections of cognitive services records including information relating to the patient's health, summary of drug use, interventions, requests and screenings.

Figure 12:
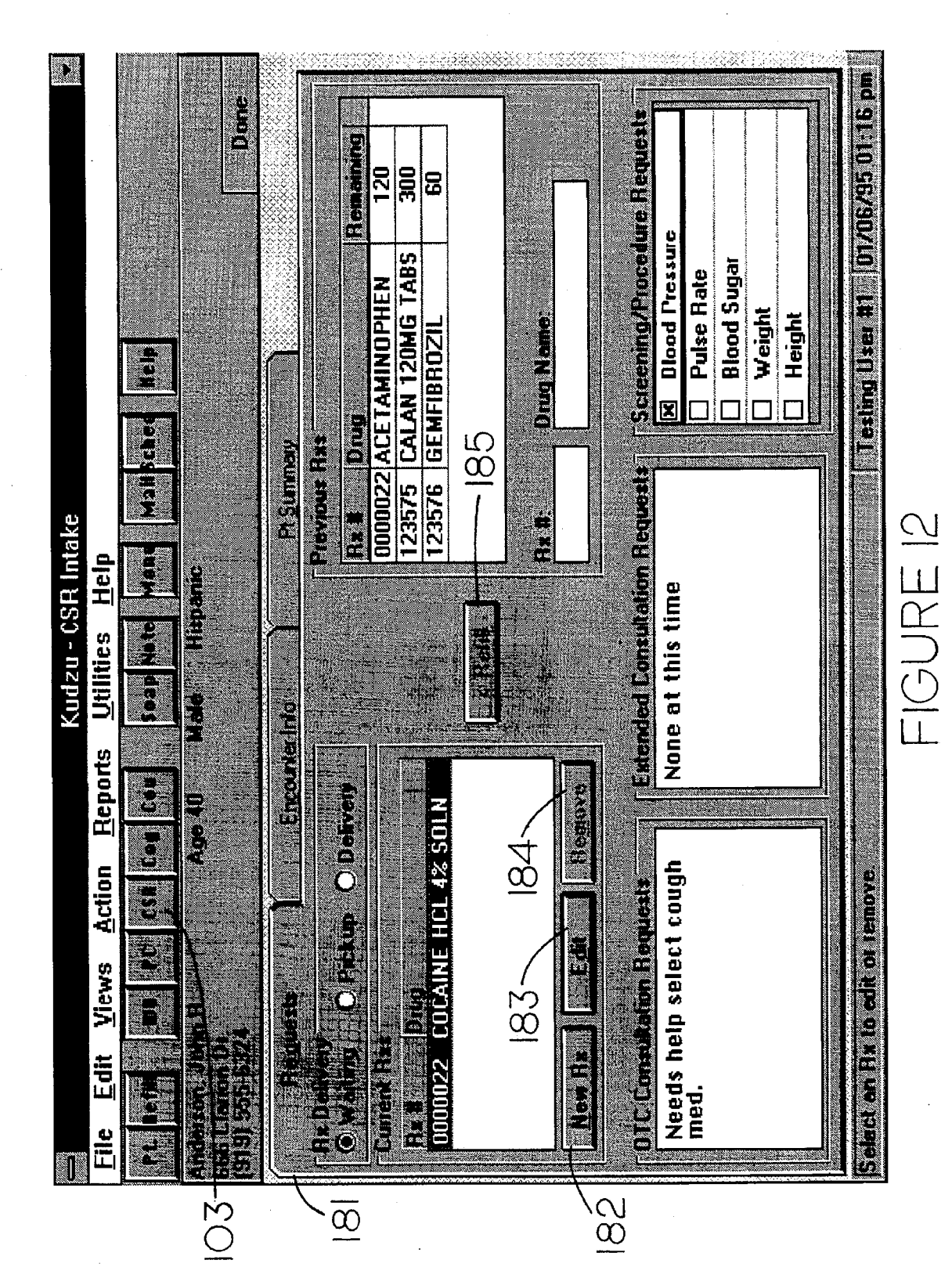
Figure 13:
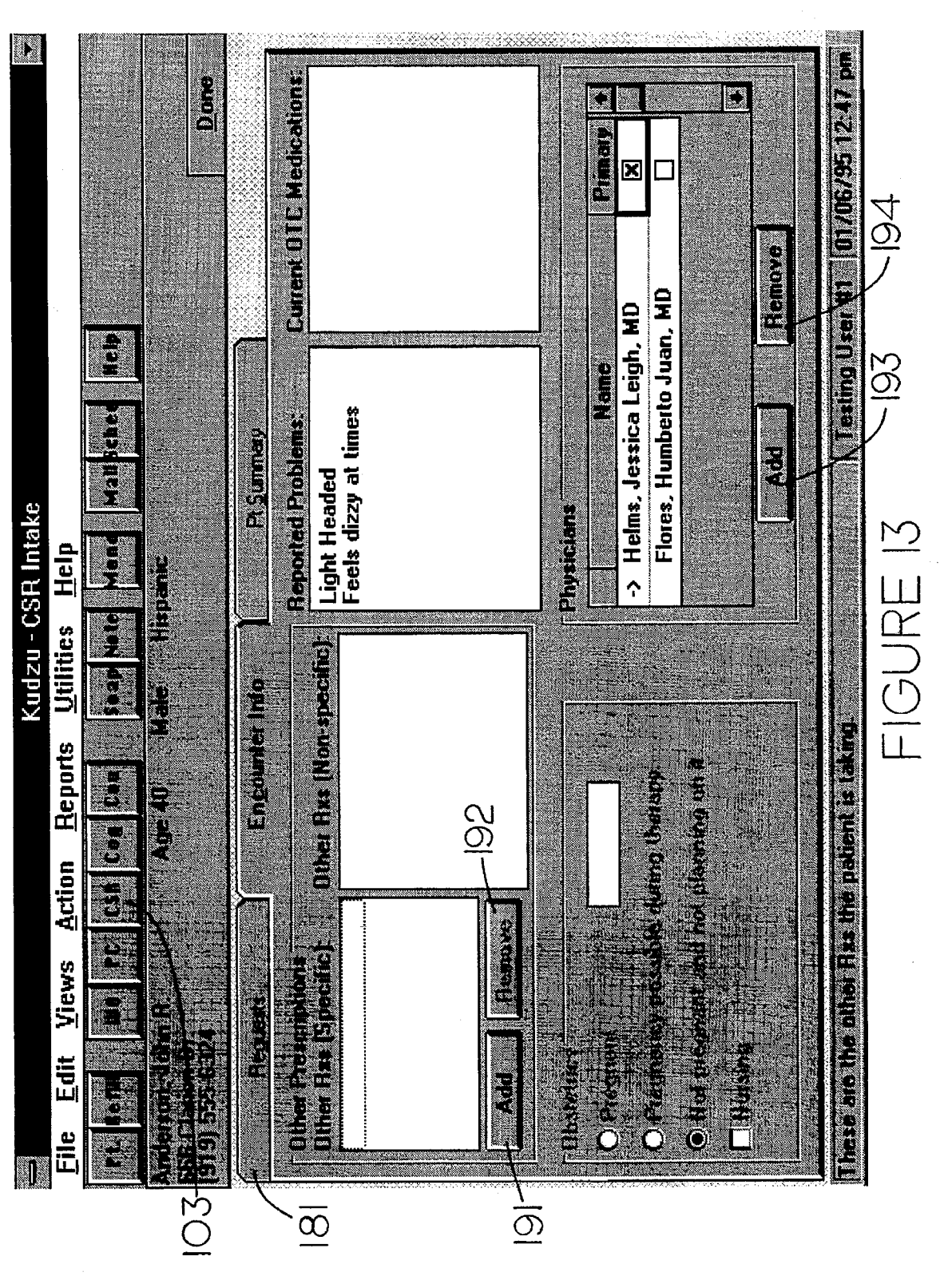
Figure 14:
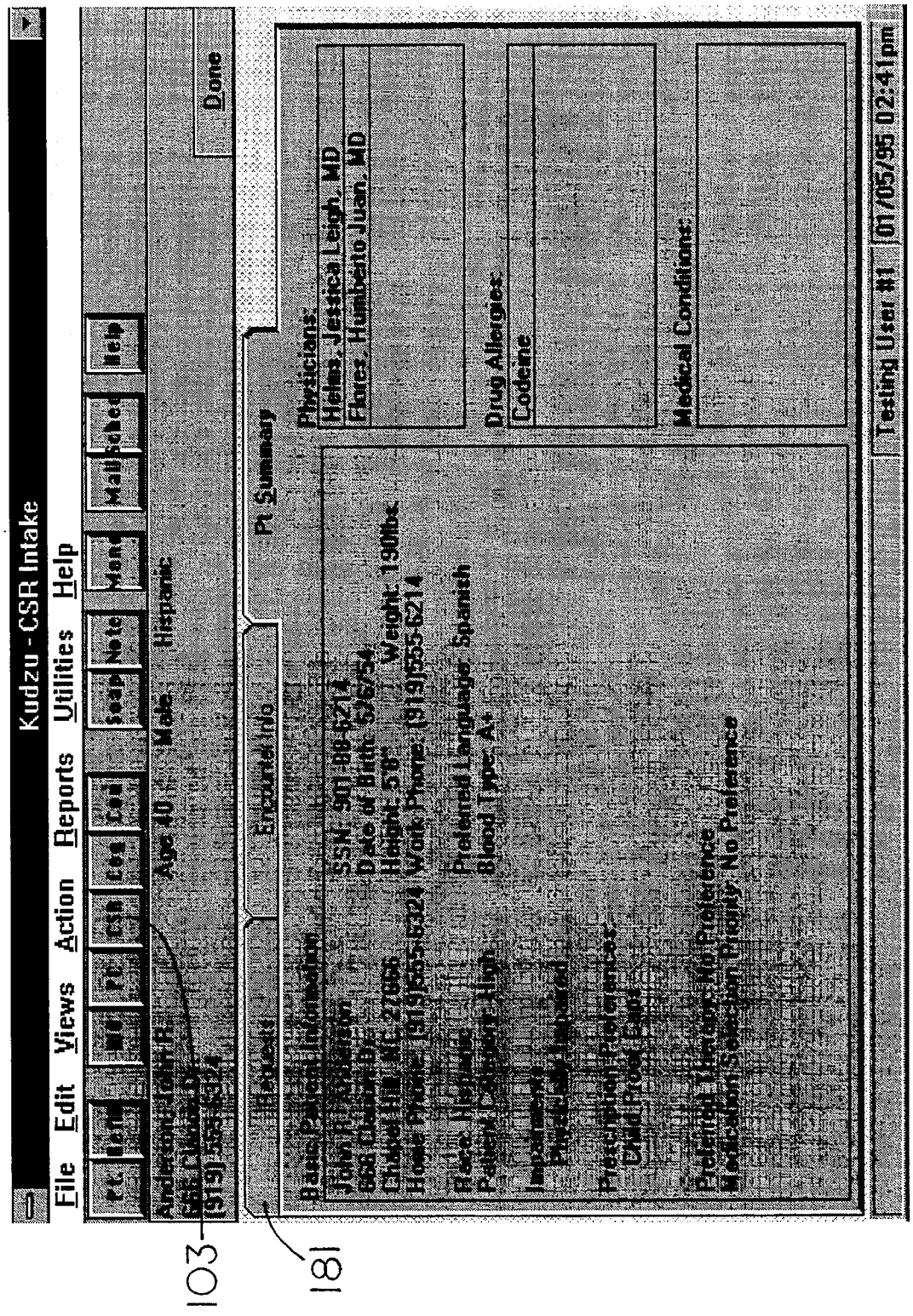

The second component of the patient intake subsystem is cognitive service record ("CSR"). Cognitive service record may be invoked by selecting "CSR" key or button 103. Referring to FIGS. 12–14, processing of the cognitive service record component will be described. Cognitive service records, as indicated by the tabs "Requests," "Encounter Info" and "Pt. Summary" at 181, generally, permit handling of requests, collection of encounter information and displaying of a summary of information relating to the patient. During requests, the user can view and survey the work to be performed with respect to a particular patient. For example, the delivery status of a drug is displayed in FIG. 12 in terms of whether the patient is waiting for the drug, the patient is going to pick up the filled prescription, or the filled prescription is to be delivered to the patient. In addition, information relating to current prescriptions is listed, and the user may add a prescription by selecting "New Rx" key 182, may edit a current prescription by selecting "Edit" key 183, or remove a current prescription by selecting "Remove" key 184. A list of previous prescriptions is also displayed to the user and the user may search this list for a particular drug by name or prescription number. In addition, the user may refill a prescription by highlighting the prescription to be refilled in the list of previous prescriptions and selecting "Refill" key 185. During processing of requests, the user can also enter over-the-counter consultation requests and extended consultation requests. Finally, the user may also enter screening requests by the patient which can be selected by the user from a predefined list.

Upon completing processing of the request portion of the cognitive service record component of the patient subsystem, the user may select encounter information processing by "clicking" on the "Encounter Info" tab at 181, generally. It will be understood by those having skill in the art that the user can move to any one of the processes within the cognitive service record component by clicking on any of the tabs "Requests," "Encounter Info" or "Pt. Summary" at any time during processing of the cognitive service record component. Similarly, the user can move to any one of the processes or tabs within each major subsystem (e.g., patient chart subsystem, counseling subsystem, etc.) by clicking on any of the tabs displayed during processing of the subsystem.

Referring to FIG. 13, processing of the encounter information with respect to the cognitive service record component will now be described. During encounter information processing, the pharmaceutical care cognitive services management system collects any additional information relating to the patient which is specific to the present encounter with the patient. For example, other prescriptions are listed. In addition, prescriptions may be added to or removed from this list by selecting the "Add" option or the "Remove" option at 191 or 192, respectively. Still further, the user can enter any obstetrics information, any specific problems reported by the patient, and any current over-the-counter medications being taken by the patient. Finally, the patient's physicians are listed, and the user can add physicians to this list or remove physicians from this list by selecting the "Add" option or the "Remove" option at 193 or 194, respectively. This list can be scrolled to permit the user to review any particular physician.

Finally, PC-CSMS displays a patient summary similar to that illustrated in FIG. 14 on display device 20 upon selection of the "Pt. Summary" tab at 181, generally. The patient summary displayed to the user displays basic patient information collected during patient chart and cognitive service record components of the patient intake subsystem, as well as a list of the patient's physicians, allergies and medical conditions. This patient summary gives the pharmacist a quick summary of the patient information and ready access to important information already requested by PC-CSMS, entered by the user and stored by PC-CSMS.

Detailed Operation: Cognitive Processing Subsystem

Referring to FIGS. 15-18, the cognitive subsystem will now be described in detail. Similar to the patient chart and cognitive service report components of the patient intake subsystem, the cognitive subsystem may be invoked by selecting the "COG" key 104. Generally, PC-CSMS 24 processes the drug regimen prior to using the cognitive subsystem. A DUR is performed in order to determine if there is anything unique about this drug, this particular patient, the particular disease, the quantities of the drug and so forth which may result in an adverse reaction of the patient to the drug. The patient does not need to be present during processing by the cognitive subsystem. Part of DUR is automatic in that PC-CSMS 24 compares the identified drug with the information in a drug database to identify side effects of the drug and any interactions that may occur as a result of this particular patient using the identified drug. The result of the comparison is utilized during the therapy review portion of cognitive processing. While the patient intake subsystem (i.e., patient chart and cognitive service record) may be used by a technician, the user of PC-CSMS during cognitive processing must be a pharmacist. Generally, the cognitive subsystem has four parts as indicated by the four tabs generally at 211 in FIGS. 15-18 (i.e., "Encounter Review", "Standard of Care", "Therapy Review" and "Pt. Summary"). Encounter review, standard of care, therapy review or patient summary may be invoked by the user at any time during cognitive processing by selecting one of the tabs at 211.

Figure 15:
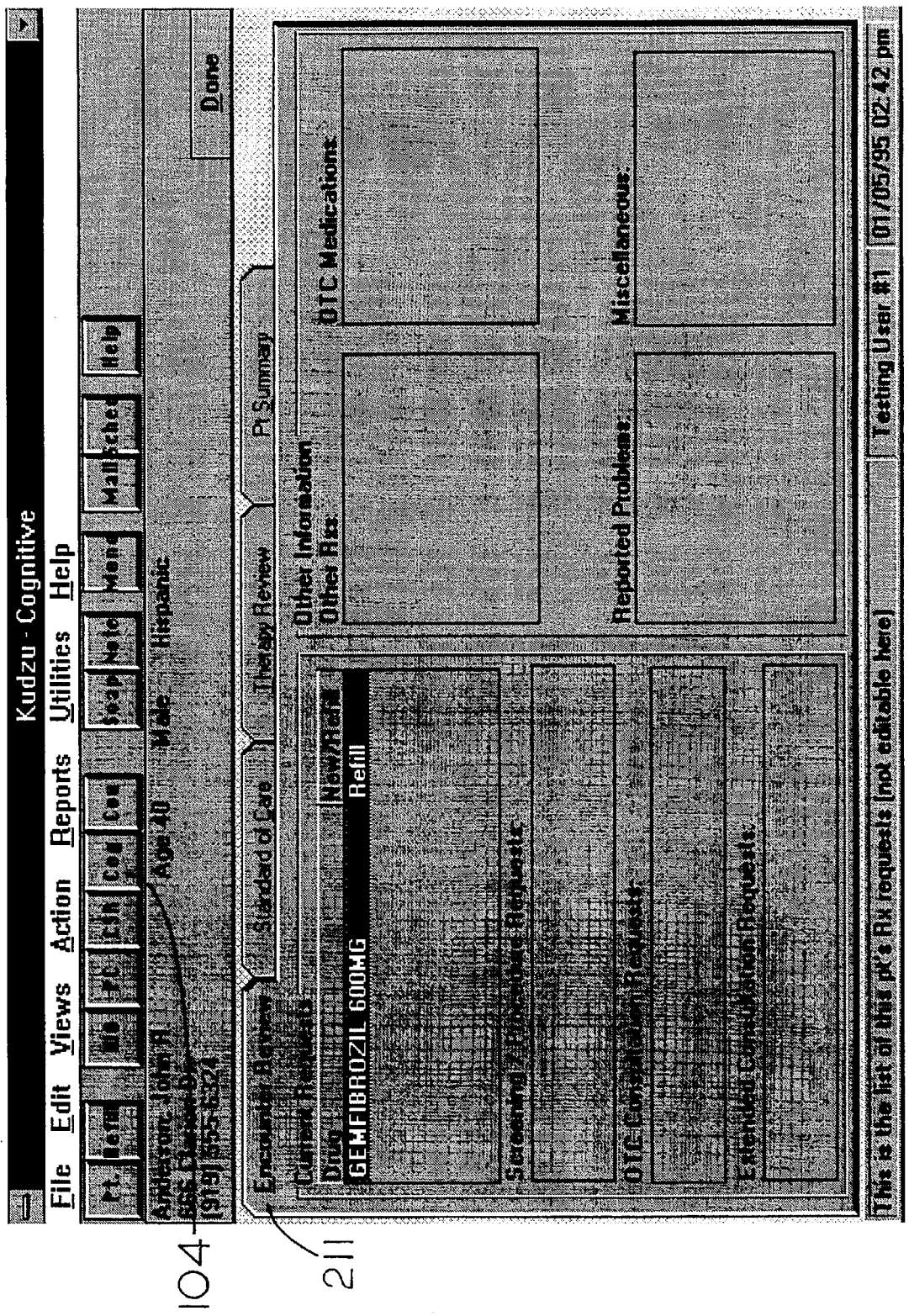

During encounter review, PC-CSMS 24 displays a summary of information relating to the particular encounter with the particular patient on display device 20. An example of the information displayed during encounter review is illustrated in FIG. 15. The information displayed is reformulated for purposes of the encounter review from information previously requested by PC-CSMS and entered by the user. For example, during encounter review, drug requests are displayed, and notes relating to the encounter may be entered by the user and/or displayed. In addition, any over-the-counter consultation requests, extended consultation requests, screening requests, other prescriptions, over-the-counter drugs, and reported problems may be displayed.

Figure 16:
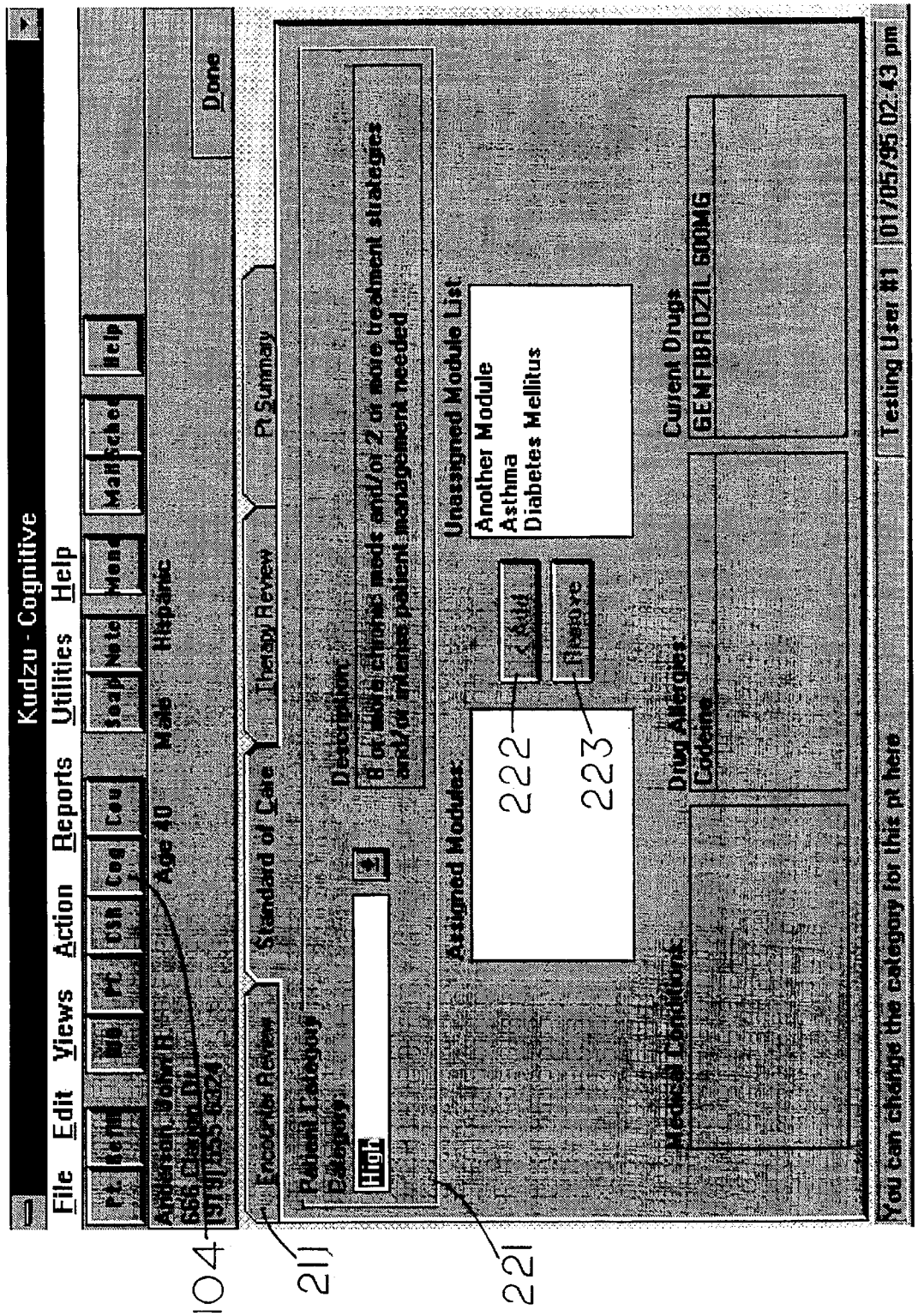

If the "Standard of Care" tab is selected during cognitive processing, PC-CSMS displays a "Standard of Care" screen similar to that illustrated in FIG. 16 prompting the user to categorize the current patient and to assign patient "modules" to the patient. The user can select the category from a list of options including "Low," "High" and "Special" as indicated by the "↓" key adjacent the "Category" field. A patient categorized as "Low" is a basically healthy person. A patient categorized as "High" has some problems which may be chronic. In other words, the patient may have some condition that requires monitoring such as diabetes, hyperactiveness or a serious illness. Finally, the "Special" category refers to anything that the user (i.e., pharmacist) wants to specifically note such as obesity. A description of the category is also displayed. In addition, during standard of care processing, a module list is displayed from which the user may select modules to be assigned to the patient. Modules are added or assigned to a patient using "Add" key 222 in which case the modules are added to the list. Modules may be removed from the list of modules assigned to the patient by using "Remove" key 223. In addition, medical conditions, allergies and current drugs are also displayed.

If the user decides to conduct the "Therapy Review" by selecting the appropriate tab at 211, generally, the pharmaceutical care cognitive services management system interactively prompts the user to indicate therapy goals for the user as well as to make any necessary alterations to the prescribed drug. In essence, the therapy review portion of the cognitive subsystem is where PC-CSMS displays the results of the automated portion of the drug utilization review and allows the pharmacist to review these results and make any necessary changes.

Figure 17:
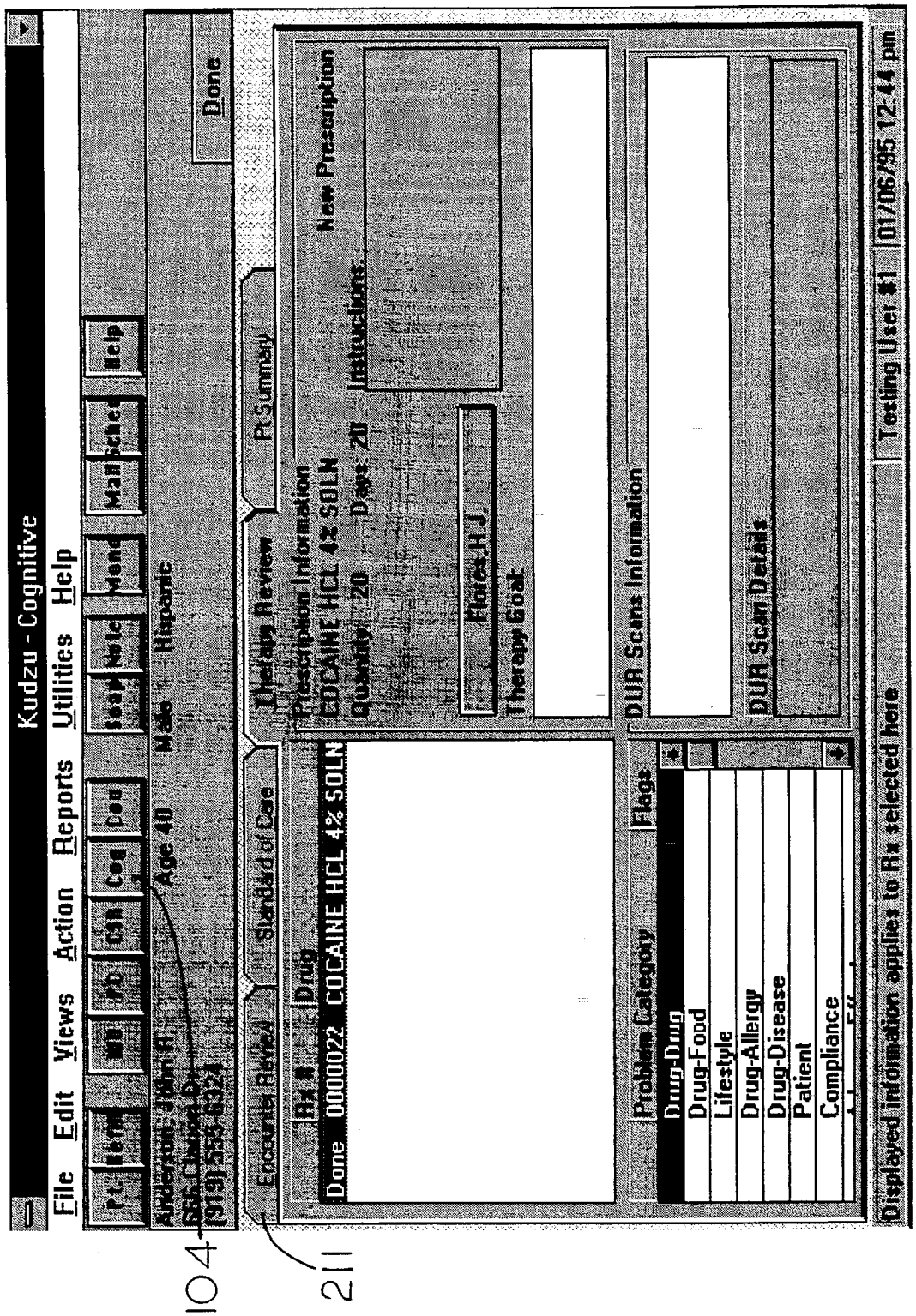
Figure 18:
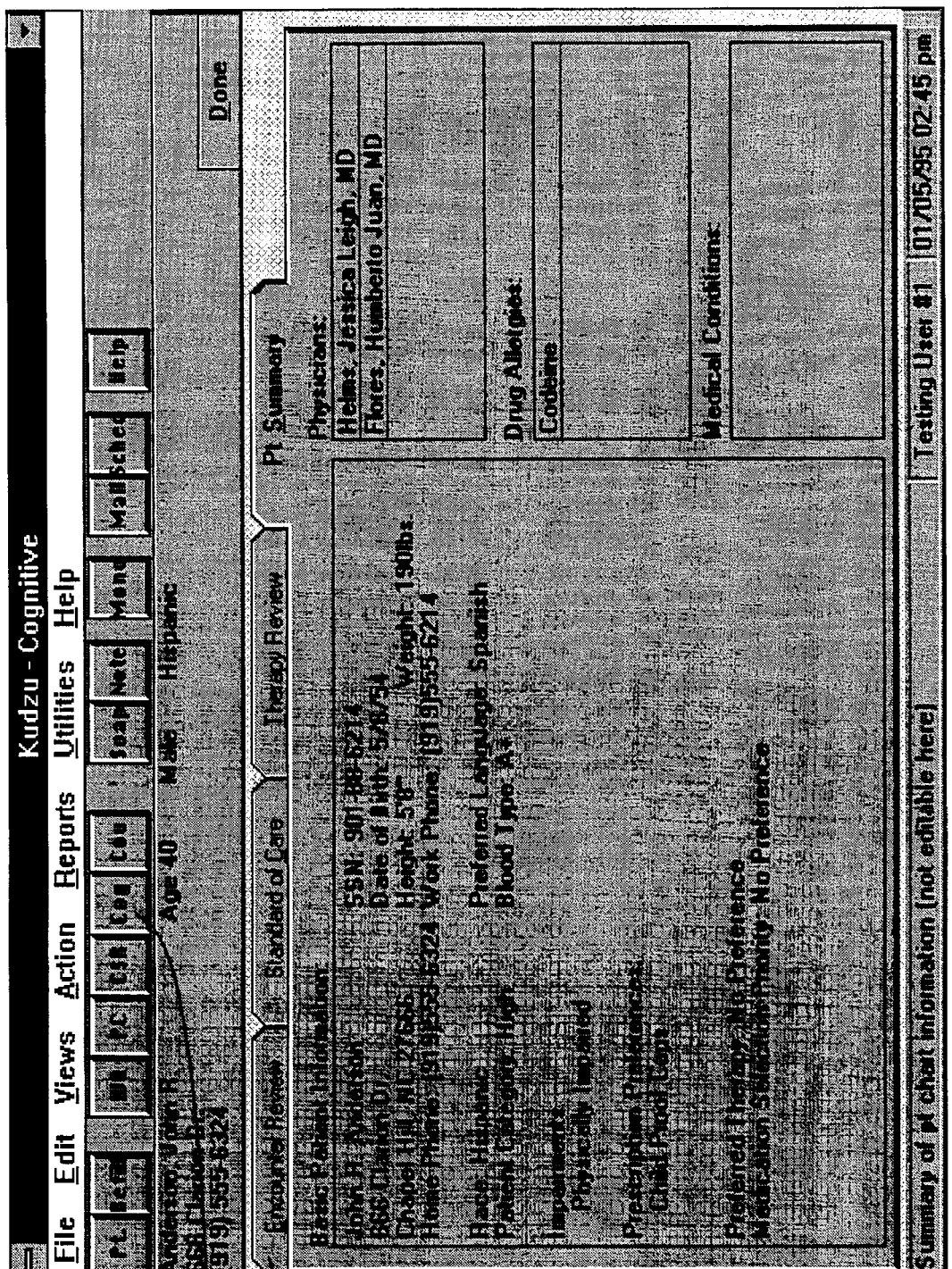

Referring to FIG. 17, the drugs prescribed and to be reviewed by the pharmacist are displayed on display device 20. The list of drugs includes not only the prescription number, the drug, the form of the drug (e.g., tablet), as well as the quantity of each unit, but also an indication as to whether the pharmacist has completed the therapy review for each particular drug. If the therapy review has been completed, "Done" is listed adjacent to the drug. Problem categories are also listed during therapy review. The problem categories indicate any potential problems which may arise from interactions between drugs, interactions between drugs and food, the lifestyle of the patient, interactions between drugs and allergies, interactions between drugs and diseases, the particular patient or the particular patient's compliance with the prescription and proposed drug therapy. If the automated portion of the DUR determines that a possible problem could occur, it is "flagged" adjacent the category in the listing of problem categories. In addition, the pharmacist must complete the analysis of the problem category.

In addition, during therapy review, prescription information is listed in the form of identification of the drug, quantity, and the days the drug is to be taken. The physician's name (e.g., Flores, H. J.), and instructions for taking the medication also are displayed. During therapy review, PC-CSMS requires the pharmacist to conduct a SOAP for each flagged problem category. If two problems are flagged in any problem category, a separate SOAP must be conducted for each flag. An indication of the SOAPs conducted may be displayed on display device 20. The SOAP must be created by the pharmacist before PC-CSMS will indicate that the problem category analysis is "Done" and that the therapy review for the drug is "Done." The SOAP subsystem will be described below with respect to FIGS. 27–28, 33–35 and 50. Finally, the pharmacist may enter a goal for the therapy. This is simply an indication of the purpose of taking the drug.

Finally, by selecting the "Pt. Summary" tab at 211, generally, the user may review a summary of patient information during the processing by the cognitive subsystem. If this tab is selected, a summary of patient information is displayed similar to that illustrated in FIG. 18. The information, as discussed before with respect to patient summary during cognitive service record processing, includes basic patient information, and listings of the patient's physicians, allergies and medical conditions.

The pharmaceutical care cognitive services management system requires the pharmacist to at least view all phases of the cognitive analysis during cognitive processing. As a result, PC-CSMS will not exit cognitive processing until everything in therapy review has at least been reviewed by the pharmacist. The only exception to this is if cognitive processing is suspended by the patient or refill interrupt which will be described below. If the cognitive processing is suspended, it is resumed after completion of the patient or refill interrupt.

Detailed Operation: Counseling Subsystem

Referring to FIGS. 19–22, processing of the counseling subsystem will now be described in detail. Similar to the patient intake subsystem (i.e., patient chart and cognitive service report) and the Cognitive subsystem, the counseling subsystem may be invoked by selecting the "COU" key 105. Generally, PC-CSMS 24 brings the patient, the pharmacist and the prescription together at the same time to complete the encounter with the patient during counseling processing. Requests noted during cognitive service record processing will be completed during counseling processing. The patient must be present during the counseling session in order to allow the user (i.e., pharmacist) of PC-CSMS 24 to complete the encounter with the patient. Similar to the cognitive subsystem, the user of the counseling subsystem must be a pharmacist. Generally, the counseling subsystem has four parts including "Therapy Management", "Standard of Care", "Encounter Management" and "Patient Summary". Therapy management, standard of care, encounter management or patient summary may be invoked by the user at any time during counseling processing by selecting the appropriate tab at 281.

Figure 19:
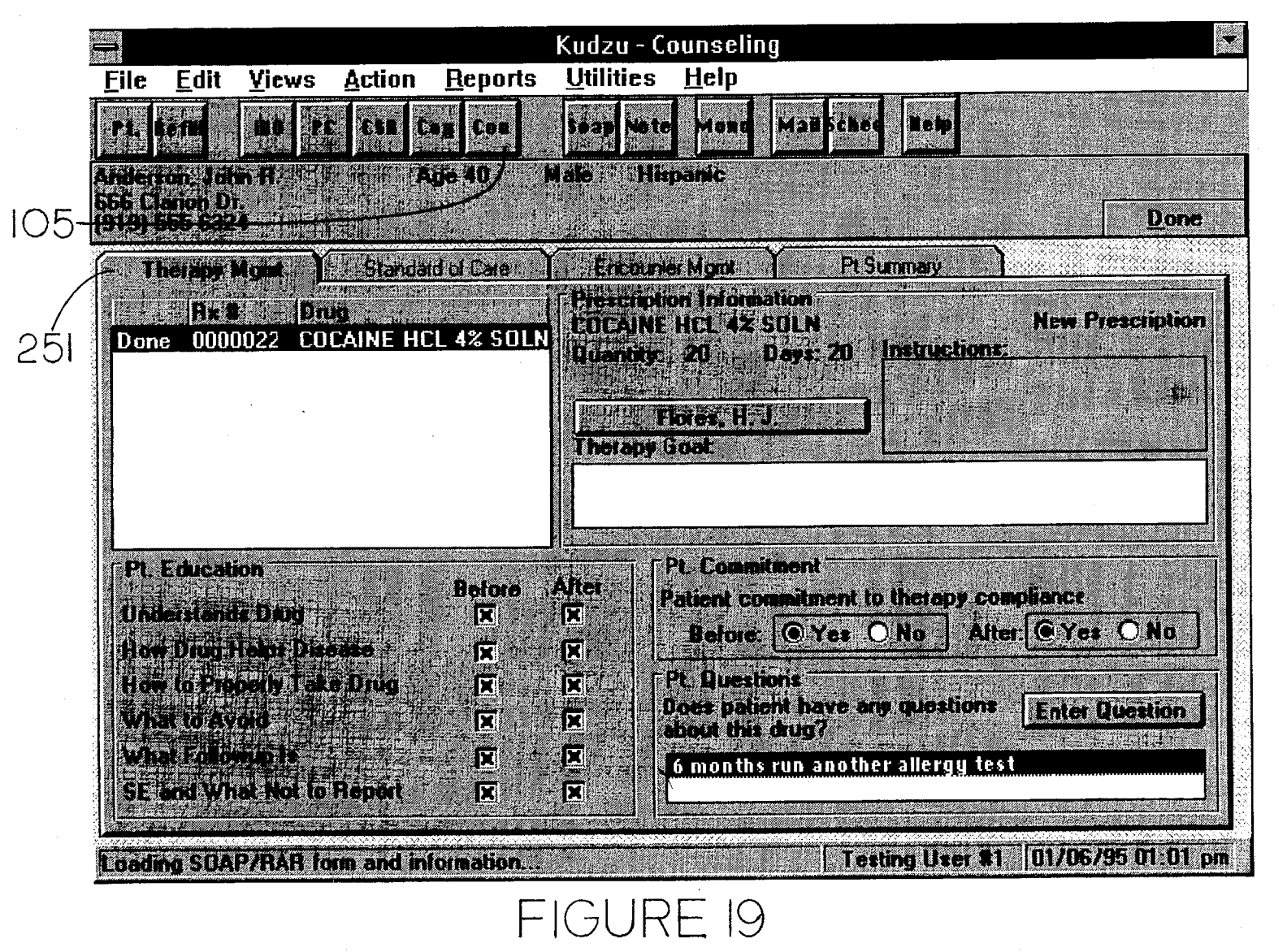

During therapy management, PC-CSMS 24 interactively prompts the pharmacist through the counseling session with the patient so that the patient understands what drug he is receiving, understands the purpose for the drug, and understands what the drug will do for him. Referring to FIG. 19, PC-CSMS 24 displays a list of the drugs prescribed for the patient including the prescription number and the identification of the drug. In addition, as illustrated in FIG. 19 the therapy management for a particular drug is noted as having been completed by the inclusion of "Done" next to the drug. Information previously received by PC-CSMS 24 with respect to the highlighted drug is also displayed, including the drug name, the form of the drug, the size of the unit dosage, the number of units of the drug, the number of days the drug is to be administered, and the prescribing physician's name. In addition, instructions for taking the drug as well as the therapy goal are also displayed. Finally, the therapy goal, if completed during processing by the cognitive subsystem, will be displayed. Otherwise, the pharmacist can complete this field during therapy management.

Also during therapy management, the pharmacist using PC-CSMS will advise the patient with respect to the drug, how the drug helps the disease, how to properly take the drug, what to avoid taking while on the drug, what, if any, follow-up is necessary, and so forth. As the user of PC-CSMS completes each portion of this counseling session, the user must indicate that each portion has been discussed with the patient and completed by making an appropriate indication on the screen as illustrated in FIG. 19. Still further, the pharmacist makes an observation with respect to the commitment of the patient to the drug therapy and records the results of the observation. Finally, the pharmacist enters any questions the patient may have with respect to the drug or the proposed therapy. Patients' questions are processed by PC-CSMS 24 as SOAPs. As a result, a SOAP is created for each question listed. The SOAP subsystem will be discussed below with respect to FIGS. 27–28, 33–35 and 50.

Figure 20:
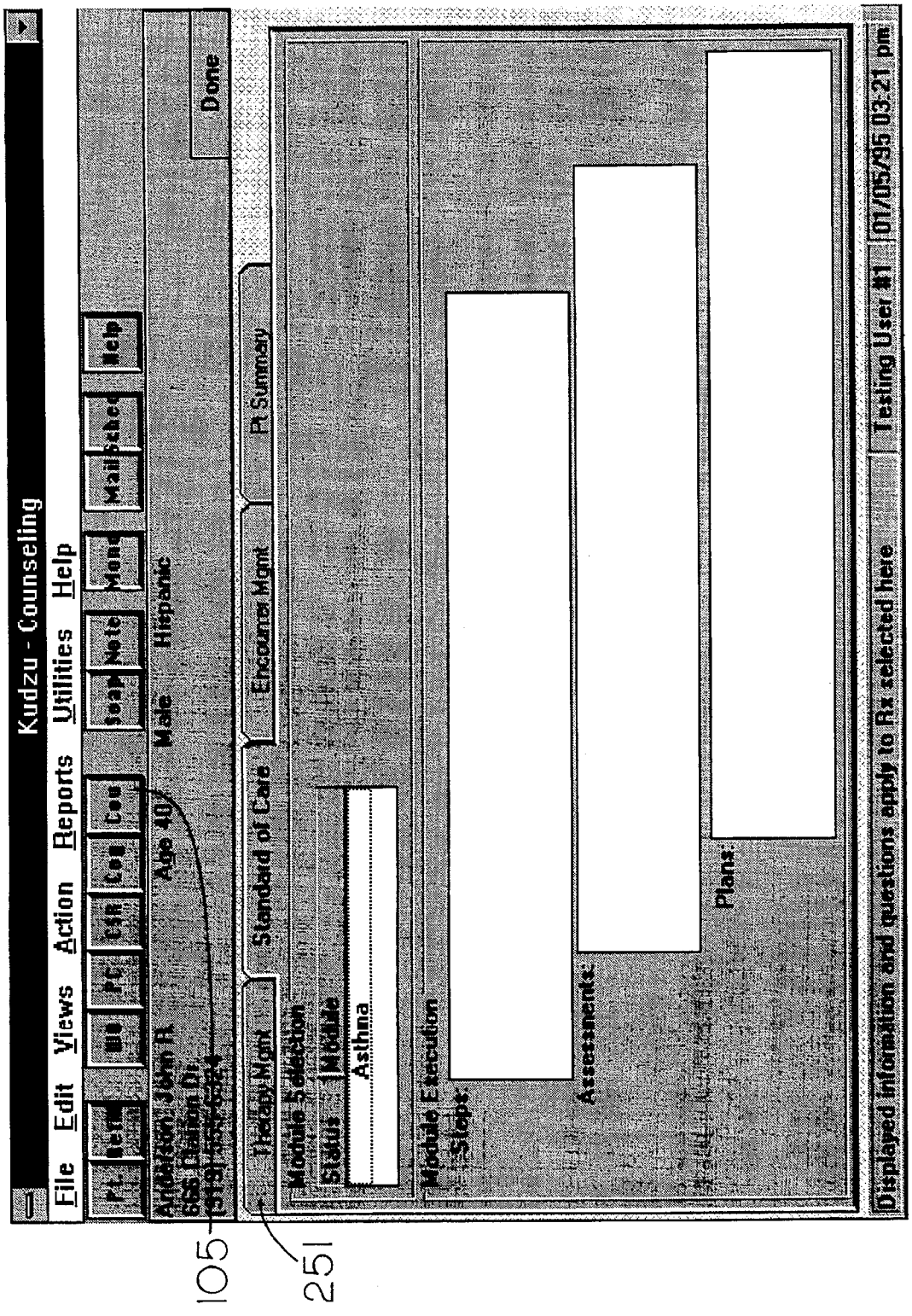

If the "Standard of Care" tab is selected during counseling processing, PC-CSMS 24 displays any modules assigned to the patient on display device 20 as illustrated in FIG. 20. If any modules were assigned to the patient during processing by the cognitive subsystem, the steps to be performed for each module will also be displayed on display device 20. PC-CSMS 24 processes these steps interactively by requiring the pharmacist to indicate that each step listed has been completed, and if testing is needed, prompts the pharmacist to record the results of the testing such as the results of taking the patient's blood pressure.

If the "Encounter Mgmt" tab at 251, generally, is selected during counseling processing, PC-CSMS 24 identifies tasks to be completed for this encounter with this particular patient. The tasks to be completed may include module steps not completed during the standard of care procedure for counseling, SOAPs not completed, and notes previously generated by the pharmacist or a technician that requires some action. Thus, PC-CSMS 24 keeps track of modules, SOAPs and notes so that all modules, SOAPs and notes have been completed or addressed prior to completing processing by the counseling subsystem for the patient.

Figure 21:
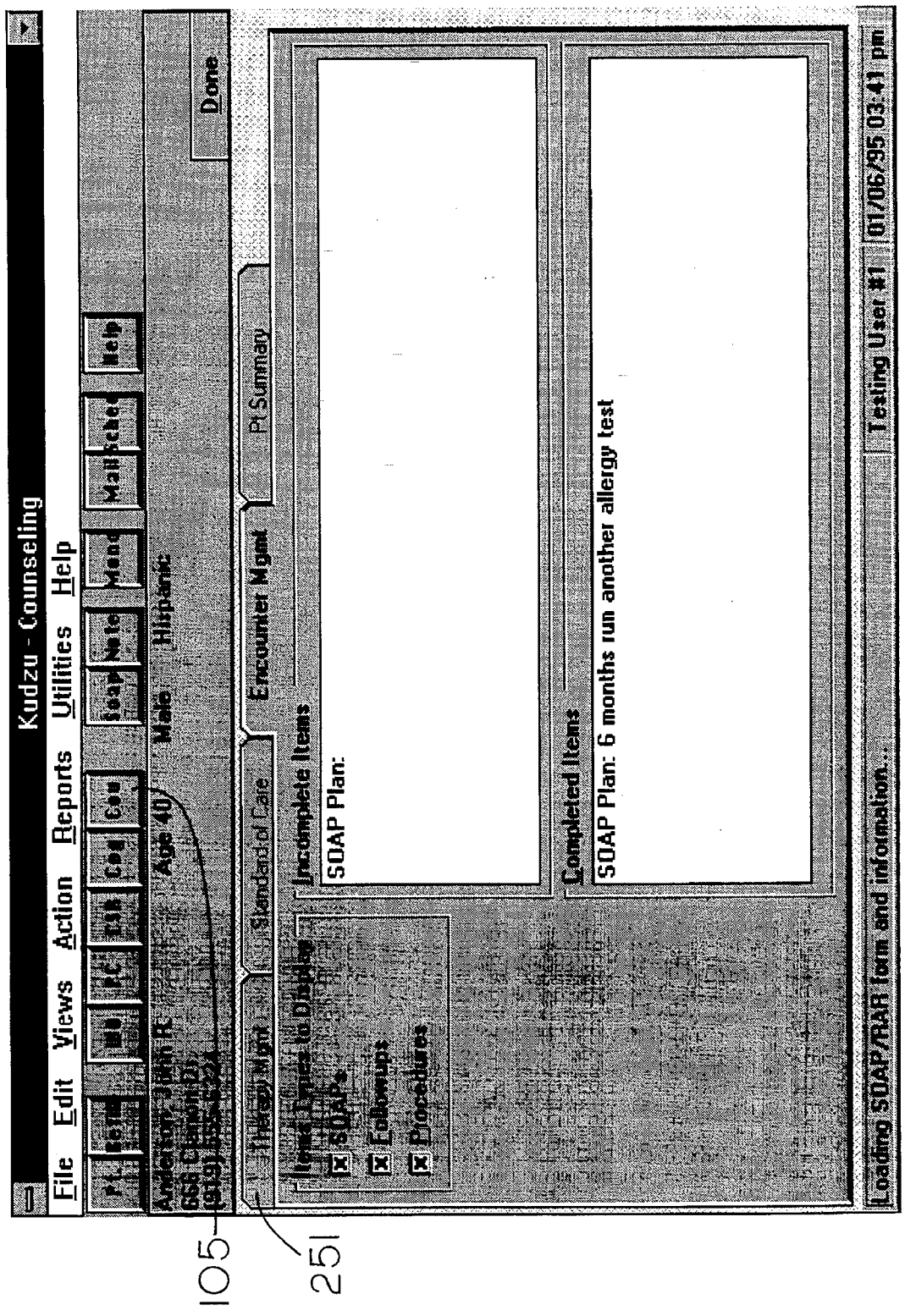
Figure 22:
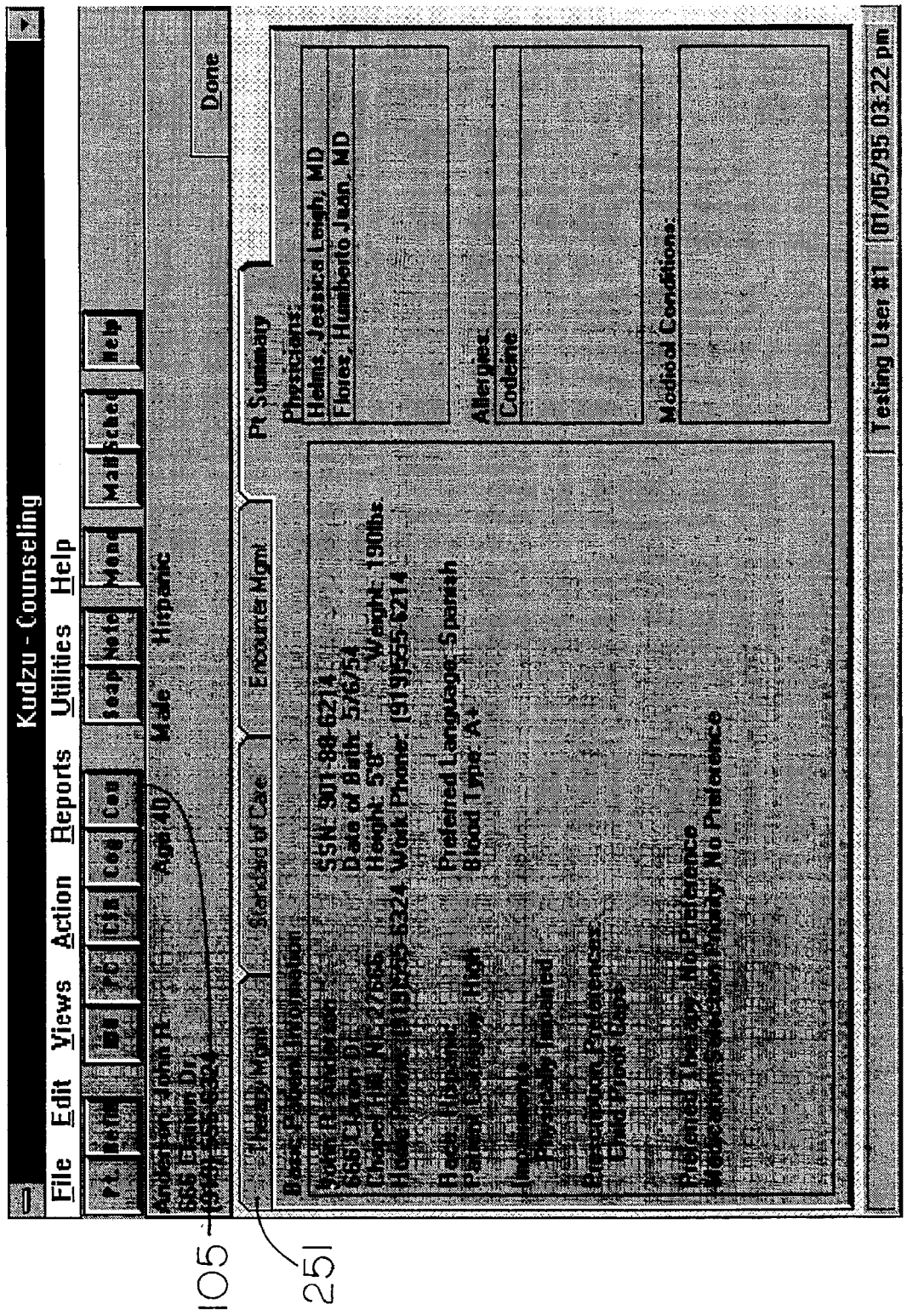

During encounter management, PC-CSMS displays a list of incomplete items which need to be addressed by the pharmacist and a list of completed items previously addressed by the pharmacist on display device 20 as illustrated in FIG. 21. In addition, PC-CSMS displays item types which allows a listing of incomplete items to be subset into types such as "SOAPs", "Follow-ups" or "Procedures". Finally, in response to selection of the "Pt. Summary" tab at 251, generally, during counseling processing, a summary of patient information similar to that displayed by PC-CSMS during processing of the cognitive service record and by the cognitive subsystem is displayed on display device 20 as illustrated in FIG. 22. The information displayed includes basic patient information and listings of the patient's physicians, allergies, and medical conditions.

Detailed Operation: Report Generation Subsystem and Dispensing

Pharmaceutical care cognitive services management system 24 also generates reports which may be given to the patient and which may be maintained by the pharmacist or sent to the physician. The reports summarize the encounter. These reports may include health related reports as well as billing statements for the counseling provided by the patient. Various types of billing statements may be generated including a standard CSR report, a NARD report which allows a pharmacist to bill for cognitive services, and a HCFA 1500 report which is used in association with health care paid for by government agencies. Multiple bills for services may be included as separate line entries on a single billing statement. The user of PC-CSMS 24 may initiate the generation of various reports by selecting a "Report" key (not shown). PC-CSMS 24 may also be connected to a dispensing system (not shown) used for dispensing the identified drug. Dispensing may be done at the same time as the cognitive session, but is typically completed prior to the counseling session.

Detailed Operation: Patient and Refill Interrupt Subsystems

As previously discussed, PC-CSMS 24 allows the user to suspend processing by the cognitive subsystem or the counseling subsystem by invoking a patient interrupt or a refill interrupt. If the patient interrupt or refill interrupt are invoked, and PC-CSMS is presently processing cognitive or counseling sessions, PC-CSMS 24 suspends the cognitive or counseling session, processes the patient or refill interrupt, and, upon completion of processing of the patient or refill interrupt, resumes processing of the suspended cognitive or counseling session. The detailed operation of the patient interrupt will be described below. Detailed operation of the refill interrupt will be described thereafter.

Figure 23:
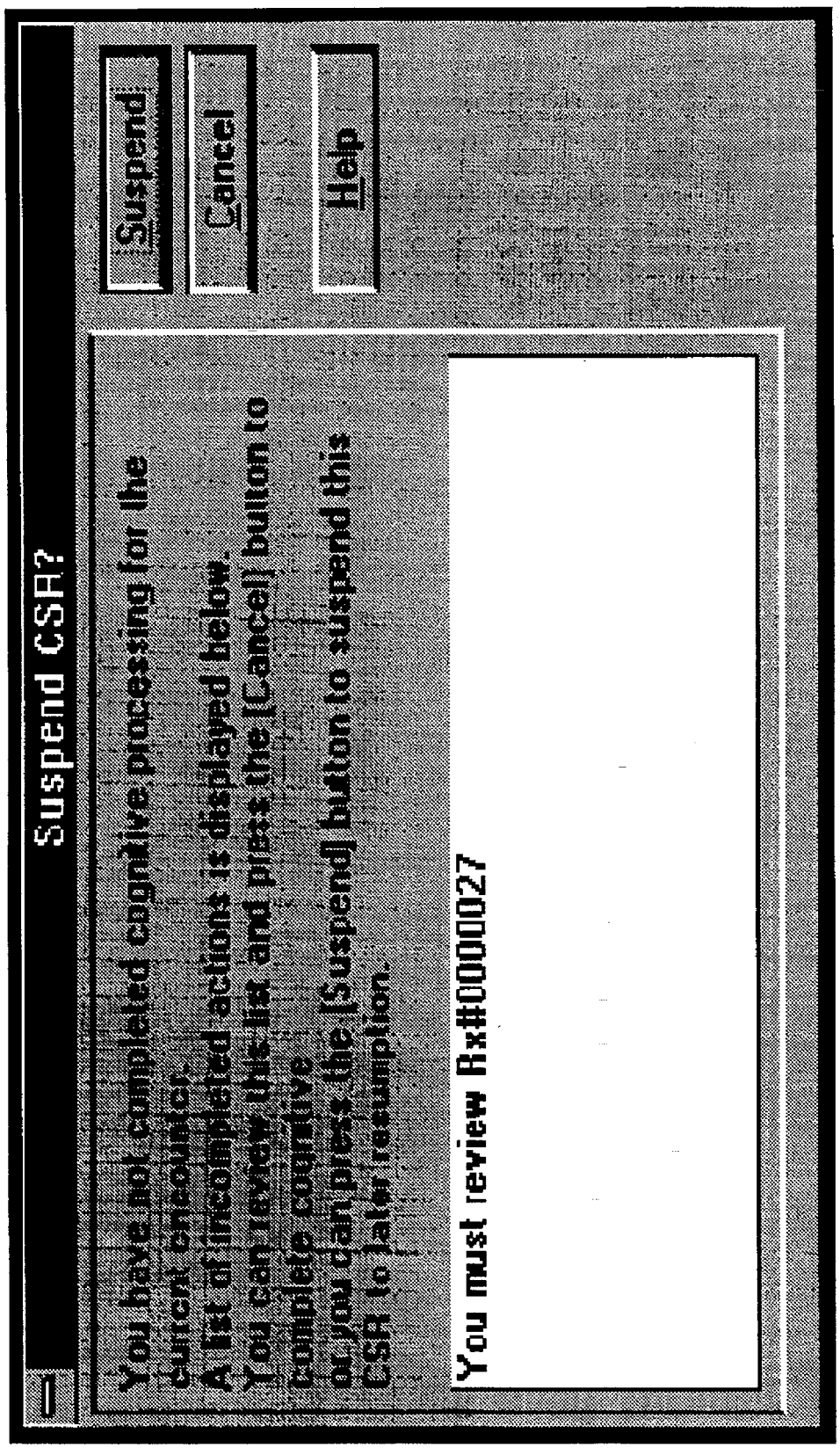
Figure 24:
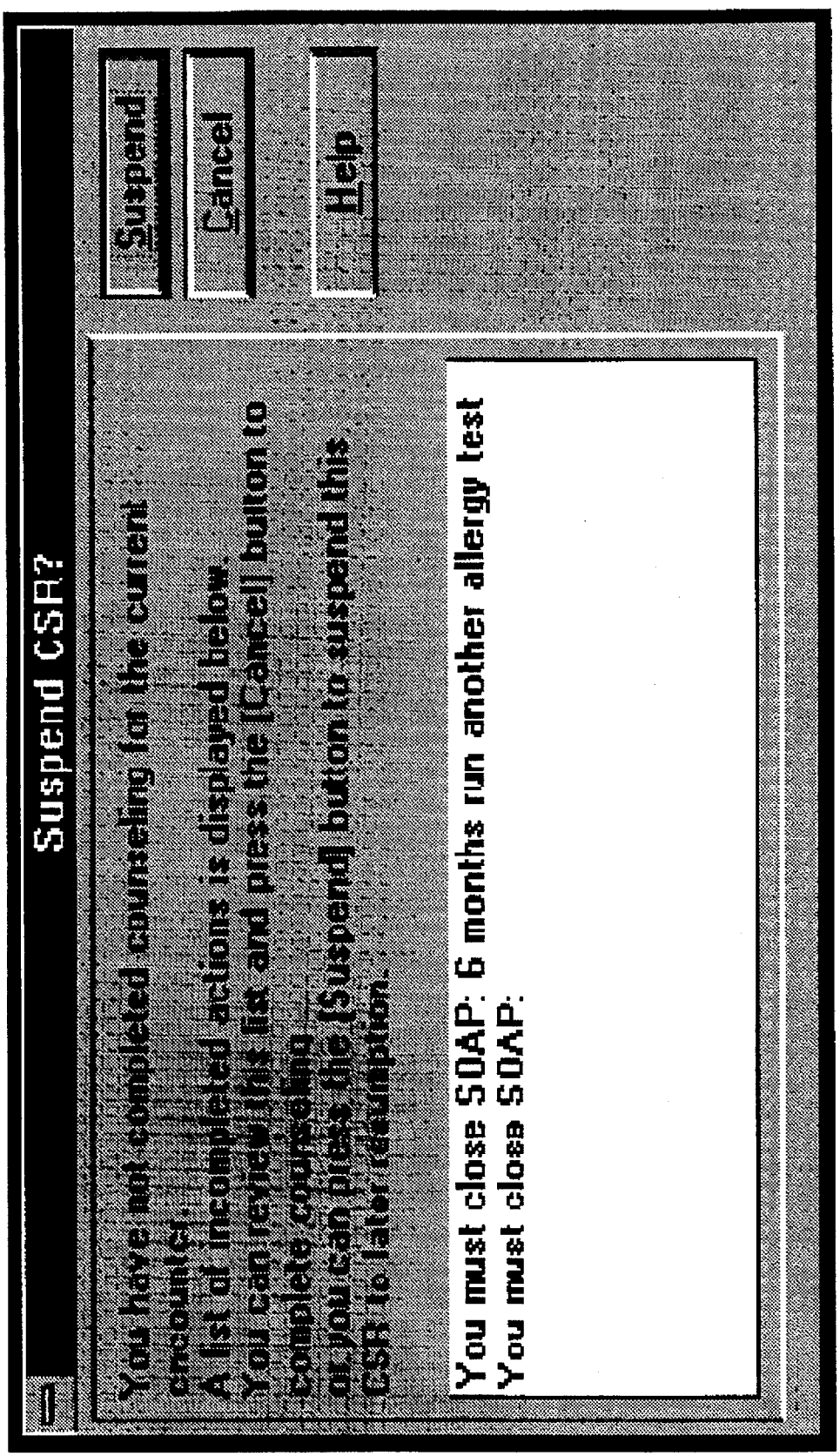

Referring to FIGS. 23, 24 and 49, the patient interrupt subsystem will now be described in detail. Similar to the other operations available to the user of PC-CSMS, processing by the patient interrupt subsystem may be invoked by selecting the "Pt." key 106. Generally, in response to a user invoking the patient interrupt subsystem, PC-CSMS 24 will give the user the option of suspending processing by the cognitive or counseling subsystem, or canceling the interrupt and continuing processing by the cognitive or counseling subsystem. If the user invokes the patient interrupt subsystem and PC-CSMS 24 is in the cognitive processing state, PC-CSMS 24 prompts the user by displaying a screen similar to that illustrated in FIG. 23 to select whether the user wants to suspend the cognitive processing and resume it at a later time, cancel the interrupt and continue the current cognitive processing session, or seek online assistance (i.e., help). Similarly, if the user selects the patient interrupt subsystem and PC-CSMS 24 is in the counseling processing state, PC-CSMS prompts the user by displaying a screen similar to that illustrated in FIG. 24 on display device 20 to either suspend the current counseling session and resume it at a later time, cancel the interrupt and continue the current counseling session or seek online help.

Whether PC-CSMS is executing in the cognitive subsystem, counseling subsystem or some other processing state, PC-CSMS will prompt the user to either select a patient, intake a patient, add a new patient or cancel the patient interrupt by displaying a screen similar to that illustrated in FIG. 25 on display device 20 upon selection of the "Pt." key 106. During processing by the patient interrupt subsystem, fields for entry of the "Last Name" and "First Name" of a patient, and a listing of patients are displayed on display device 20. The listing of patients may be scrolled to locate a patient either alphabetically before or after those displayed in the window illustrated in FIG. 25. In addition, options for processing a patient interrupt are provided to the user through the use of keys or buttons 291–296. In particular, the user may select the "Pt. Chart" key 291 to view or update the patient chart of the interrupting patient, "Pt. Requests" key 292 to take in information from the patient, fill a new prescription, refill an existing prescription or to document reasons for the patient's call, "New Pt." key 293 to create a patient chart for a new patient, or "Cancel" key 294 to terminate the patient interrupt and return to the processing from which the patient interrupt was invoked. The user may also select the "Help" key 295 to seek online help provided by PC-CSMS or the "Search" key 296 to search for the patient name entered by the user. "Pt. Chart" key 291 and "Pt. Requests" key 292 are only enabled for a valid patient name entered in the Last Name and First Name fields or selected from the list of patients. "New Pt." key 293 is enabled whether or not a valid patient name is entered.

Generally, if the patient for whom the patient interrupt subsystem was invoked is listed in the list of names, the user may scroll the list of names until the interrupting patient is located within the list. Similarly, the user may enter the patient's last name followed by the first name in the appropriate fields and PC-CSMS will automatically scroll the list of patient names to locate the name of the patient entered by the user upon the user's selection of the "Search" key 296. If "Pt. Chart" key 291 is selected, the patient chart for the interrupting patient is retrieved and the patient chart component of the patient intake subsystem previously described is initiated to allow the user to review or update the patient chart for the interrupting patient. If the "Pt. Requests" key 292 is selected by the user, PC-CSMS 24 initiates the cognitive service record component of the patient intake subsystem for the interrupting patient identified in the list of patient names. The cognitive service record processing was previously described above. If the "New Pt." key 293 is selected by the user, PC-CSMS transfers control to the patient chart component of the patient intake subsystem which was previously described to allow the user to create a patient chart for a new patient. Finally, if the "Cancel" key 294 is selected by the user, processing by the patient interrupt subsystem is terminated and control is returned to the calling process.

If the patient interrupt subsystem was invoked during either cognitive or counseling processing, PC-CSMS resumes processing of the suspended cognitive process or the suspended counseling process, respectively, upon completion of processing by the patient interrupt subsystem.

Upon selection of "Refill" key 107, PC-CSMS invokes the refill interrupt subsystem. Similar to the patient interrupt subsystem, PC-CSMS will suspend the current processing by the cognitive subsystem or counseling subsystem if PC-CSMS is processing a cognitive session or a counseling session at the time the refill interrupt subsystem is invoked by the user. PC-CSMS 24 will prompt the user to decide whether to suspend the current cognitive or counseling sessions and resume processing of the respective session upon completion of the refill interrupt processing, or to cancel the interrupt and continue the current cognitive or counseling session. The system prompts the user to make this decision and selection by displaying screens similar to those illustrated in FIGS. 23 or 24 on display device 20. If the refill interrupt subsystem was invoked while PC-CSMS 24 was processing any procedure other than a cognitive session or counseling session, PC-CSMS simply terminates those other sessions.

Figure 26:
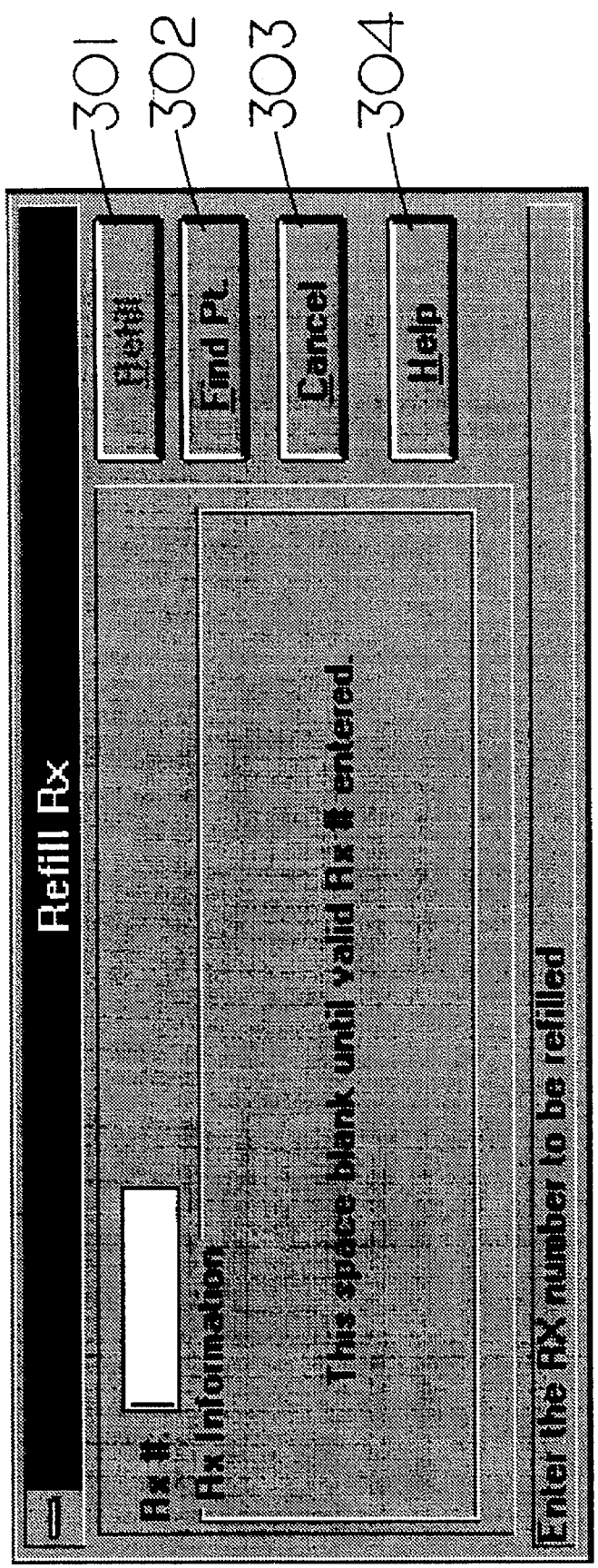

Upon selection of the refill interrupt, PC-CSMS displays a screen similar to that illustrated in FIG. 26 on display device 20 which provides a field (i.e., "Rx #") for the user to enter the prescription number of the drug to be refilled. In addition, the system also displays information corresponding to the particular prescription number and provides the user with the options of initiating a refill procedure by selecting the "Refill" key 301, finding a patient by selecting the "Find Pt." key 302, canceling processing by the refill interrupt subsystem by selecting the "Cancel" key 303 or asking the system for online help by selecting the "Help" key 304. "Refill" key 301 is only enabled if it is determined that a valid prescription number was entered in the "Rx #" field.

Upon the user's entry of the number of the prescription to be refilled, PC-CSMS 24 makes the determination as to whether the prescription number is a legitimate number. If the prescription number is a legitimate number and the user selects "Refill" key 301, control is transferred to processing of the cognitive service record for the entered prescription number. If the prescription number entered by the user is legitimate and the user selects the "Find Pt." key 302, control is transferred to the patient processing and the patient intake screen similar to that illustrated in FIG. 25 is displayed on display device 20 to allow the user to locate the patient for the particular prescription. The system will automatically highlight the name of the patient in the list of patient names of FIG. 25 which corresponds to the prescription number entered by the user during processing by the refill interrupt subsystem. If the "Cancel" key 303 is selected, processing by the refill interrupt subsystem is terminated whether or not the prescription number is legitimate. If the "Help" key 304 is selected, control is transferred to help menus to allow the user to access online assistance.

If a determination is made that the prescription number entered by the user is not legitimate, the "Refill" key 301 will be inactive. However, the user may select the "Find Pt." key 302, the "Cancel" key 303 or the "Help" key 304. The only difference in the processing is if the "Find Pt." key 302 is selected, control is transferred to patient processing and the patient intake screen similar to that illustrated in FIG. 25 is displayed on display device 20, but no patient name will be highlighted corresponding to the prescription number since the prescription number was not legitimate.

Finally, upon completion of the processing by the refill interrupt subsystem, a determination is made as to whether control by the patient interrupt subsystem was received from either a suspended cognitive session or a suspended counseling session. If the refill interrupt subsystem was invoked during either cognitive or counseling processing, PC-CSMS allows the user to resume processing of the suspended cognitive process or the suspended counseling process, respectively, upon completion of processing by the refill interrupt subsystem.

Referring to FIG. 49, a high level flowchart of the processing by the patient and refill interrupt subsystems 36 is illustrated. The high level control of the patient and refill interrupt subsystems will now be described. A determination is made at 310 as to whether the patient interrupt subsystem was invoked. If the patient interrupt subsystem was invoked, a determination is made at 311 as to whether the system is currently processing a cognitive session for a first patient. If it is determined at 311 that the system is currently processing a cognitive session for a first patient, the cognitive session for the first patient is suspended at 312 and the patient interrupt for the second patient is processed at 313. Upon completion of the processing of the interrupt for the second patient, control is returned to the suspended cognitive session for the first patient and processing of that cognitive session is resumed at 314.

If it is determined at 311 that cognitive processing for a first patient is not currently being performed, a determination is made at 315 as to whether the system is presently processing a counseling session for a first patient. If it is determined at 315 that the system is presently processing a counseling session for a first patient, processing of the counseling session for the first patient is suspended at 316 and control is transferred to patient processing for processing the interrupt for the second patient at 317. Upon completion of the processing for the second patient at 317, control is returned to the suspended counseling session and processing of the suspended counseling session for the first patient is resumed at 318. If it is determined at 315 that a counseling session for the first patient is not presently being processed, then the current session (e.g., patient intake, cognitive service record, etc.) is terminated and the control is transferred to patient processing to process the interrupt for the second patient at 319.

If it is determined at 310 that the patient interrupt was not selected, a determination is made at 320 as to whether the refill interrupt was selected. If the refill interrupt was selected, a determination is made at 321 as to whether the system is presently processing a cognitive session for a first patient. If the cognitive session for a first patient is being processed, this cognitive session for the first patient is suspended at 322 and the refill interrupt for the second patient is processed at 323. Upon completion of the processing of the refill interrupt for the second patient, control is returned to the suspended cognitive session for the first patient, and processing of the suspended cognitive session for the first patient is resumed at 324.

If it is determined at 321 that a cognitive session for a first patient is not being processed, a determination is made at 325 as to whether a counseling session for a first patient is being processed. If a counseling session for the first patient is being processed, the counseling session for the first patient is suspended at 326 and the refill interrupt for the second patient is processed at 327. Upon completion of the processing of the refill interrupt for the second patient at 327, control is returned to the suspended counseling session and the processing of the suspended counseling session is resumed at 328.

If it is determined at 325 that a counseling session for a first patient is not presently being processed, the current session (e.g., patient intake, cognitive service record, etc.) is terminated and the refill interrupt is processed at 329.

Finally, if it is determined at 3201 that the refill interrupt was not selected by the user, a determination is made at 330 as to whether any of the other interrupts were selected. If any of the other interrupts was selected, the current session is terminated and the other interrupt is processed at 331. If it is determined at 330 that none of the other interrupts was selected, the current session continues to be processed until either a different session is selected or one of the interrupts is selected.

Detailed Operation: SOAP/RAR Subsystems

Figure 28:
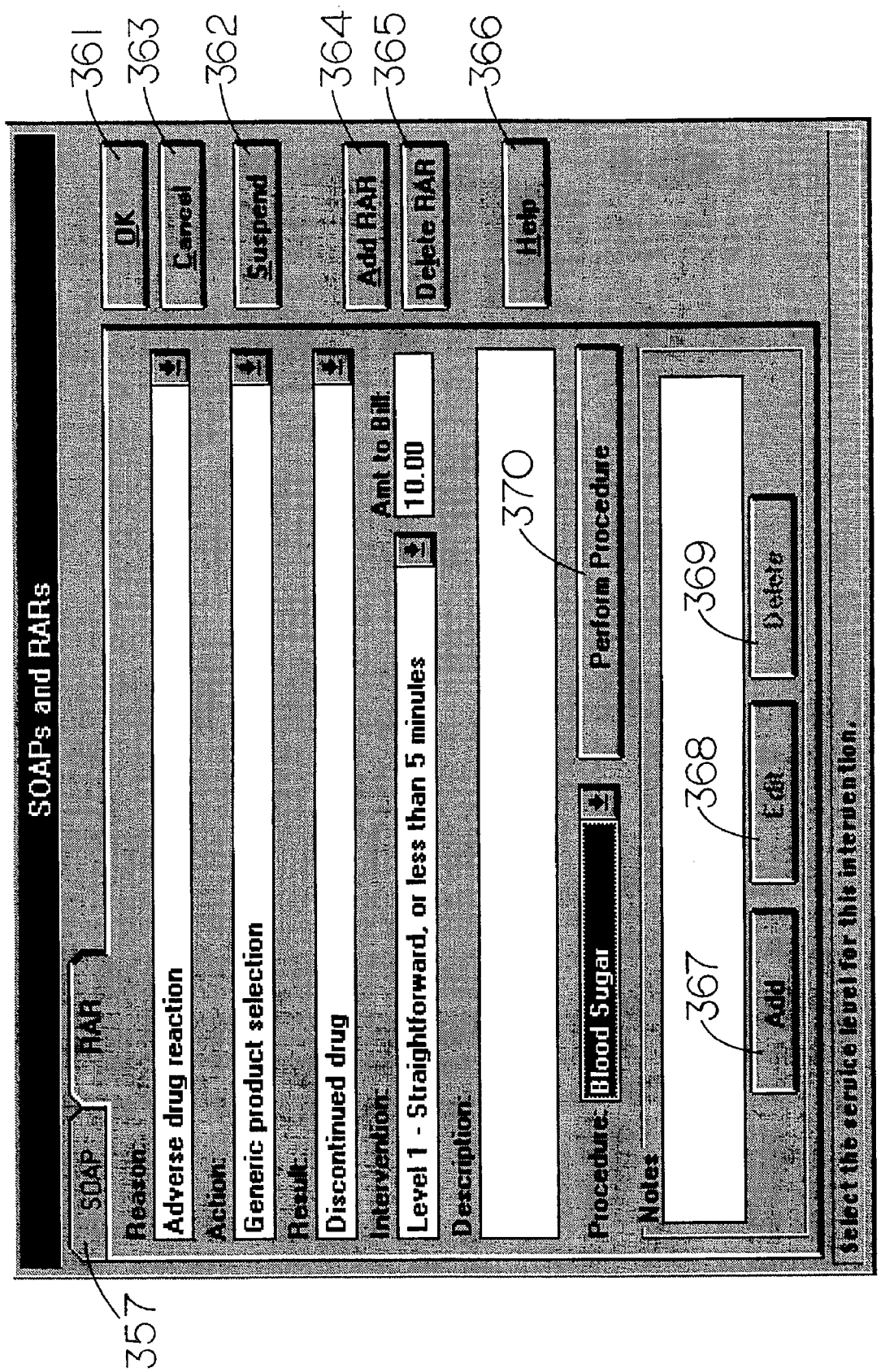

Referring to FIGS. 27–28 and 50, the SOAP (Subjective, Objective, Assessment and Plan) subsystem and the RAR (Reason, Action, Result) subsystem will now be described in detail. Similar to the patient and refill interrupt subsystems, the SOAP subsystem may be invoked at any time during use of the pharmaceutical care cognitive services management system. However, unlike the patient and refill interrupt subsystems, selection of the "SOAP" key 108 to invoke the SOAP subsystem, will not suspend any session currently being processed by PC-CSMS. Nonetheless, the SOAP subsystem can be invoked at any time during use of PC-CSMS. Still further, as described above, SOAPs are created for patient questions, DUR problems, commitment issues and other pharmacist concerns.

Upon selection of the "SOAP" key 108, PC-CSMS 24 displays a screen similar to that illustrated in FIG. 27 on display device 20. A number of fields are displayed which are to be completed by the user, in this case, the pharmacist. The fields include "Context," "Subjective," "Objective," "Assessment," "Plan" and "Procedure." The meanings of subjective, objective, assessment and plan were previously described above. Context refers to the identity of the session being processed when the SOAP subsystem was invoked. For example, if the SOAP subsystem had been invoked during processing of a cognitive service record session, the context would be identified as "CSR." The user may also select a procedure to be completed as a result of the processing by the SOAP subsystem from a predefined list as indicated by the "↓" symbol next to the "Procedure" field.

A number of options are provided by PC-CSMS for processing by the SOAP subsystem. These options include indicating that the SOAP process is completed by selecting the "OK" key 351, suspending the processing by the SOAP subsystem by selecting the "Suspend" key 352, canceling or terminating the processing of the current SOAP being processed by selecting the "Cancel" key 353, adding a RAR to the SOAP by selecting the "Add RAR" key 354, deleting the RAR associated with the SOAP by selecting the "Delete RAR" key 355, and viewing the online help by selecting the "Help" key 356. The SOAP may not be identified as being completed until all of the fields have been completed by the user. Suspension of the SOAP merely suspends the SOAP to allow the user to complete the SOAP at a later time. The addition of a RAR adds a "bid" RAR to be associated with the SOAP. The "blank" RAR must be completed by the user at some later time.

If the SOAP interrupt is invoked for a particular patient and a number of SOAPs are already associated with the patient, a list of SOAPs will be displayed for the user. This allows the user to select an individual SOAP to process.

Suspension and cancellation of the SOAPs will be understood by those skilled in the art. Selection of "Cancel" key 353 or 363 will undo any changes during creation or update of a SOAP or a RAR.

Finally, as previously mentioned, the selection of the "Add RAR" key 354 adds a "blank" RAR associated with the present SOAP being processed. Upon selection of the "Add RAR" key 354, the system displays a "blank" RAR on display device 20 similar to that illustrated in FIG. 28. If a RAR which is already associated with the current SOAP being processed by the SOAP subsystem is to be updated or at least reviewed by the user, the user may transfer control to the RAR subsystem by selecting the "RAR" tab displayed generally at 357 in FIG. 27. Similarly, while processing a "RAR," the user may return to the SOAP to which the present RAR is associated by selecting the "SOAP" tab illustrated at 357 in FIG. 28.

When creating a RAR using the RAR subsystem, a number of fields must be completed by the user. These fields, as illustrated in FIG. 28, include fields for "Reason," "Action," "Result," "Intervention," "Description," "Amount to Bill," "Procedure" and "Notes." Reason, action and result were previously described above and will not be repeated. The intervention field allows the user to enter the level of the intervention for purposes of recovering the value added by the pharmacist. In addition, the pharmacist should also include a description about the RAR encounter, any procedure to be performed, and complete any notes with respect to this RAR. The contents of the reason, action, result, intervention and procedure fields may be selected from a predefined list as indicated by the "↓" next to each of those respective fields.

The user may select from a number of options during processing of a RAR by the RAR subsystem. These options include indicating that the creation or processing of the RAR is completed by selecting the "OK" key 361, suspending the processing of the RAR to permit completion of the RAR at a later date by selecting the "Suspend" key 362, canceling or terminating the processing of the present RAR by selecting the "Cancel" key 363, adding an additional "blank" RAR by selecting the "Add RAR" key 364, deleting the present RAR by selecting the "Delete RAR" key 365, seeking online help from the system by selecting the "Help" key 366 or performing the procedure by selecting the "Perform Procedure" key 370. In addition, as indicated at the bottom of the screen illustrated in FIG. 28, the user may add, edit or delete notes by selecting the keys "Add" 367, "Edit" 368 or "Delete" 369, respectively. Notably, a RAR cannot be deleted after it has been completed and identified as being "OK." In effect, identifying a RAR as being "OK" results in it being "committed" to the database. The content of the intervention field essentially relates to the amount of work performed by the pharmacist with respect to this particular RAR.

As previously described, more than one RAR may be associated with a single SOAP. As a result, a multiple number of "RAR" tabs may appear at 357 on the screen displayed in FIG. 28.

Referring to FIG. 50, a high level flowchart illustrating the control of the processing by the SOAP subsystem in combination with the RAR subsystem to allow multiple RARs to be associated with a single SOAP will now be described. A determination is made at 401 as to whether the SOAP subsystem was invoked. If it is determined at 401 that the SOAP subsystem was invoked, PC-CSMS will create a new SOAP or process an existing SOAP for the current patient being processed at 402. Once the SOAP is completed, or even during the processing of a SOAP, the user may decide to create a first RAR. If it is determined at 403 that a first RAR is to be added, PC-CSMS will process the first RAR. If it is determined at 403 that a first RAR was not to be created or was not selected but rather a second RAR was selected for processing, control is transferred to block 405.

A determination is made at 405 as to whether a second RAR was to be created or was selected for processing. If a second RAR was to be created or was selected for processing, a determination is then made at 406 as to whether the second RAR is associated with the same SOAP as the first RAR. If it is determined at 406 that the second RAR is associated with the same SOAP as the first RAR, the second RAR is processed at 407 and an association is made between the first RAR and the second RAR to indicate that the first RAR and the second RAR are associated with the same SOAP at 408. Any additional RARs associated with the same SOAP will be processed at 409, and upon completion of processing of any of the SOAPs, or on suspension or cancellation of any of the SOAPS, control is transferred to any session or interrupt selected by the user from those illustrated at 101-113 displayed on the screen illustrated in FIG. 5. If a determination is made at 405 that a second RAR is not to be processed, control simply remains with the SOAP subsystem as long as the SOAP is being processed, after which control will be transferred to any of the sessions or interrupts 101-113 illustrated in FIG. 5 and selected by the user.

If a determination is made at 406 that the second RAR is not associated with the same SOAP as the first RAR, the second RAR is simply processed in association with the SOAP it is related to.

Detailed Operation: Note

PC-CSMS 24 also processes "Note" interrupts upon the selection of the "Note" key 109 by the user. Similar to processing of a SOAP interrupt by the SOAP subsystem, PC-CSMS displays a summary list of all notes for the particular patient presently being processed upon selection of the note interrupt. There are three types of notes processed by PC-CSMS, i.e., general notes, attentions and follow-ups. A general note records information about a patient or an encounter that does not fall within another field provided by the system. General notes not only appear in a note screen but also appear in the patient summary displayed during processing of the cognitive service record component of the patient intake subsystem as well as other processing. The general notes are associated with the patient using the patient ID number.

The attention note is used for the purpose of bringing some piece of information to the attention of a pharmacy employee at some later time. The attention note is flashed up on display device 20 during a specific stage of processing for a particular patient. The attention note also includes an indication to associate the note with a particular part of the processing for the particular patient (i.e., intake subsystem, cognitive subsystem or counseling subsystem). Finally, a follow-up note provides a reminder to a pharmacy employee to perform some procedure. The follow-up note must be processed by creating a SOAP for the follow-up note. The follow-up note also includes an indication as to when the follow-up with the patient is scheduled for, i.e., this visit, next visit, or date. When the date of the follow-up arrives, the follow-up note will appear in the incomplete list displayed on display device 20 during the encounter management portion of processing by the counseling subsystem.

Figure 29:
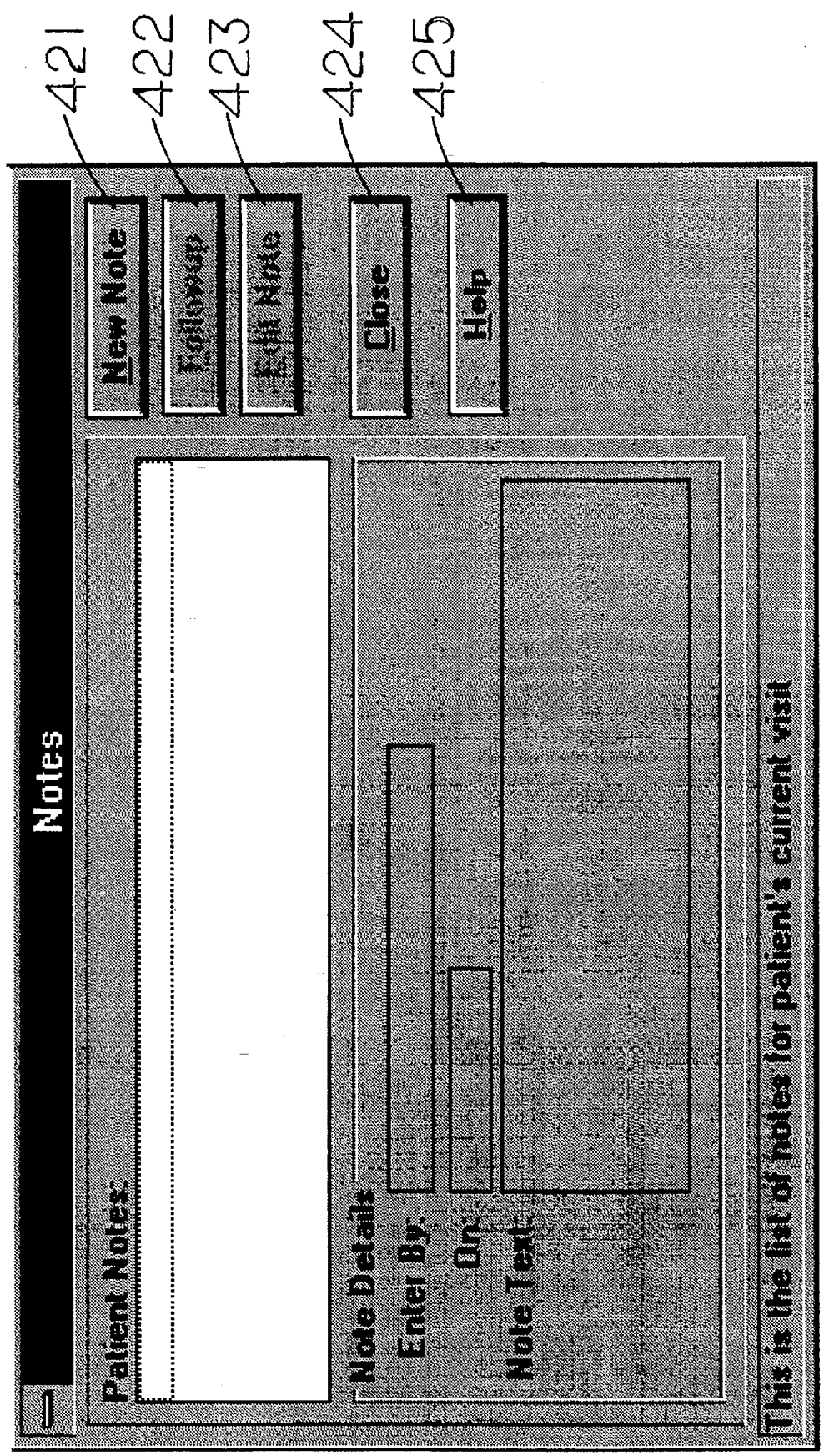

Referring to FIGS. 29, 30, 31 and 32, the control of the processing of the note interrupt will now be described. Upon selection of the note interrupt key 109 by the user, a listing of the notes for the particular patient being processed is displayed on display device 20 as illustrated in FIG. 29. Information displayed on the screen may include patient notes as well as any details with respect to the notes. A number of options are available for processing during the note interrupt. These options include creating a new note by selecting the "New Note" key 421, creating a follow-up note by selecting the "Follow-Up" key 422, editing a note by selecting the "Edit" note key 423, closing the note by selecting the "Close" key 424 and reviewing online help by selecting the "Help" key 425. If a new note is selected, one of FIGS. 30, 31 or 32 will be displayed. The particular progress note to be displayed will depend on which type of note (i.e., "General," "Attention" or "Follow-up") is selected and indicated in the "Type" field of the progress note. If the "Follow-up" key 422 is selected, a follow-up note will be displayed. If the "Edit Note" key 423 is selected, the note highlighted in the patient note list will be displayed. Closing of the note indicates that the note has been processed. "Edit Note" key 423 is only enabled when the list of patient notes contains at least one note.

Figure 30:
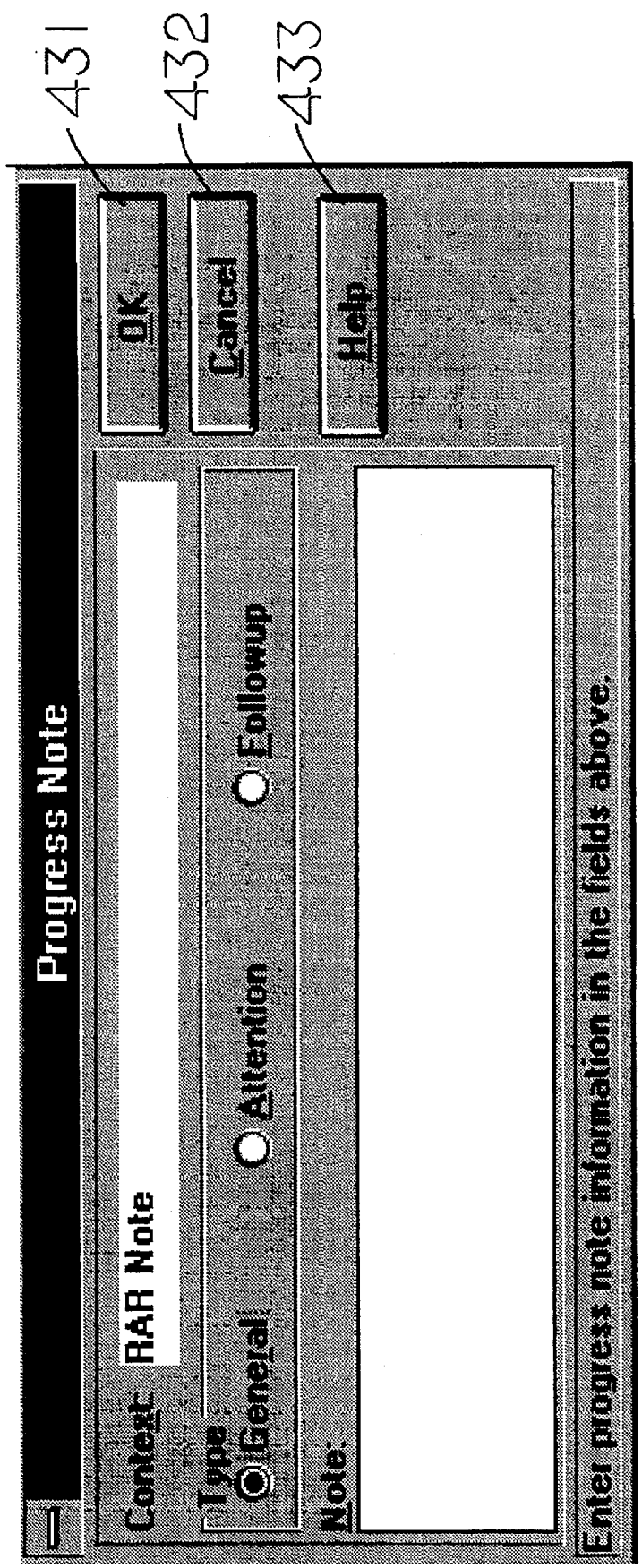

Referring to FIG. 30, a "General" note is illustrated as indicated by the indication next to "General" in the type field. Each note includes a field to be completed by the user to indicate the context for the note.

Each note can also be reviewed, updated or closed. By selecting the "OK" key 431 in FIG. 30, any updates to the notes are saved. If the "Cancel" key 432 is selected, any updates initiated during the current processing of the progress note are cancelled. If the "Help" key 433 is selected, online assistance can be accessed.

Figure 31:
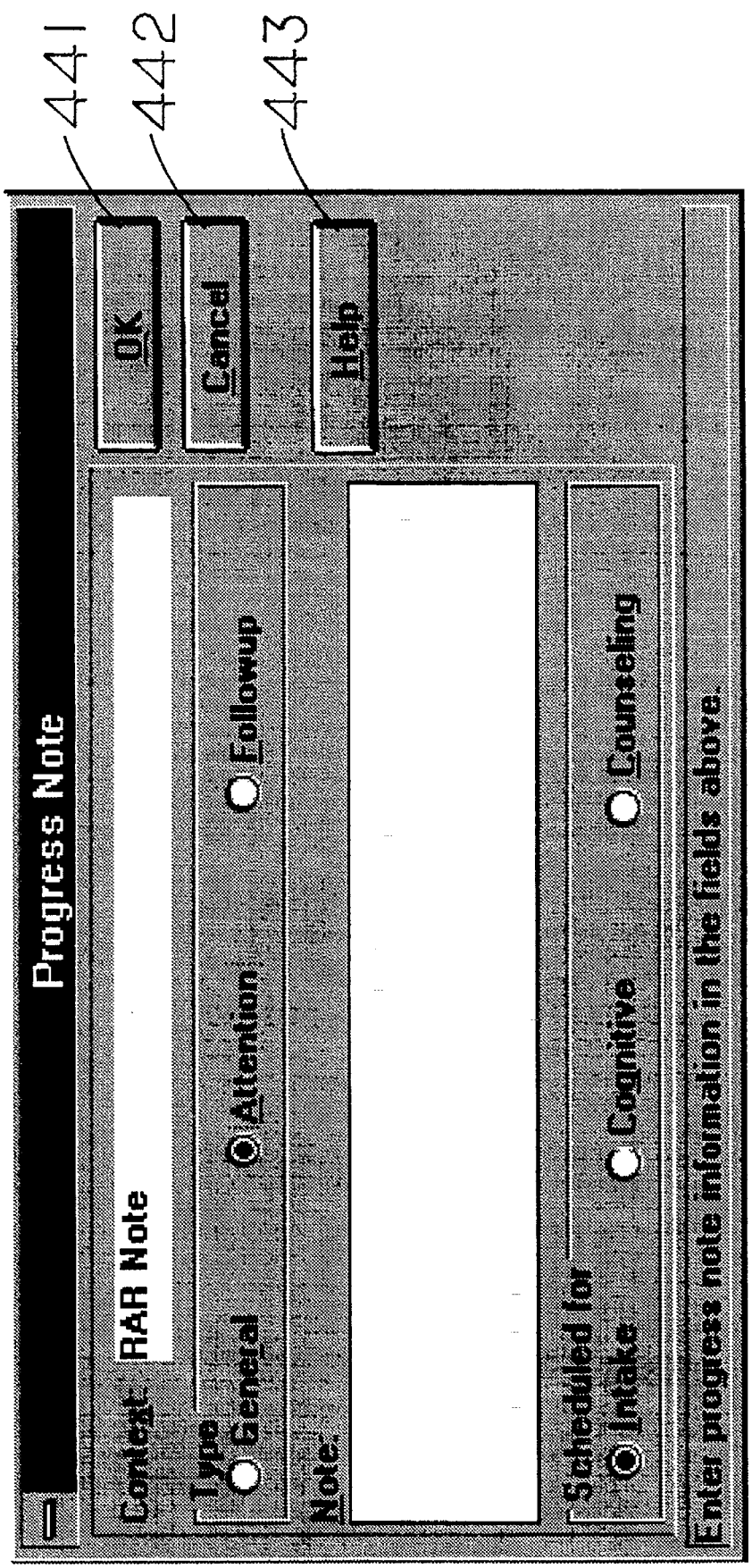

Referring to FIG. 31, an "Attention" note is illustrated. Similar to the general note, the attention note also includes a field to indicate the context for the note as well as "OK," "Cancel" and "Help" keys 441, 442 and 443, respectively. In addition, an indication that the particular note is of the type "Attention" is also displayed as illustrated in the type field. Finally, the attention note also includes a field for listing the part of the process during which the note is to be drawn to the attention of the pharmacy employee (i.e., intake, cognitive or counseling).

Figure 32:
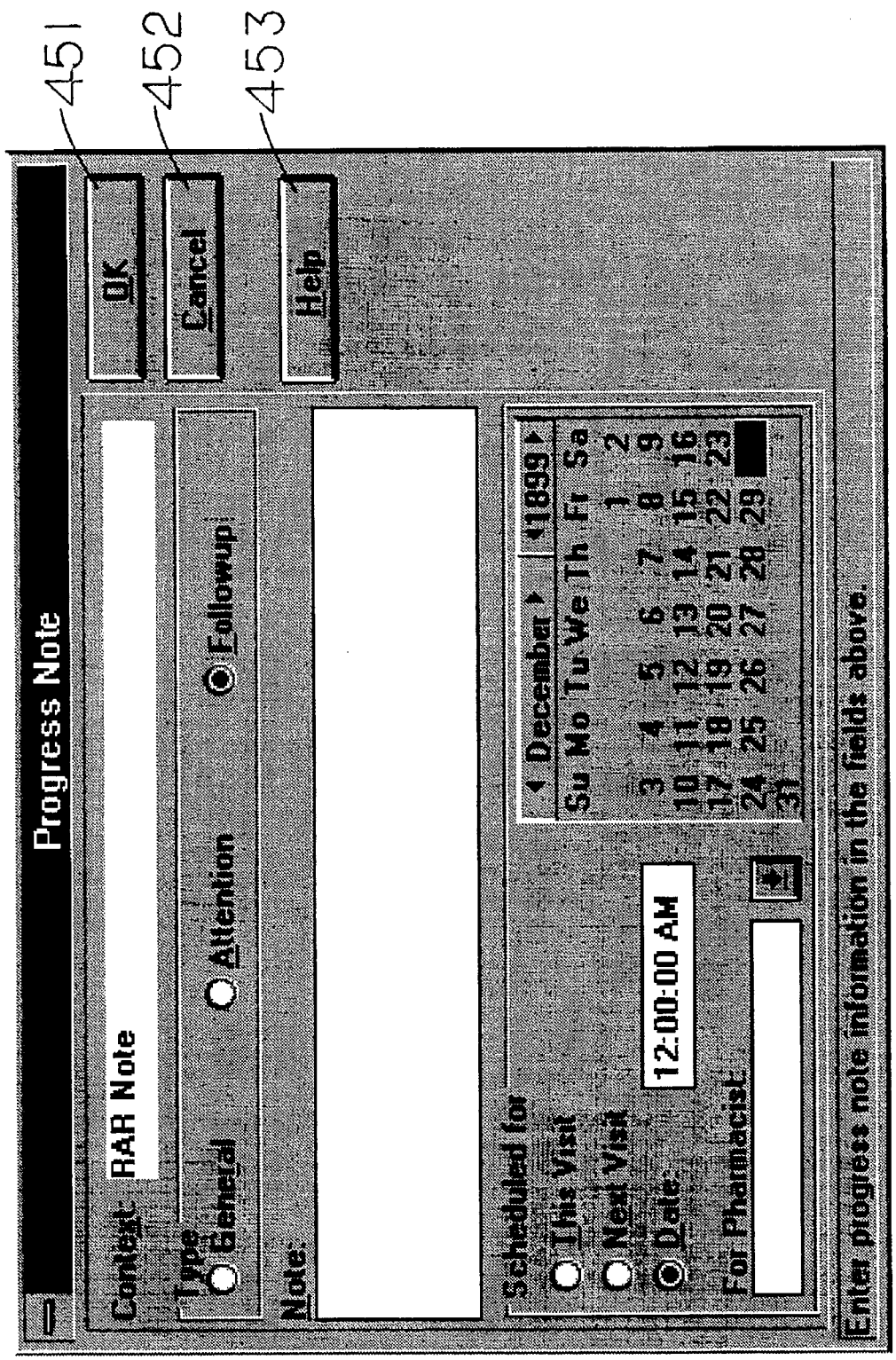

Referring to FIG. 32, a "Follow-up" note is illustrated. Similar to the general note and attention note, the follow-up note also includes a context field and a field for indicating the type of the note as well as the "OK" key 451, "Cancel" key 452 and "Help" key 453. In addition, the follow-up note includes a field for indicating when the note is to be processed (i.e., this visit, next visit, or a particular date), and a calendar which highlights the date for processing the note.

Detailed Operation: Drug Monograph Subsystem

The user may invoke the drug monograph interrupt subsystem by selecting the "Mono" key 110. Similar to the SOAP and Note interrupt subsystems, invoking of the drug monograph subsystem does not suspend any processing of any session. Rather, invoking the drug monograph subsystem results in interruption and termination of the current session being processed by PC-CSMS. Generally, the drug monograph subsystem is simply an interface provided between PC-CSMS and a drug database to allow the user to access drug information. This interface with a drug database will be understood generally by those having skill in the art and may take any number of forms for interfaces between a system such as PC-CSMS 24 and any of the standard drug databases, including that marketed by Medi-Span of Indianapolis, Ind.

Pharmaceutical Care Cognitive Services Management System Menu Bar

The PC-CSMS menu bar illustrated in FIG. 5 which includes the menu bar entries of "File," "Edit," "Views," "Action," "Reports," "Utilities," and "Help" operates like any other menu bar in a Windows environment. Selection of any one of these entries in the menu bar will result in the "pulling down" of a menu from which the user may select a variety of options. Selection of the "File" entry in the menu bar will result in displaying of a menu providing the options of "Save" or "Exit." Selection of the menu bar entry "Edit" provides the user with the options of "Undo," "Cut," "Copy," or "Paste." Selection of the menu bar entry "Views" results in the "pulling down" of a menu providing the user with the options of "Orders," "Patient," "CSR," "Cognitive," or "Counseling." Still further, selection of the menu bar entry "Action" results in the display of a pull-down menu providing the user with the options of "Open PT," "Refill Rx," "SOAP," "Note," and "Monograph." Similarly, selection of the "Reports" option from the menu bar results in the display of a pull-down menu providing the user with the options of "Patient Intake" and "To Do List." Still further, selection of the "Utilities" option from the menu bar results in the display of a pull-down menu providing the user with the options of "Users," "Drug List," "Physicians," and "Diagnoses." Finally, selection of the menu bar entry "Help" will result in the display of a pull-down menu for help options.

Working Example of Multiple RARs Associated With a Single SOAP

Figure 34:
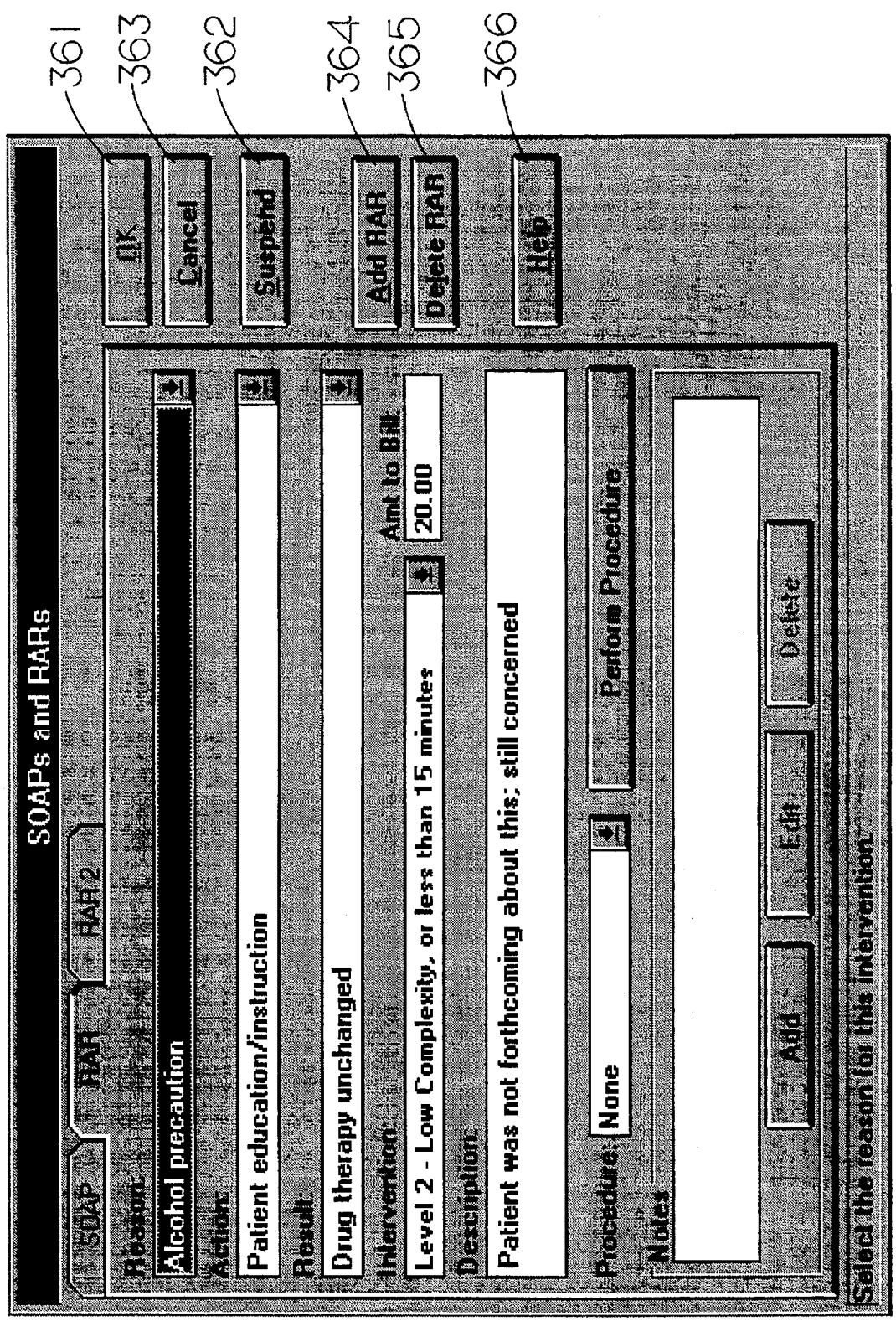
Figure 35:
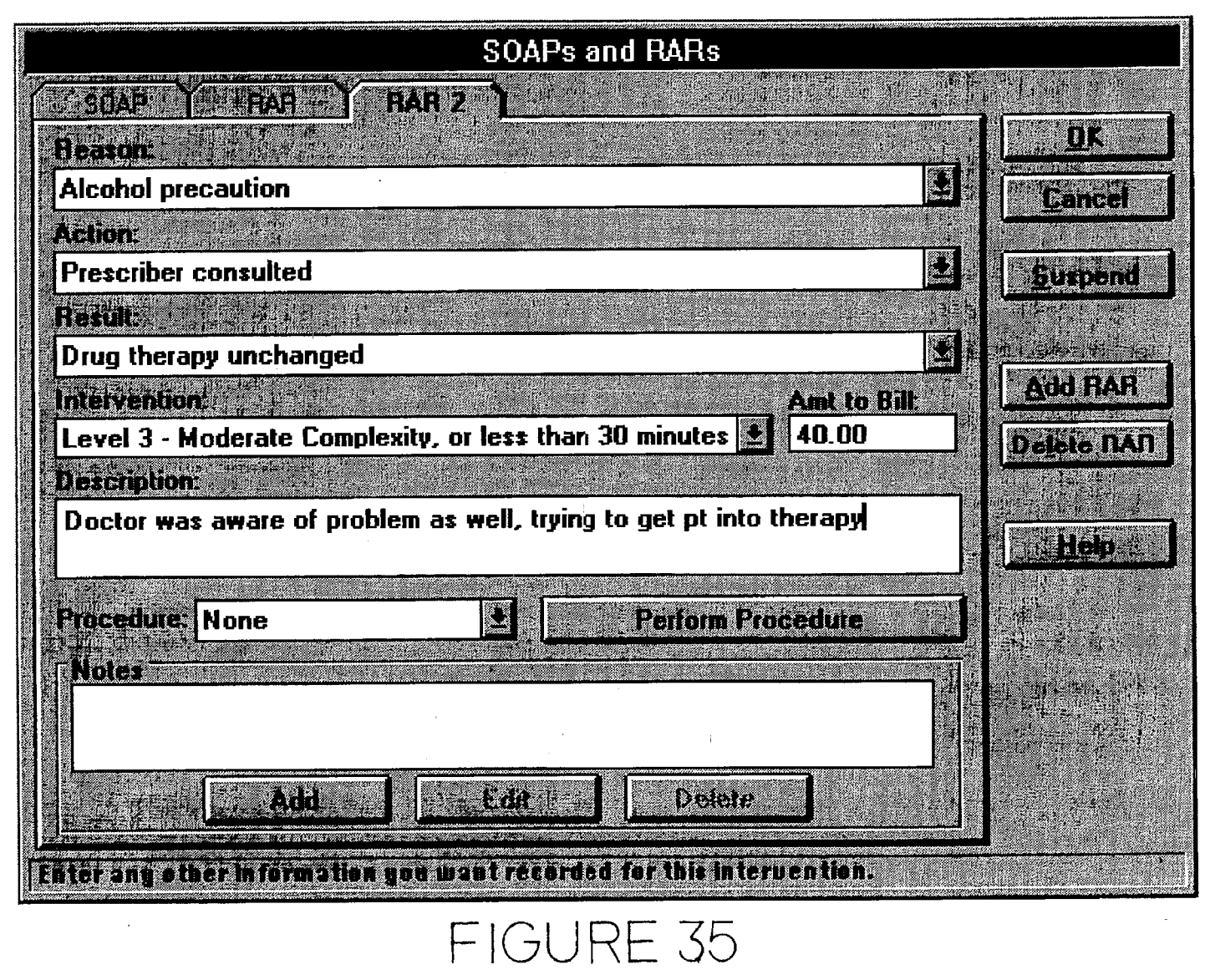

Referring to FIGS. 33–35, a working example of multiple RARs associated with a single SOAP will now be described. Upon selecting the SOAP key 108, a "blank" SOAP tab will be displayed on display device 20. The blank SOAP tab prompts the user to complete the "Context," "Subjective," "Objective," "Assessment," "Plan" and "Procedure" fields. In the particular example illustrated in FIG. 33, the Context is "CSR" which is selected from a list of predefined context as indicated by the "↓" symbol adjacent to the Context field. The user of the system then proceeds to complete the Subjective, Objective, Assessment and Plan fields. In this particular example, the pharmacist has made a subjective observation of the patient in that he believes the patient drinks heavily and has entered this subjective information into the Subjective field. In addition, the pharmacist also has made an objective or factual based observation in that the patient's eyes appear to be bloodshot and his breath smells like liquor at 11:00 a.m., and has entered this factual based information in the Objective field. The user is then prompted to enter an assessment based on the subjective and objective information in the Assessment field. In this particular example, the pharmacist assesses the situation indicating that there could be possible complications with the drug therapy as well as general health problems. Finally, in response to the interactive prompting by the pharmaceutical care cognitive services management system, the pharmacist enters his Plan to be followed based on the assessment. In this particular case, the pharmacist has selected the plan of talking to the patient about complications with the drug therapy and talking to the patient's physician about health issues. The pharmacist has decided not to enter any procedure in the Procedure field at this point.

At this point, the pharmacist can either indicate that the SOAP is completed and commit the SOAP to the database by selecting the "OK" key 351, suspend the processing of the SOAP at this time by selecting the "Suspend" key 352, cancel any updates made to the SOAP by selecting the "Cancel" key 353 or add a RAR to the SOAP by selecting the "Add RAR" key 354.

In response to the selection by the user of the "Add RAR" key 354 in FIG. 33, a blank "RAR" tab screen will be displayed on display device 20 prompting the user to complete the various fields for this first RAR associated with the SOAP. The first RAR of this working example is illustrated in FIG. 34. The user is prompted to complete the "Reason," "Action," "Result," "Intervention," "Description," "Procedure" and "Notes" fields. The user entry for the Reason, Action, Result and Intervention fields may be selected from predefined lists as indicated by the "↓" symbol adjacent to each of those respective fields. In this particular example, the pharmacist, in response to the prompt to complete the Reason field, indicated that the reason was alcohol precaution. In addition, in response to the prompt to complete the Action field, the user entered the action of patient education/instruction. Still further, in response to the system's prompting the user to complete the Result field, the user entered the result as unchanged drug therapy. Still further, in response to the system's prompting the user to complete the Intervention field, the user selected Level 2 for a low complexity or an intervention of less than 15 minutes from the predefined list of intervention options. The user also entered an indication in the Description field that the patient was not forthcoming about the alcohol problem and that the pharmacist is still concerned. Finally, the pharmacist decided not to enter any procedure or notes for this particular RAR.

During the process of completing the RAR, the user has the options of indicating that the RAR has been completed and committing the RAR to the database by selecting the "OK" key 361, suspending the processing of the RAR and allowing it to be completed at a later time by selecting the "Suspend" key 362, or cancelling the updates made to the RAR during this session by selecting the "Cancel" key 363. In addition, the user may add an additional RAR by selecting the "Add RAR" key 364 or delete this RAR by selecting the "Delete RAR" key 365. Finally, the user could select the "Add" key 367 to add a note.

Assuming for purposes of this example that upon completing the first RAR illustrated in FIG. 34, the user selected the "Add RAR" key 364, a second "blank" RAR screen will be displayed on display device 20. An example of the second RAR completed by the user for this example is illustrated in FIG. 35. PC-CSMS prompts the user to complete the Reason, Action, Result, Intervention, Description, Procedure and Notes fields as with other RARs. In this particular example of the second RAR, the user has selected the same reason as being alcohol precaution. Since this is a different RAR, the user has selected a different action, i.e., prescriber consulted, to indicate that an action different from that taken in the first RAR is to be taken in this second RAR. The user in the second RAR also selected the unchanged drug therapy as the result. In this second RAR, the user indicated that the intervention level was Level 3 indicating that the intervention required by the pharmacist to consult with the physician was of moderate complexity or less than 30 minutes. Finally, the user indicated in the Description field that the doctor was aware of the problem and is trying to get the patient into alcohol therapy. Similar to any other RAR, the user may select the options of "OK," "Suspend," "Cancel," "Add RAR" and "Delete RAR."

As noted above, the user could add a third and a fourth RAR to this particular SOAP. In any event, each of these RARs are associated with the SOAP indicated at the tab adjacent to the RAR tab in FIGS. 33–35.

Working Example of Patient Interrupt

Referring to FIGS. 36–41, a working example of processing by the patient interrupt subsystem of a patient interrupt will now be described. Upon selecting the "Pt." key 106, PC-CSMS 24 will suspend the current session if the current session is either a cognitive or a counseling session. In response to selection of the "Pt." key 106, PC-CSMS 24 will prompt the user to indicate whether the user wants to suspend the cognitive or counseling session, or cancel the interrupt and continue the cognitive or counseling session (see FIGS. 23 and 24). If the user selects to suspend the present cognitive or counseling session, the present session will be suspended and control is transferred to the patient intake subsystem, and displays "Patient Intake" on display device 20. Otherwise, the user may cancel any other session being currently processed and transfer control to the "Patient Intake" display.

Figure 36:
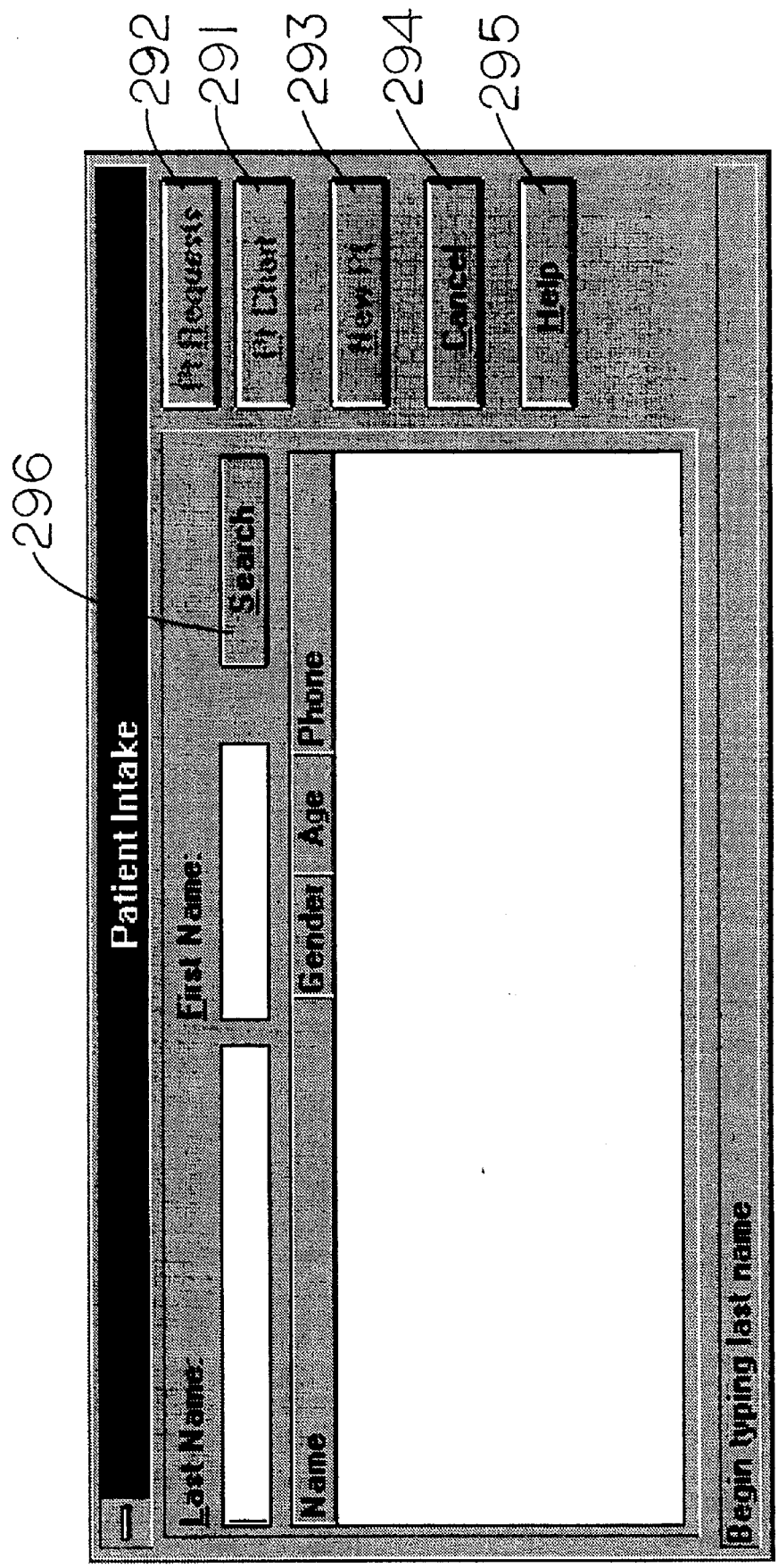

Referring to FIG. 36, the system prompts the user to enter the name of the patient interrupting the user in the fields "Last Name" and "First Name" as illustrated in FIG. 36. If no names are displayed in a list of names, then the user must enter the "Last Name" and "First Name" in the appropriate fields. Otherwise, if names are listed in the list of names, the user may select one of those names by either entering the name in the "Last Name" and "First Name" fields or selecting the name from the list using an appropriate input device. While the "Last Name" and "First Name" fields remain empty, the "Pt Chart" key 291, "Pt Requests" 292, "New Pt" key 293 and "Search" key 296 are not enabled.

Upon entering a last name such as, for example, a name beginning with the letter "R" as illustrated in FIG. 37, PC-CSMS 24 then displays a list of patient names in the Name Table and searches the list of names for a match between the name entered by the user and those contained in the list of patient names. Upon locating the first match, PC-CSMS then enables "Pt Chart" key 291 and "Pt Requests" key 292 to permit the user to either transfer control to the patient chart component of the patient intake subsystem for the patient listed, or take in a prescription for the patient listed by selecting the "Pt Chart" key 291 or "Pt Requests" key 292, respectively.

Figure 38:
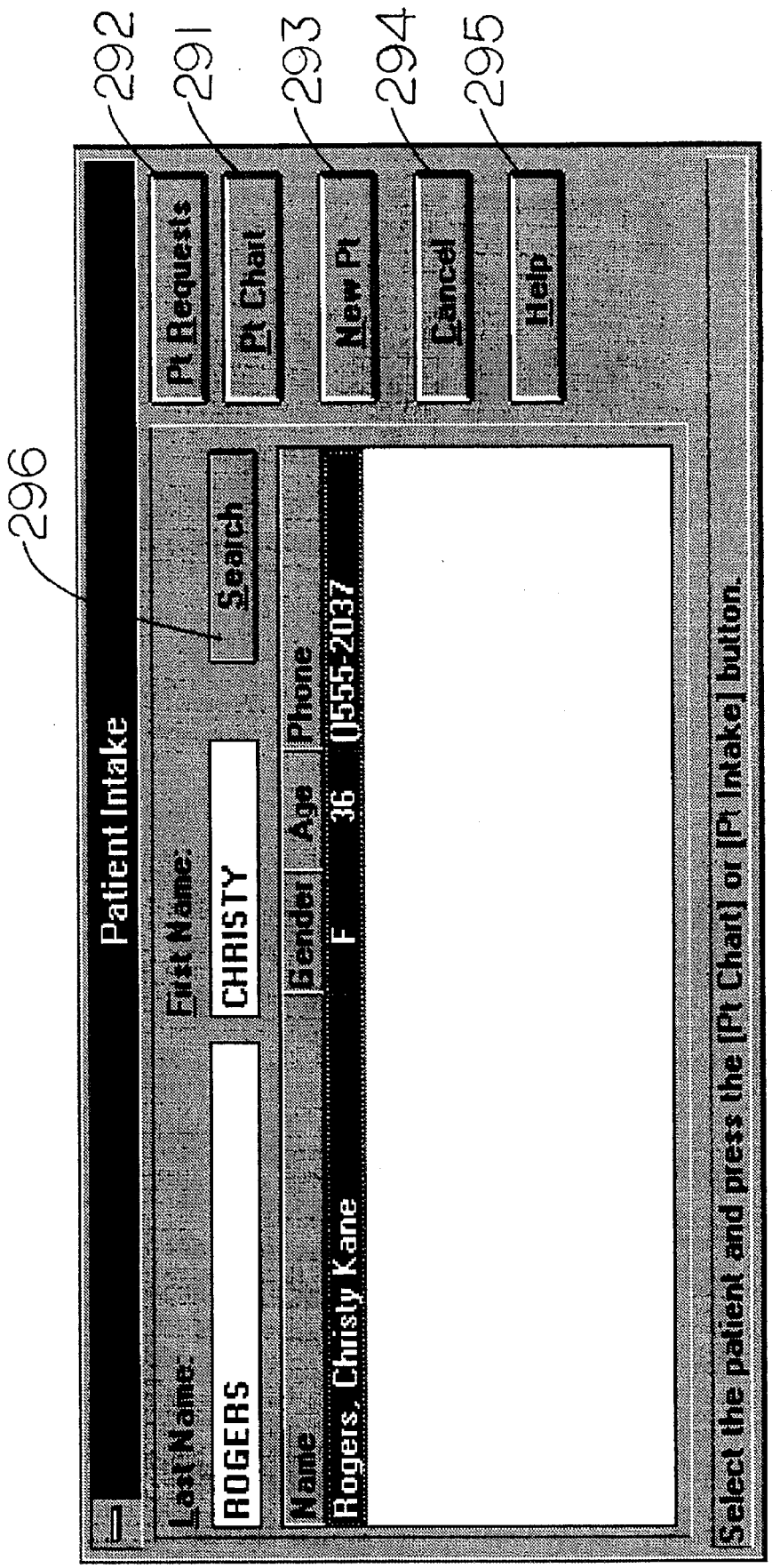
Figure 40:
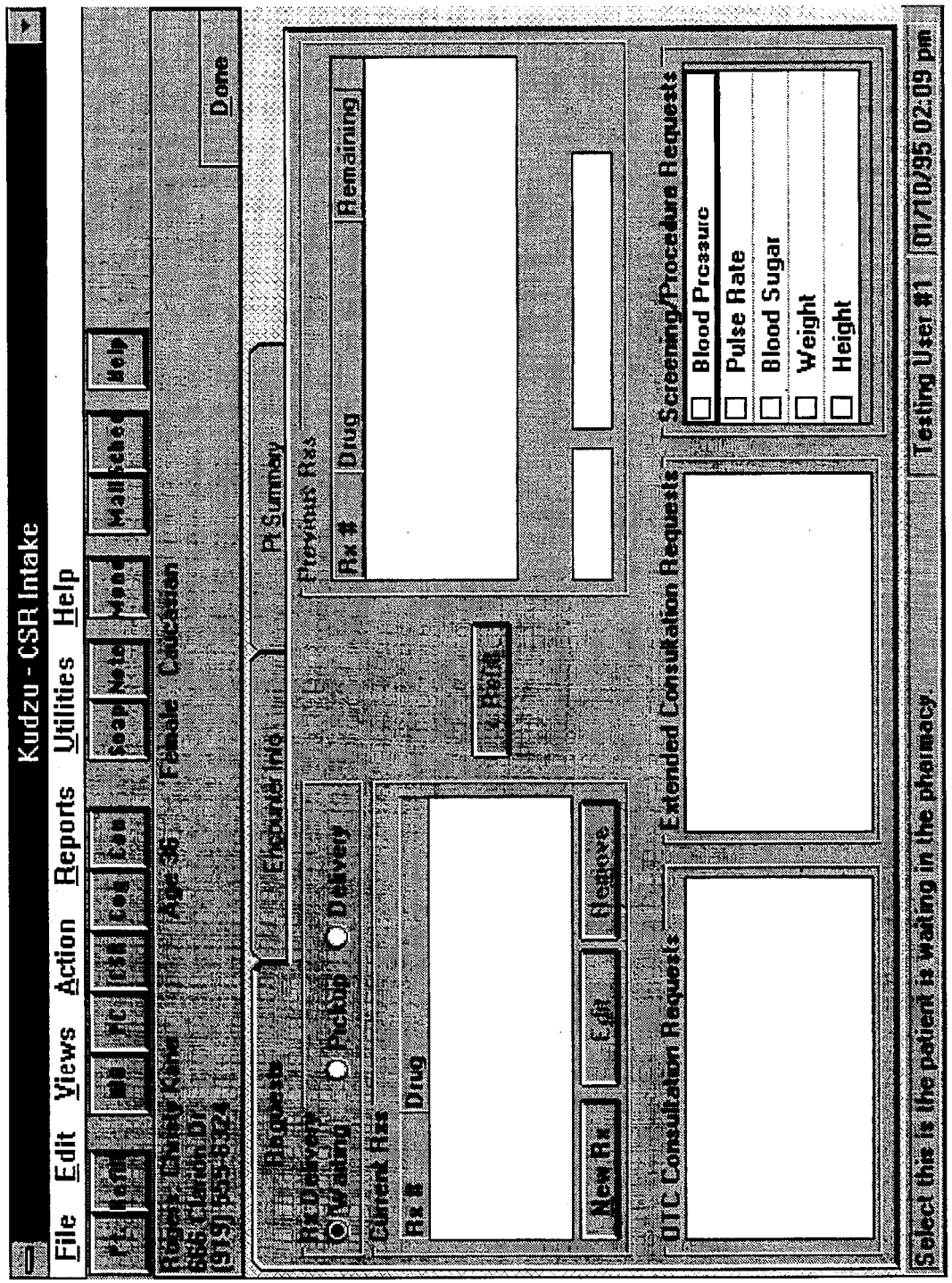

As the user continues to enter the name of the second patient who is interrupting the user, PC-CSMS 24 will continue to search the list of patient names for the closest match among those names listed in the list of patient names. Referring to FIG. 38, the user has entered "Rogers" in the Last Name field and "Christy" in the First Name field. In response, PC-CSMS 24 locates the name "Rogers, Christy Kane" in the list of patient names. The system, in addition to continuing to enable the "Pt Chart" key 291 and "Pt Requests" key 292, also enables the "New Pt" key 293 since PC-CSMS is not sure whether the patient name entered by the user is the patient highlighted in the list of patient names or is a new patient with the same first name. At this stage, the user may either select to review the patient chart or intake a prescription for this patient during which steps the user will confirm that this interrupting second patient is the same as the patient name highlighted in the list of patient names. However, if the user knows that the patient name entered by the user is not the same person as that highlighted in the list of patient names, the user can then transfer to process this second patient as a new patient by selecting the "New Pt" key 293.

Figure 39:
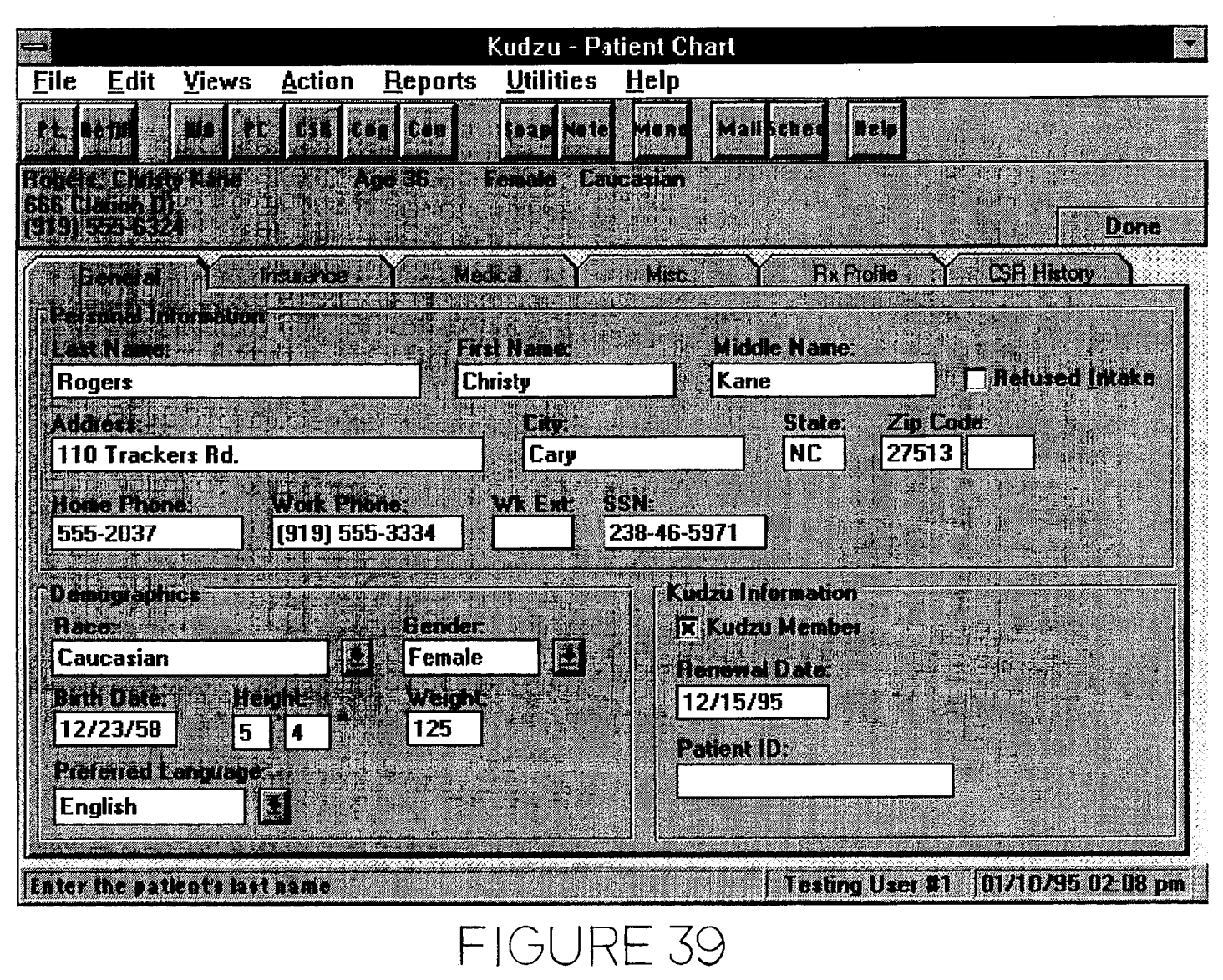

Assuming for purposes of this example that the user selects the "Pt Chart" key 291, control is transferred to the patient chart component of the patient intake subsystem resulting in display of the "General" tab as illustrated in FIG. 39 for the patient name highlighted in the list of patient names illustrated in FIG. 38. At this point, the user can determine based on the personal information listed in the general tab for the patient chart for the second patient whether the second patient is, in fact, the same as the patient whose information is displayed on the screen illustrated in FIG. 39. Thus, the user can review the patient chart. In addition, at this stage, the user can also update any field of the patient chart within any of the tabs including "General," "Insurance," "Medical," "Miscellaneous," "Drug Profile" and "CSR History."

Referring to FIG. 38, if the user selected the "Pt Requests" key 292 for the patient whose name is highlighted in the list of patient names, control is transferred to the cognitive service record component of the patient intake subsystem to begin the task of taking in an over-the-counter or prescription drug. As a result, PC-CSMS 24 displays the "Requests" tab for the cognitive service record for the patient whose name was highlighted in the list of patient names in FIG. 38 (see FIG. 40). At this point, processing by the interrupt subsystem of the patient interrupt continues with the processing of the cognitive service record component in the same manner as that described above with respect to the processing of cognitive service record sessions.

Figure 41:
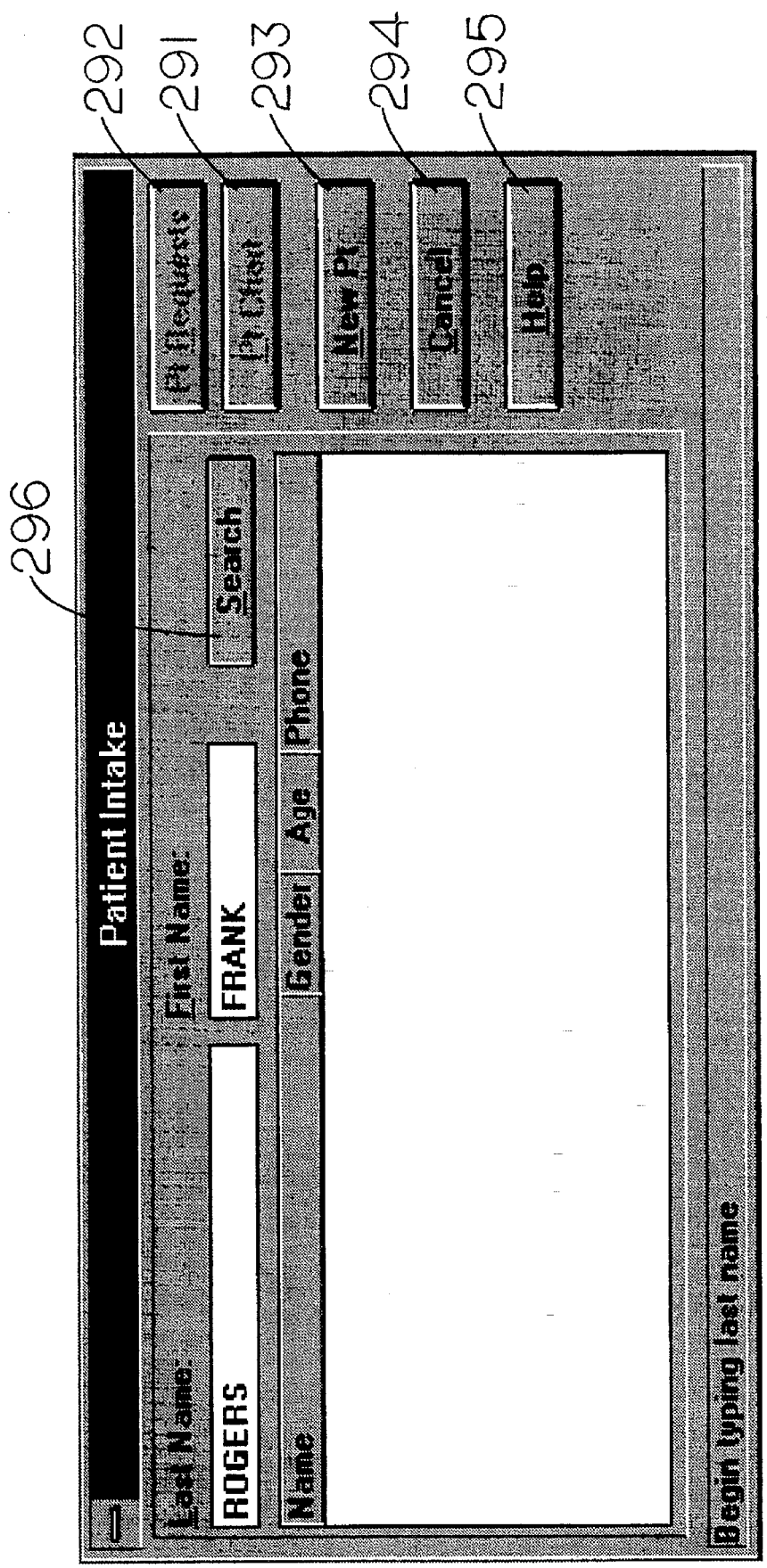
Figure 43:
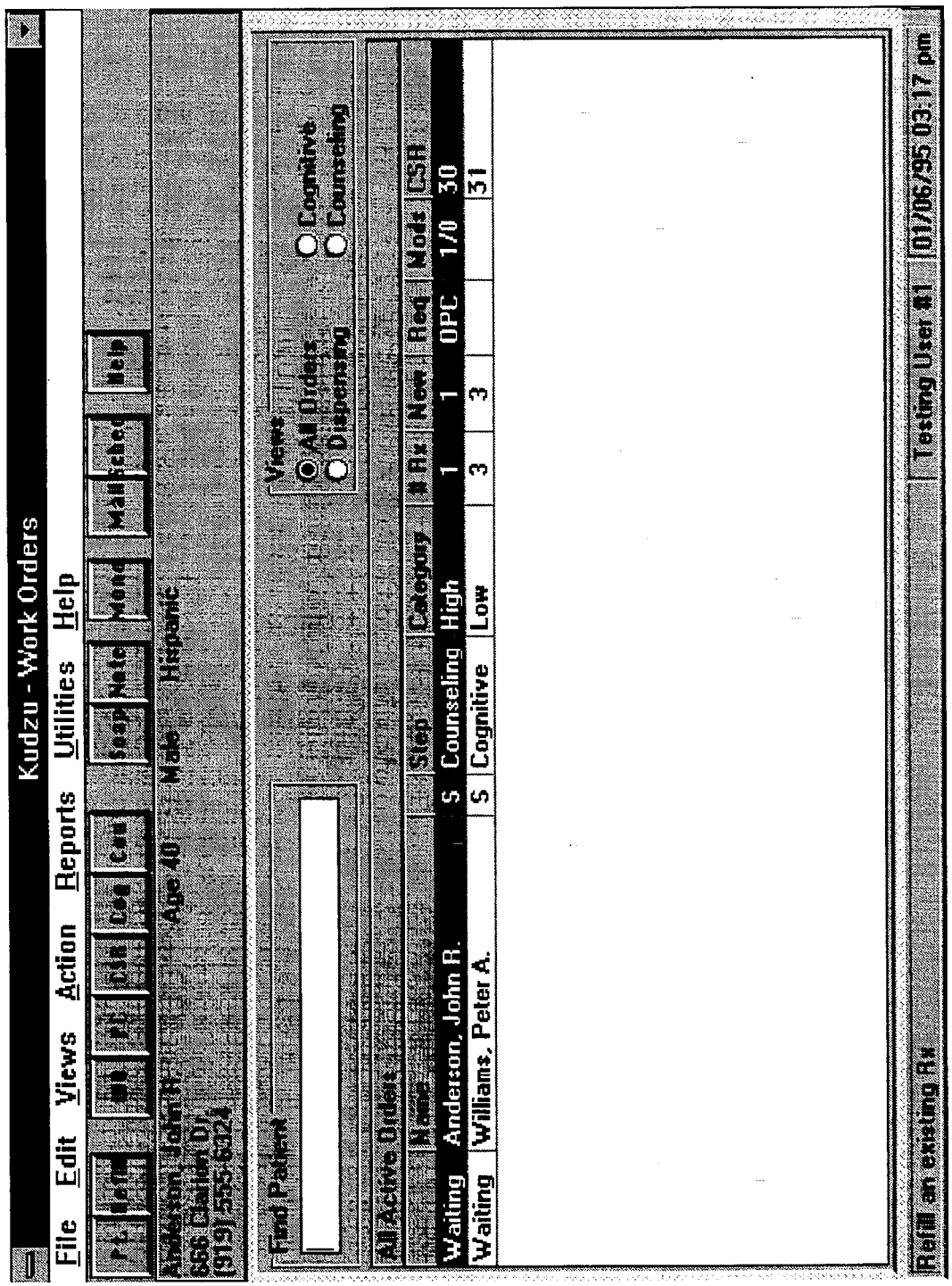

Referring again to FIG. 37, if the user entered a name in the First Name field such that PC-CSMS 24 would not find a match with those names contained in the list of patient names, no names would be displayed in that list of patient names, and PC-CSMS 24 would enable the "New Pt" key 293 but disenable the "Pt Chart" key 291 and "Pt Requests" key 292. Referring to FIG. 41, the user entered the name "Frank" in the First Name field resulting in the finding of no match with any of the names contained in the list of patient names. As a result, the user can only select to add the second patient who is interrupting the user (i.e., Frank Rogers) as a new patient to PC-CSMS or terminate the patient interrupt, or seek online help.

Assuming for purposes of this example that the user decided to add the interrupting patient (i.e., Frank Rogers) as a new patient to PC-CSMS 24, the system will open a new patient chart upon the selection of the "New Pt" key 293 and transfer control to the new patient chart for this new patient.

Figure 42:
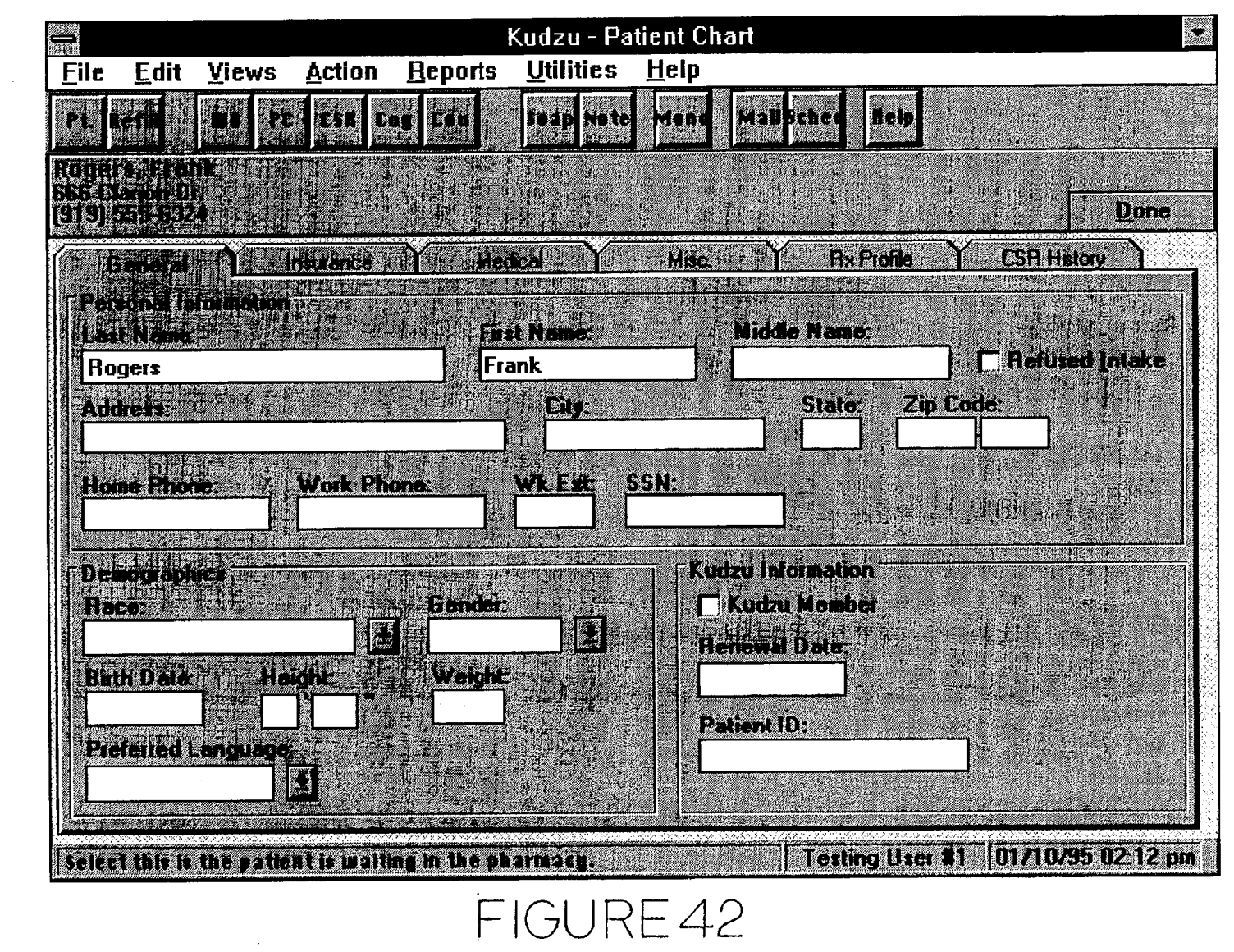

As a result of the transfer of control, PC-CSMS displays the "General" tab for the new patient chart which contains only the "Last Name" and the "First Name" of the new patient as illustrated in FIG. 42. At this point, the user may continue to collect information relating to the patient's identity and history to be included in the patient chart and stored by PC-CSMS 24. Thereafter, processing continues as previously described with respect to the detailed operation of the patient chart component of the patient intake subsystem noted above. Upon completion of the processing of the patient chart for the new patient, PC-CSMS 24 may resume processing of the interrupted or suspended cognitive or counseling session by transferring control to the cognitive subsystem or counseling subsystem, respectively.

Working Example of a Refill Interrupt

Figure 44:
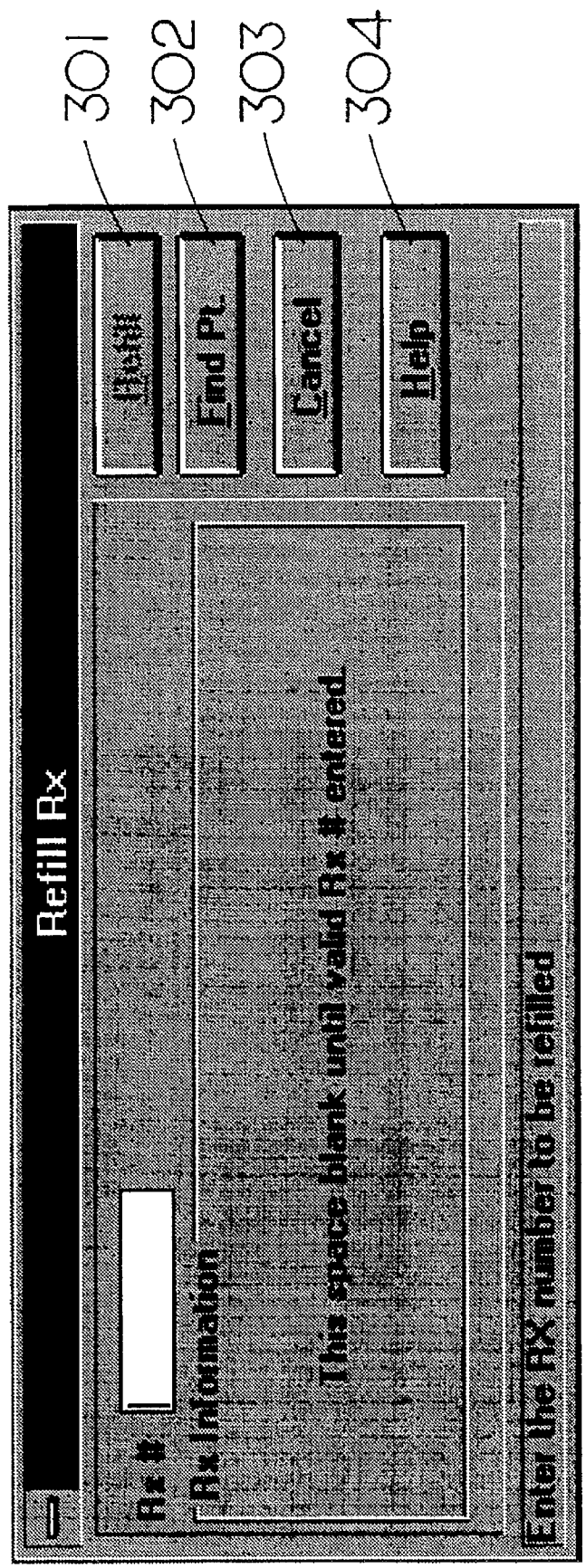
Figure 45:
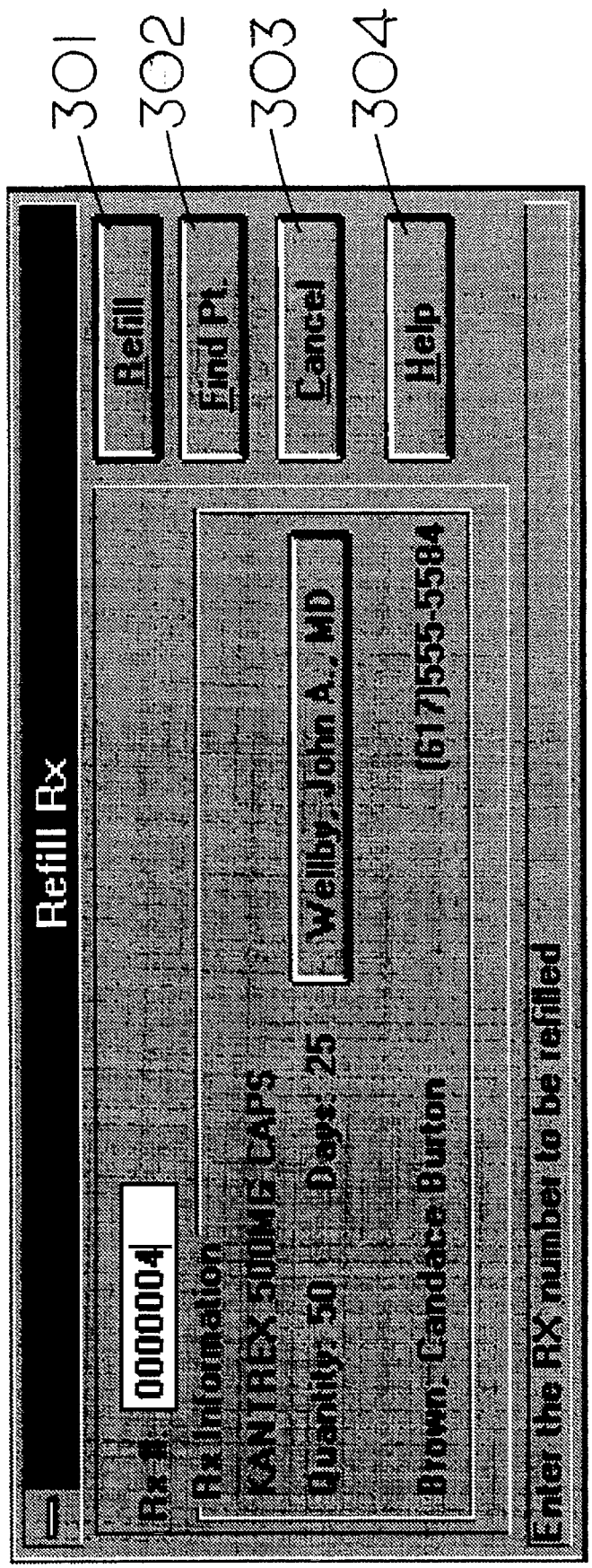

Referring to FIGS. 43-48, a working example of processing by the interrupt subsystem of a refill interrupt will now be described. Upon selecting "Refill" key 107, PC-CSMS 24 will suspend the session presently being processed if the present session is a cognitive or counseling session, process the refill interrupt, and upon completion of processing of the refill interrupt, resume processing of the suspended cognitive or counseling session. The user has the option of preventing the suspension of the current cognitive or counseling session, and rather, cancelling the interrupt and continuing the present cognitive or counseling session. Upon selection of the Refill key 107 from the display illustrated in FIG. 43, PC-CSMS 24 indicates that the "Refill" interrupt has been invoked and then displays a screen prompting the user to enter the number for the prescription which is to be refilled by displaying the screen illustrated in FIG. 44. Until the user enters a prescription number, only the "Find Pt" key 302, "Cancel" key 303 and "Help" key 304 are enabled. The "Refill" key 301 is not enabled until a prescription number is entered by the user and PC-CSMS confirms that the entered prescription is valid. Once the user enters a prescription number in the appropriate field, PC-CSMS 24 searches the data storage device to determine whether the prescription number is a valid prescription (i.e., whether the prescription number is in the data storage device). In this example, PC-CSMS 24 has determined that the prescription number entered by the user (i.e., "0000004") is a valid prescription number and, as a result, displays basic information relating to the prescription number on display device 20 as illustrated in FIG. 45. In addition, upon determining that the prescription is valid, PC-CSMS 24 enables the "Refill" key 301 to allow the user to request that the prescription be refilled.

Figure 46:
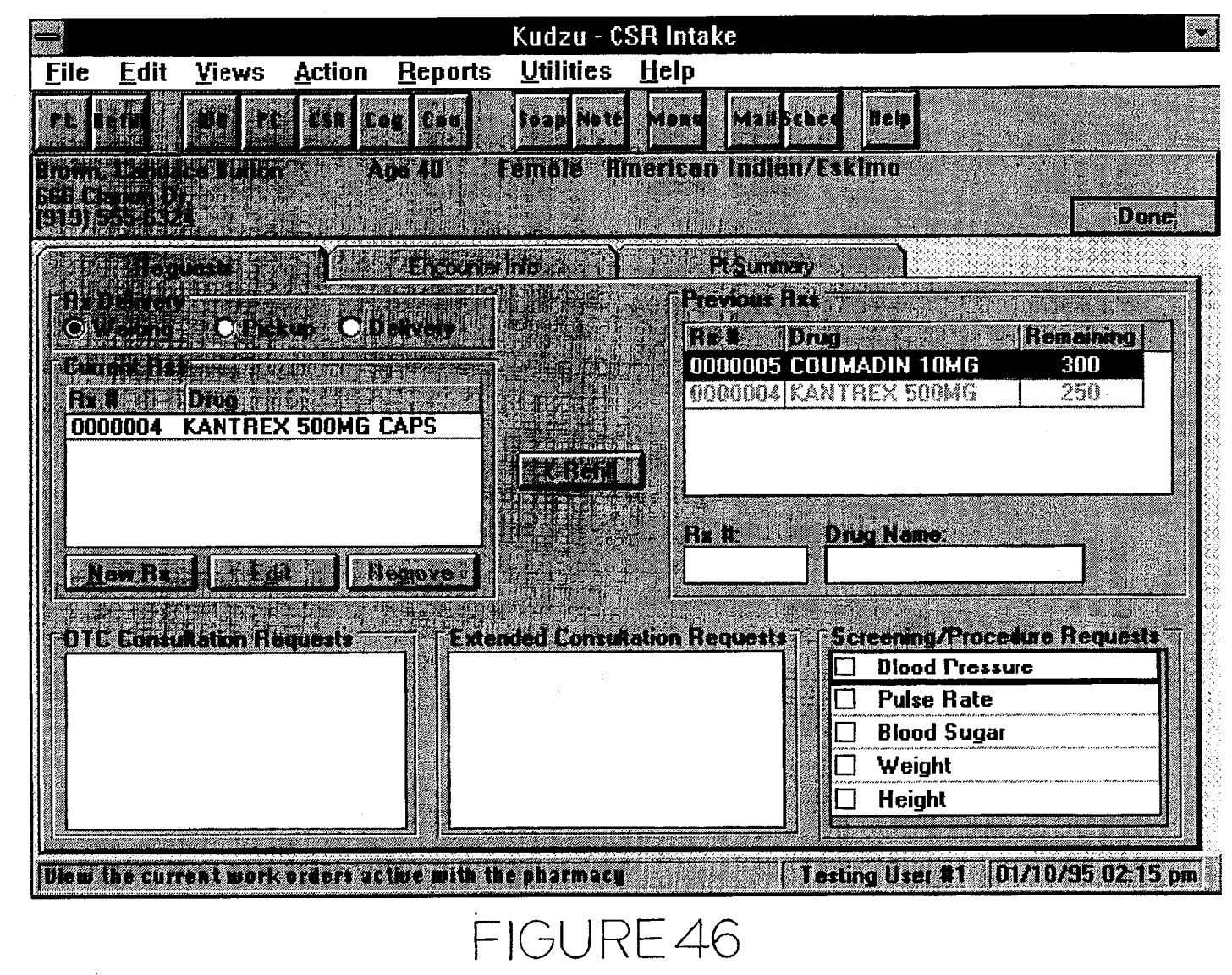

Upon selection of the "Refill" key 301, PC-CSMS 24 transfers control to the cognitive service record component of the patient intake subsystem resulting in the display of the "Request" tab of the cognitive service record on display device 20 as illustrated in FIG. 46. Information for the drug corresponding to the prescription number will be displayed in the current prescription list. At this point, processing continues with the refill interrupt in the same manner as it does for processing of the cognitive service record described above. Once processing by the interrupt subsystem of the refill interrupt is completed for the second patient, PC-CSMS 24 may resume processing of the suspended cognitive or counseling session.

Figure 47:
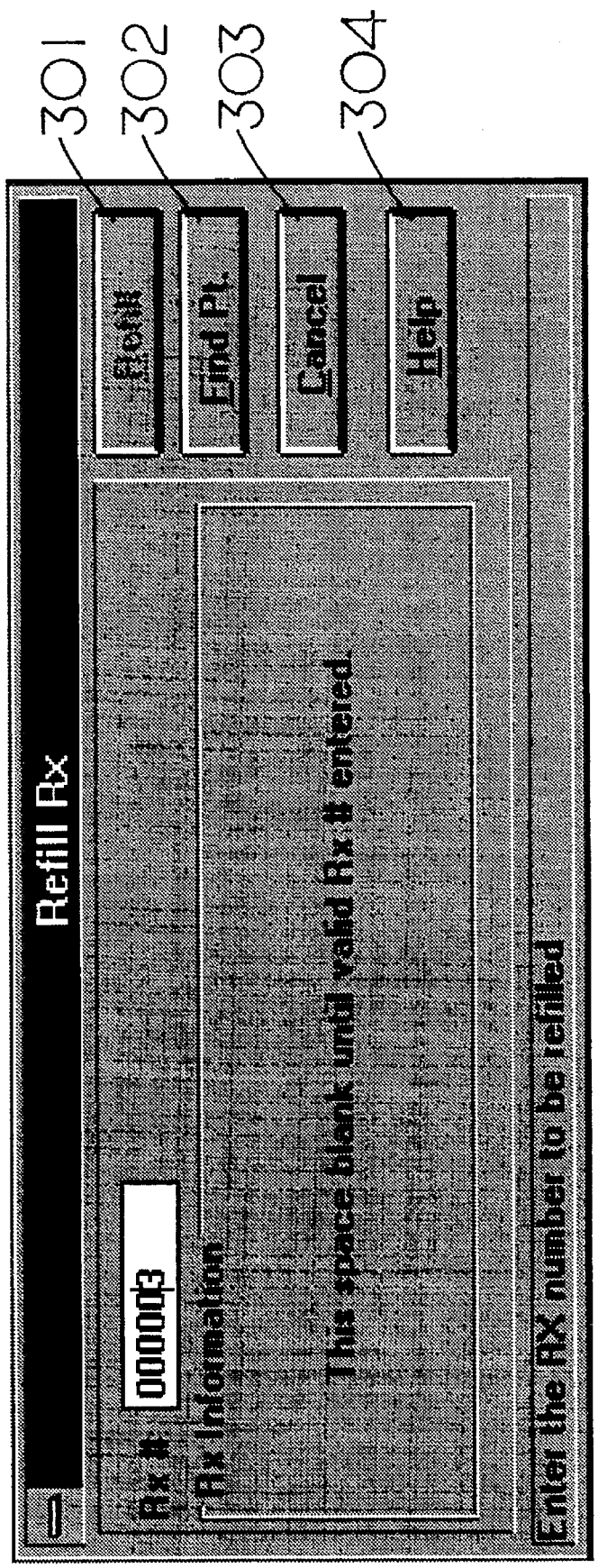

As mentioned above, the user is prompted to enter a prescription number as illustrated in FIG. 44. In response to this prompting, the user entered the number "000000." Upon receiving the entry of this prescription number, PC-CSMS 24 compares the prescription number against those prescription numbers contained in the data storage device to determine whether the. prescription number is valid. In this example, the user entered the prescription number "0000003," which is not valid as illustrated in FIG. 47. As a result, no information is displayed in the prescription information section. Further, the "Refill" key 301 is disenabled. The only options available to the user are to find the patient, cancel the refill interrupt or seek online help. In response to the selection of the "Find Pt." key 302, PC-CSMS 24 begins processing what is essentially the patient interrupt by displaying on display device 20 the patient intake screen as illustrated in FIG. 48. As a result, the user is prompted to enter the last name of the second patient who is interrupting the cognitive or counseling session. Thereafter, PC-CSMS 24 processes this refill interrupt as in the same manner as that for a patient interrupt, and upon completion of the processing of this interrupt, resumes processing of the suspended cognitive or counseling session.

In the drawings and specification, there have been disclosed typical preferred embodiments of the invention and, although specific terms are employed, they are used in a generic and descriptive sense only and not for purposes of limitation, the scope of the invention being set forth in the following claims.

That which is claimed:

1. A computer based pharmaceutical care cognitive services management method which executes on a computer system including processing means, data storage means, display means and input means, said computer based pharmaceutical care cognitive services management method comprising the steps of:

prompting on said display means for user entry via said input means, and for storing in said data storage means, of identity and history information corresponding to a patient;

prompting on said display means for user entry via said input means, and for storing in said data storage means, of subjective information relating to assessed characteristics of said patient and objective information relating to said patient's history of drug use;

prompting on said display means for user entry via said input means, and for storing in said data storage means, of an assessment of said patient based upon said subjective information and said objective information;

prompting on said display means for user entry via said input means, and for storing in said data storage means, of a plan to follow based on said assessment;

prompting on said display means for user entry via said input means, and for storing in said data storage means, of a first reason for the assessment and the plan, a first action in response to the assessment and the plan, and a first result based on the first action;

prompting on said display means for user entry via said input means, and for storing in said data storage means, of a second reason for the assessment and the plan, a second action in response to the assessment and the plan, and a second result based on the second action;

associating the stored first reason, first action and first result and the stored second reason, second action and second result with the stored subjective information, objective information, assessment and plan, such that a plurality of reasons, actions and results are associated with the stored subjective information, objective information, assessment and plan for a patient;

generating a first billing statement for said patient based on the stored first reason, first action and first result associated with the stored subjective information, objective information, assessment and plan for said patient; and generating a second billing statement for said patient based on the stored second reason, second action and second result associated with the stored subjective information, objective information, assessment and plan for said patient;

such that two billing statements are generated for one patient based on the stored subjective information, objective information, assessment and plan.

2. The computer based pharmaceutical care cognitive services management method of claim 1 further comprising the steps of:

prompting on said display means for user entry via said input means, and for storing in said data storage means, of a third reason for the assessment and the plan, a third action in response to the assessment and the plan, and a third result based on the third action;

associating the stored third reason, third action and third result with the stored first reason, first action and first result, the stored second reason, second action and second result, and the stored subjective information, objective information, assessment and plan, such that the stored first reason, first action and first result, the stored second reason, second action and second result and the stored third reason, third action and third result are each associated with the stored subjective information, objective information, assessment and plan for a patient.

3. The computer based pharmaceutical care cognitive services management method of claim 2 further comprising the step of:

generating a third billing statement for said patient based on the stored third reason, third action and third result associated with the stored subjective information, objective information, assessment and plan for said patient;

such that a third billing statement is generated for one patient based on the stored subjective information, objective information, assessment and plan.

4. The computer based pharmaceutical care cognitive services management method of claim 1 further comprising the steps of:

prompting on said display means for user entry via said input means, and for storing in said data storage means, of an identification of a drug; and associating the identification of the drug stored in said data storage means with the identity of said patient stored in said data storage means.

5. The computer based pharmaceutical care cognitive services management method of claim 4 further comprising the steps of:

comparing the identification of the drug stored in said data storage means and the identity and history information corresponding to said patient stored in said data storage means; and prompting for user entry via said input means, and for storing in said data storage means, of alteration of said identification of said drug based on the result of said comparing step, and said stored subjective information, objective information, assessment and plan;

such that the identification of said drug is changed by said user.

6. The computer based pharmaceutical care cognitive services management method of claim 4 further comprising the step of:

transferring the identification of the drug in association with the identity of said patient to a dispensing system; such that said drug is dispensed to said patient.

7. The computer based pharmaceutical care cognitive services management method of claim 4 further comprising the step of:

generating a billing statement for said patient based on the identification of the drug stored in said storage means;

such that a billing statement is generated for said patient based on the stored subjective information, objective information, assessment and plan.

8. The computer based pharmaceutical care cognitive services management method of claim 1 further comprising the step of generating a report for said patient based on said stored subjective information, objective information, assessment and plan, and said stored first reason, first action and first result, and said stored second reason, second action and second result associated with said stored subjective information, objective information, assessment and plan.

9. A computer based pharmaceutical care cognitive services management system comprising:

a computer system including processing means, data storage means, display means and input means;

first prompting means, for prompting on said display means for user entry via said input means, and for storing in said data storage means, of identity and history information corresponding to a patient;

second prompting means, for prompting on said display means for user entry via said input means, and for storing in said data storage means, of subjective information relating to assessed characteristics of said patient and objective information relating to said patient's history of drug use;

third prompting means, for prompting on said display means for user entry via said input means, and for storing in said data storage means, of an assessment of said patient based upon said subjective information and said objective information;

fourth prompting means, for prompting on said display means for user entry via said input means, and for storing in said data storage means, of a plan to follow based on said assessment;

fifth prompting means, for prompting on said display means for user entry via said input means, and for storing in said data storage means, of a first reason for the assessment and the plan, a first action in response to the assessment and the plan, and a first result based on the first action;

sixth prompting means, for prompting on said display means for user entry via said input means, and for storing in said data storage means, of a second reason for the assessment and the plan, a second action in response to the assessment and the plan, and a second result based on the second action;

associating means, for associating the stored first reason, first action and first result and the stored second reason, second action and second result with the stored subjective information, objective information, assessment and plan, such that a plurality of reasons, actions and results are associated with the stored subjective information, objective information, assessment and plan for said patient;

first generating means, for generating a first billing statement for said patient based on the stored first reason, first action and first result; and second generating means, for generating a second billing statement for said patient based on the stored second reason, second action and second result;

such that two billing statements are generated for said patient based on the stored subjective information, objective information, assessment and plan.

10. The computer based pharmaceutical care cognitive services management system of claim 9 further comprising:

seventh prompting means, for prompting on said display means for user entry via said input means, and for storing in said data storage means, of an identification of a drug; and second associating means, for associating the identification of the drug stored in said data storage means with the identity of said patient stored in said data storage means.

11. The computer based pharmaceutical care cognitive services management system of claim 10 further comprising:

comparing means, for comparing the identification of the drug stored in said data storage means and the identify and history information corresponding to said patient stored in said data storage means to produce an indication of possible incompatibilities between said drug and said patient; and eighth prompting means, for prompting for user entry via said input means, and for storing in said data storage means, of alteration of said identification of said drug based on the indication of possible incompatibilities, and said stored subjective information, objective information, assessment and plan;

such that the identification of said drug is changed by said user.

12. The computer based pharmaceutical care cognitive services management system of claim 10 further comprising:

a dispensing system; and transferring means, for transferring the identification of the drug in association with the identity of said patient to said dispensing system;

such that said drug is dispensed to said patient.

13. The computer based pharmaceutical care cognitive services management system of claim 10 further comprising:

third generating means, for generating a billing statement for said patient based on the identification of the drug stored in said storage means;

such that a billing statement is generated for said patient based on the stored subjective information, objective information, assessment and plan.

* * * * *